(12) United States Patent
Gross et al.

(10) Patent No.: US 9,017,399 B2
(45) Date of Patent: Apr. 28, 2015

(54) TECHNIQUES FOR PERCUTANEOUS MITRAL VALVE REPLACEMENT AND SEALING

(75) Inventors: Yossi Gross, Moshav Mazor (IL); Gil Hacohen, Ramot Hashavim (IL); Eran Miller, Moshav Beit Elazari (IL); Yuval Zipory, Modi'in (IL)

(73) Assignee: Mitraltech Ltd., Or Yehuda (IL)

( * ) Notice: Subject to any disclaimer, the term of this patent is extended or adjusted under 35 U.S.C. 154(b) by 0 days.

(21) Appl. No.: 13/811,308

(22) PCT Filed: Jul. 21, 2011

(86) PCT No.: PCT/IL2011/000582
§ 371 (c)(1),
(2), (4) Date: Mar. 7, 2013

(87) PCT Pub. No.: WO2012/011108
PCT Pub. Date: Jan. 26, 2012

(65) Prior Publication Data
US 2013/0172992 A1    Jul. 4, 2013

Related U.S. Application Data

(63) Continuation-in-part of application No. 12/840,463, filed on Jul. 21, 2010, and a continuation-in-part of application No. 13/033,852, filed on Feb. 24, 2011, which is a continuation-in-part of application No. 12/840,463.

(60) Provisional application No. 61/492,449, filed on Jun. 2, 2011.

(51) Int. Cl.
*A61F 2/24* (2006.01)
*A61B 17/068* (2006.01)
(Continued)

(52) U.S. Cl.
CPC ............ *A61F 2/2466* (2013.01); *A61B 17/068* (2013.01); *A61B 2017/00243* (2013.01);
(Continued)

(58) Field of Classification Search
USPC ............. 623/2.1, 2.11, 2.12, 2.17, 2.18, 2.36, 623/2.37, 2.38, 2.4, 2.41, 2.42, 904
See application file for complete search history.

(56) References Cited

U.S. PATENT DOCUMENTS

| 4,261,342 A | 4/1981 | Aranguren Duo |
| 4,423,525 A | 1/1984 | Vallana et al. |

(Continued)

FOREIGN PATENT DOCUMENTS

| EP | 1264582 A2 | 12/2002 |
| WO | 99/30647 A1 | 6/1999 |

(Continued)

OTHER PUBLICATIONS

USPTO NFOA dated Sep. 12, 2013 in connection with U.S. Appl. No. 13/412,814.

(Continued)

*Primary Examiner* — Dianne Dornbusch
*Assistant Examiner* — Robert Lynch
(74) *Attorney, Agent, or Firm* — Ladas & Parry LLP

(57) ABSTRACT

Apparatus and methods are described including a prosthetic valve support (40) configured to be placed at a patient's native atrioventricular valve annulus. The valve support defines an annular element (44) that defines an inner cross-sectional area thereof. An expandable prosthetic valve (80) is placed into the patient's ventricle, the prosthetic valve including an expandable frame (79) and prosthetic valve leaflets (82) coupled to the frame. When the frame is in a non-constrained state thereof, a cross-sectional area of the frame, along at least a given portion L of the frame's length, is greater than the cross-sectional area defined by the annular element. The prosthetic valve is couplable to the prosthetic valve support at any location along the portion, by the frame being expanded when the location along the portion is aligned with the annular element. Other applications are also described.

9 Claims, 43 Drawing Sheets

(51) Int. Cl.
 *A61B 17/00* (2006.01)
 *A61B 17/064* (2006.01)

(52) U.S. Cl.
 CPC . *A61B2017/0647* (2013.01); *A61B 2017/0649* (2013.01); *A61F 2/2409* (2013.01); *A61F 2/2418* (2013.01); *A61F 2/2436* (2013.01); *A61F 2/2487* (2013.01); *A61F 2250/0063* (2013.01); *A61F 2/2457* (2013.01); *A61F 2220/0016* (2013.01); *A61F 2230/005* (2013.01); *A61F 2230/0054* (2013.01)

(56) References Cited

U.S. PATENT DOCUMENTS

| | | | |
|---|---|---|---|
| 4,853,986 A | 8/1989 | Allen |
| 4,892,541 A | 1/1990 | Alonso |
| 5,108,420 A | 4/1992 | Marks |
| 5,607,444 A | 3/1997 | Lam |
| 5,607,470 A | 3/1997 | Milo |
| 5,868,777 A | 2/1999 | Lam |
| 6,042,607 A | 3/2000 | Williamson, IV et al. |
| 6,074,417 A | 6/2000 | Peredo |
| 6,113,612 A | 9/2000 | Swanson et al. |
| 6,120,534 A | 9/2000 | Ruiz |
| 6,152,937 A | 11/2000 | Peterson et al. |
| 6,187,020 B1 | 2/2001 | Zegdi et al. |
| 6,287,339 B1 | 9/2001 | Vazquez et al. |
| 6,332,893 B1 | 12/2001 | Mortier et al. |
| 6,391,036 B1 | 5/2002 | Berg et al. |
| 6,402,780 B2 | 6/2002 | Williamson, IV et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | DiMatteo et al. |
| 6,458,153 B1 | 10/2002 | Bailey et al. |
| 6,511,491 B2 | 1/2003 | Grudem et al. |
| 6,530,952 B2 | 3/2003 | Vesely |
| 6,540,782 B1 | 4/2003 | Snyders |
| 6,558,418 B2 | 5/2003 | Carpentier et al. |
| 6,602,263 B1 | 8/2003 | Swanson et al. |
| 6,616,675 B1 | 9/2003 | Evard et al. |
| 6,699,256 B1 | 3/2004 | Logan et al. |
| 6,716,244 B2 | 4/2004 | Klaco |
| 6,719,781 B1 | 4/2004 | Kim |
| 6,730,118 B2 | 5/2004 | Spenser et al. |
| 6,767,362 B2 | 7/2004 | Schreck |
| 6,797,002 B2 | 9/2004 | Spence et al. |
| 6,830,585 B1 | 12/2004 | Artof et al. |
| 6,830,638 B2 | 12/2004 | Boylan et al. |
| 6,960,217 B2 | 11/2005 | Bolduc |
| 6,964,684 B2 | 11/2005 | Ortiz et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,172,625 B2 | 2/2007 | Shu et al. |
| 7,198,646 B2 | 4/2007 | Figulla et al. |
| 7,201,772 B2 | 4/2007 | Schwammenthal et al. |
| 7,288,111 B1 | 10/2007 | Holloway et al. |
| 7,335,213 B1 | 2/2008 | Hyde et al. |
| 7,351,256 B2 | 4/2008 | Hojeibane et al. |
| 7,404,824 B1 | 7/2008 | Webler et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,527,646 B2 | 5/2009 | Rahdert et al. |
| 7,582,111 B2 | 9/2009 | Krolik et al. |
| 7,585,321 B2 | 9/2009 | Cribier |
| 7,632,302 B2 | 12/2009 | Vreeman et al. |
| 7,708,775 B2 | 5/2010 | Rowe et al. |
| 7,717,955 B2 | 5/2010 | Lane et al. |
| 7,731,741 B2 | 6/2010 | Eidenschink |
| 7,753,922 B2 | 7/2010 | Starksen |
| 7,758,595 B2 | 7/2010 | Allen et al. |
| 7,771,467 B2 | 8/2010 | Svensson |
| 7,771,469 B2 | 8/2010 | Liddicoat |
| 7,776,083 B2 | 8/2010 | Vesely |
| 7,780,726 B2 | 8/2010 | Seguin |
| 7,799,069 B2 | 9/2010 | Bailey et al. |
| 7,803,181 B2 | 9/2010 | Furst et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler |
| 7,947,072 B2 | 5/2011 | Yang et al. |
| 7,947,075 B2 | 5/2011 | Goetz et al. |
| 7,955,375 B2 | 6/2011 | Agnew |
| 7,955,384 B2 | 6/2011 | Rafiee et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka |
| 7,993,393 B2 | 8/2011 | Carpentier et al. |
| 8,002,825 B2 | 8/2011 | Letac et al. |
| 8,016,877 B2 | 9/2011 | Seguin |
| 8,016,882 B2 | 9/2011 | Macoviak et al. |
| 8,021,420 B2 | 9/2011 | Dolan |
| 8,021,421 B2 | 9/2011 | Fogarty et al. |
| 8,029,564 B2 | 10/2011 | Johnson et al. |
| 8,034,104 B2 | 10/2011 | Carpentier et al. |
| 8,043,360 B2 | 10/2011 | McNamara et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock |
| 8,070,802 B2 | 12/2011 | Lamphere et al. |
| 8,070,804 B2 | 12/2011 | Hyde et al. |
| 8,075,611 B2 | 12/2011 | Millwee et al. |
| 8,080,054 B2 | 12/2011 | Rowe |
| 8,083,793 B2 | 12/2011 | Lane et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Rahdert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,014 B2 | 4/2012 | Lane et al. |
| 8,167,894 B2 | 5/2012 | Miles et al. |
| 8,167,932 B2 | 5/2012 | Bourang et al. |
| 8,167,935 B2 | 5/2012 | McGuckin, Jr. |
| 8,172,896 B2 | 5/2012 | McNamara et al. |
| 8,177,836 B2 | 5/2012 | Lee et al. |

(56) References Cited

U.S. PATENT DOCUMENTS

| | | |
|---|---|---|
| 8,182,528 B2 | 5/2012 | Salahieh et al. |
| 8,211,169 B2 | 7/2012 | Lane et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,343,174 B2 | 1/2013 | Goldfarb et al. |
| 8,430,934 B2 | 4/2013 | Das |
| 8,449,625 B2 | 5/2013 | Campbell et al. |
| 8,628,571 B1 | 1/2014 | Hacohen et al. |
| 8,696,742 B2 | 4/2014 | Pintor |
| 2001/0021872 A1 | 9/2001 | Bailey et al. |
| 2002/0032481 A1 | 3/2002 | Gabbay |
| 2002/0151970 A1 | 10/2002 | Garrison et al. |
| 2003/0036791 A1 | 2/2003 | Philipp et al. |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0039414 A1 | 2/2004 | Carley et al. |
| 2004/0093060 A1 | 5/2004 | Seguin et al. |
| 2004/0122514 A1 | 6/2004 | Fogarty et al. |
| 2004/0176839 A1 | 9/2004 | Huynh et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0225354 A1 | 11/2004 | Allen et al. |
| 2004/0260389 A1 | 12/2004 | Case et al. |
| 2005/0004668 A1 | 1/2005 | Aklog et al. |
| 2005/0075731 A1 | 4/2005 | Artof et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0143809 A1 | 6/2005 | Salahieh et al. |
| 2005/0197695 A1 | 9/2005 | Stacchino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0267573 A9 | 12/2005 | Macoviak et al. |
| 2006/0047297 A1 | 3/2006 | Case |
| 2006/0135964 A1 | 6/2006 | Vesely |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195184 A1 | 8/2006 | Lane et al. |
| 2006/0201519 A1 | 9/2006 | Frazier et al. |
| 2006/0241656 A1 | 10/2006 | Starksen et al. |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0271166 A1 | 11/2006 | Thill et al. |
| 2006/0271171 A1 | 11/2006 | McQuinn et al. |
| 2006/0287719 A1 | 12/2006 | Rowe et al. |
| 2007/0016288 A1 | 1/2007 | Gurskis et al. |
| 2007/0027549 A1 | 2/2007 | Godin |
| 2007/0038295 A1 | 2/2007 | Case et al. |
| 2007/0043435 A1 | 2/2007 | Seguin et al. |
| 2007/0112422 A1 | 5/2007 | Dehdashtian |
| 2007/0118151 A1 | 5/2007 | Davidson |
| 2007/0162103 A1 | 7/2007 | Case |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198097 A1 | 8/2007 | Zegdi |
| 2007/0213813 A1 | 9/2007 | Von Segesser et al. |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0086164 A1 | 4/2008 | Rowe |
| 2008/0086204 A1 | 4/2008 | Rankin |
| 2008/0161910 A1 | 7/2008 | Revuelta et al. |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0243245 A1 | 10/2008 | Thambar et al. |
| 2008/0262609 A1 | 10/2008 | Gross et al. |
| 2008/0281411 A1 | 11/2008 | Berreklouw |
| 2009/0005863 A1 | 1/2009 | Goetz et al. |
| 2009/0054969 A1 | 2/2009 | Salahieh et al. |
| 2009/0099650 A1 | 4/2009 | Bolduc et al. |
| 2009/0171363 A1 | 7/2009 | Chocron |
| 2009/0177278 A1 | 7/2009 | Spence |
| 2009/0210052 A1 | 8/2009 | Forster et al. |
| 2009/0264994 A1 | 10/2009 | Saadat |
| 2009/0306768 A1 | 12/2009 | Quadri |
| 2009/0319037 A1 | 12/2009 | Rowe et al. |
| 2010/0023117 A1 | 1/2010 | Yoganathan et al. |
| 2010/0036479 A1 | 2/2010 | Hill et al. |
| 2010/0076548 A1 | 3/2010 | Konno |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0262232 A1 | 10/2010 | Annest |
| 2010/0280603 A1 | 11/2010 | Maisano et al. |
| 2010/0280606 A1 | 11/2010 | Naor |
| 2010/0324595 A1 | 12/2010 | Linder et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0106247 A1 | 5/2011 | Miller et al. |

(56) References Cited

U.S. PATENT DOCUMENTS

| | | |
|---|---|---|
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282440 A1 | 11/2011 | Cao et al. |
| 2011/0283514 A1 | 11/2011 | Fogarty et al. |
| 2011/0288634 A1 | 11/2011 | Tuval et al. |
| 2011/0295363 A1 | 12/2011 | Girard et al. |
| 2011/0301688 A1 | 12/2011 | Dolan |
| 2011/0301701 A1 | 12/2011 | Padala et al. |
| 2011/0301702 A1 | 12/2011 | Rust et al. |
| 2011/0313452 A1 | 12/2011 | Carley et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101572 A1 | 4/2012 | Kovalsky et al. |
| 2012/0123530 A1 | 5/2012 | Carpentier et al. |
| 2012/0136434 A1 | 5/2012 | Carpentier et al. |
| 2012/0150218 A1 | 6/2012 | Sandgren et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0310328 A1 | 12/2012 | Olson |
| 2012/0323316 A1 | 12/2012 | Chau et al. |
| 2013/0035759 A1 | 2/2013 | Gross et al. |
| 2013/0261737 A1 | 10/2013 | Costello |
| 2013/0304197 A1 | 11/2013 | Buchbinder |
| 2013/0325114 A1 | 12/2013 | McLean et al. |
| 2014/0005778 A1 | 1/2014 | Buchbinder |
| 2014/0052237 A1 | 2/2014 | Lane |

FOREIGN PATENT DOCUMENTS

| | | |
|---|---|---|
| WO | 00/47139 A1 | 8/2000 |
| WO | 01/62189 A1 | 8/2001 |
| WO | 01/87190 A2 | 11/2001 |
| WO | 2006/054930 A1 | 5/2006 |
| WO | 2008/013915 A3 | 1/2008 |
| WO | 2009/033469 A1 | 3/2009 |
| WO | 2009/053497 A1 | 4/2009 |
| WO | 2010/006627 A1 | 1/2010 |
| WO | 2010/073246 A2 | 7/2010 |
| WO | 2011/069048 A2 | 6/2011 |
| WO | 2011/106137 A1 | 9/2011 |
| WO | 2011/111047 A2 | 9/2011 |
| WO | 2011/137531 A1 | 11/2011 |
| WO | 2012/011108 A2 | 1/2012 |
| WO | 2012/127309 | 9/2012 |
| WO | 2013/021375 A2 | 2/2013 |
| WO | 2013/021384 A2 | 2/2013 |
| WO | 2013/078497 A1 | 6/2013 |
| WO | 2013/128436 A1 | 9/2013 |

OTHER PUBLICATIONS

An International Search Report and Written Opinion both dated Mar. 17, 2014, which issued during the prosecution of Applicant's PCT/IL13/0937.

International Preliminary Report on Patentability dated Dec. 2, 2013; PCT/IL2011/000582.

Alexander S. Geha, et al; "Replacement of Degenerated Mitral and Aortic Bioprostheses Without Explanation", Ann. Thorac Surg. Jun. 2001; vol. 72; pp. 1509-1514.

Frank Langer, et al; "Ring plus String: Papillary muscle repositioning as an adjunctive repair technique for ischemic mitral regurgitation", The Journal of Thoracic and Cariovascular Surgery, vol. 133, pp. 247-249, Jan. 2007.

Frank Langer, et al; "Ring + String Successful Repair Technique for Ischemic Mitral Regurgitation With Severe Leaflet Tethering", Circulation; vol. 120[Suppl 1]: pp. S85-S91, Sep. 2009.

J. Jansen, et al; Detachable shape-memory sewing ring for heart valves, Artificial Organs, vol. 16, pp. 294-297. Jun. 1992 abstract only.

John G Webb, et al; "Transcatheter Valve-in-Valve Implantation for Failed Bioprosthetic Heart Valves", Circulation, vol. 121; pp. 1848-1857, Published online Apr. 12, 2010.

International Preliminary Report on Patentability dated Sep. 11, 2012; PCT/IL2011/000231.

International Search Report and Written Opinion dated Dec. 5, 2011; pCT/IL11/00582.

International Search Report and Written Opinion dated Feb. 6, 2013; PCT/IL12/00292.

International Search Report and Written Opinion dated Feb. 6, 2013; PCT/IL12/00293.

(56) References Cited

OTHER PUBLICATIONS

International Search Report and Written Opinion dated Oct. 13, 2011; PCT/IL11/00231.
U.S. Appl. No. 61/492,449 dated Jun. 2, 2011.
U.S. Appl. No. 61/515,372 dated Feb. 6, 2011.
U.S. Appl. No. 61/525,281 dated Aug. 19, 2011.
U.S. Appl. No. 61/537,276 dated Sep. 21, 2011.
U.S. Appl. No. 61/555,160 dated Nov. 3, 2011.
U.S. Appl. No. 61/588,892 dated Jan. 20, 2012.
USPTO NFOA dated May 29, 2012 in connection with U.S. Appl. No. 12/840,463.
USPTO FOA dated Feb. 15, 2013 in connection with U.S. Appl. No. 12/840,463.
USPTO NFOA dated Nov. 28, 2012 in connection with U.S. Appl. No. 12/961,721.
USPTO NFOA dated Nov. 23, 2012 in connection with U.S. Appl. No. 13/033,852.
USPTO NFOA dated Dec. 31, 2012 in connection with U.S. Appl. No. 13/044,694.
USPTO FOA dated Feb. 6, 2013 in connection with U.S. Appl. No. 13/412,814.
An Office Action dated Aug. 2, 2013, which issued during the prosecution of U.S. Appl. No. 13/033,852.
Invitation to Pay Additional Fees dated Jun. 12, 2014 PCT/IL2014/050087.
USPTO NFOA dated Jun. 17, 2014 in connection with U.S. Appl. No. 12/961,721.
USPTO NFOA dated Jul. 3, 2014 in connection with U.S. Appl. No. 13/033,852.
USPTO FOA dated May 23, 2014 in connection with U.S. Appl. No. 13/412,814.
Dominique Himbert; Mitral Regurgitation and Stenosis from Bioprosthesis and Annuloplasty Failure: Transcatheter Approaches and Outcomes, 24 pages Oct. 28, 2013.
International Search Report and Written Opinion dated Sep. 4, 2014; PCT/IL2014/050087.

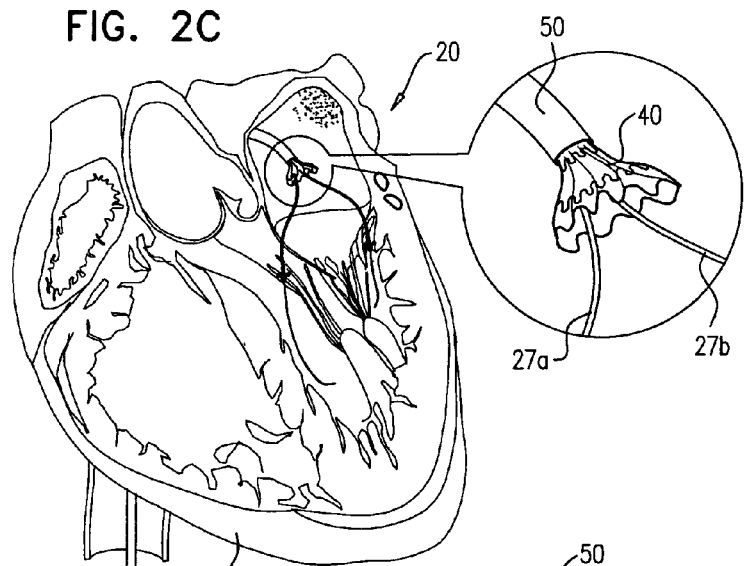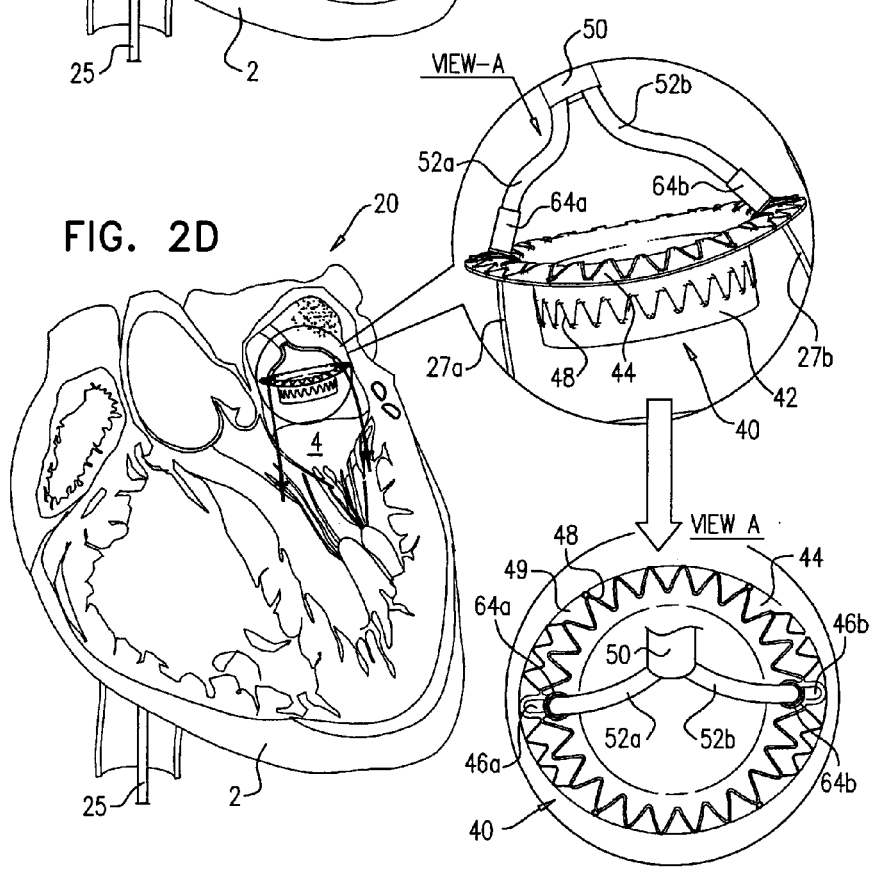

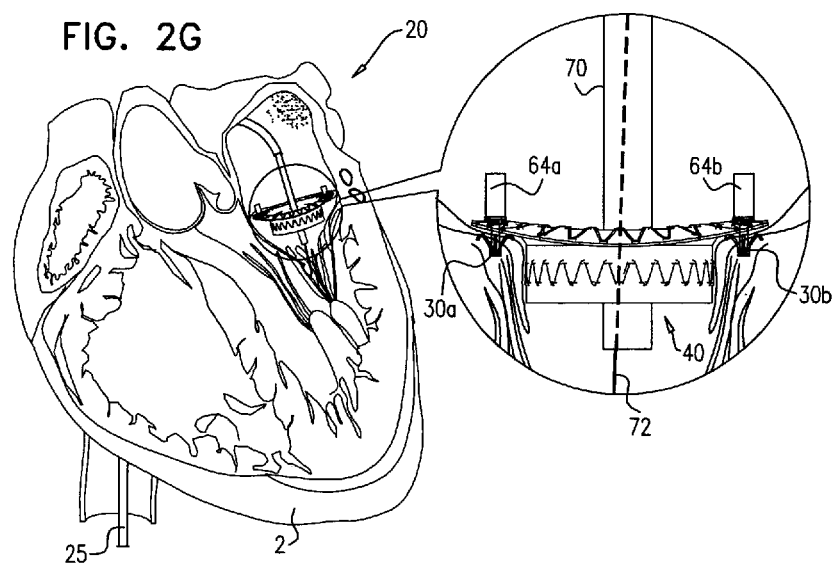
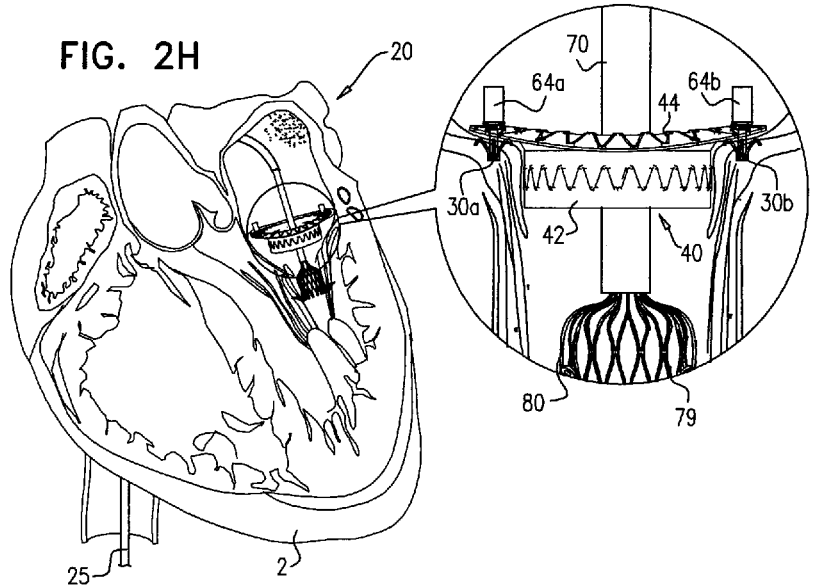

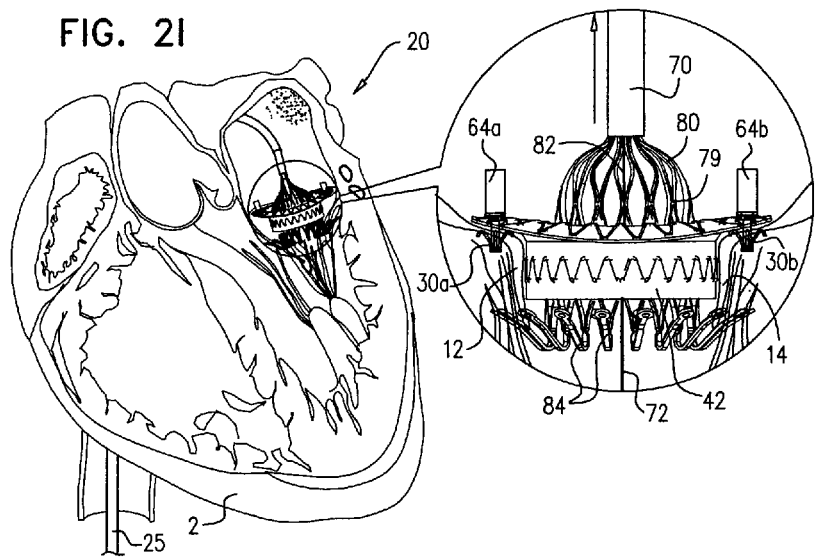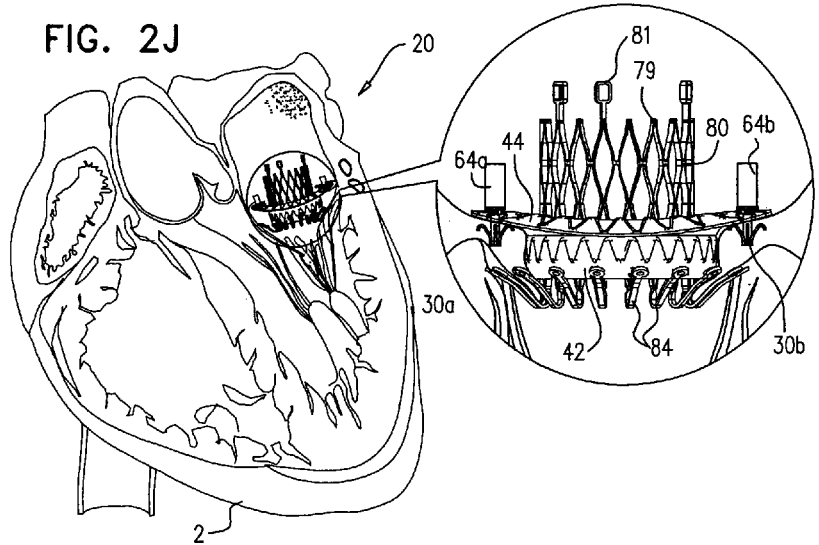

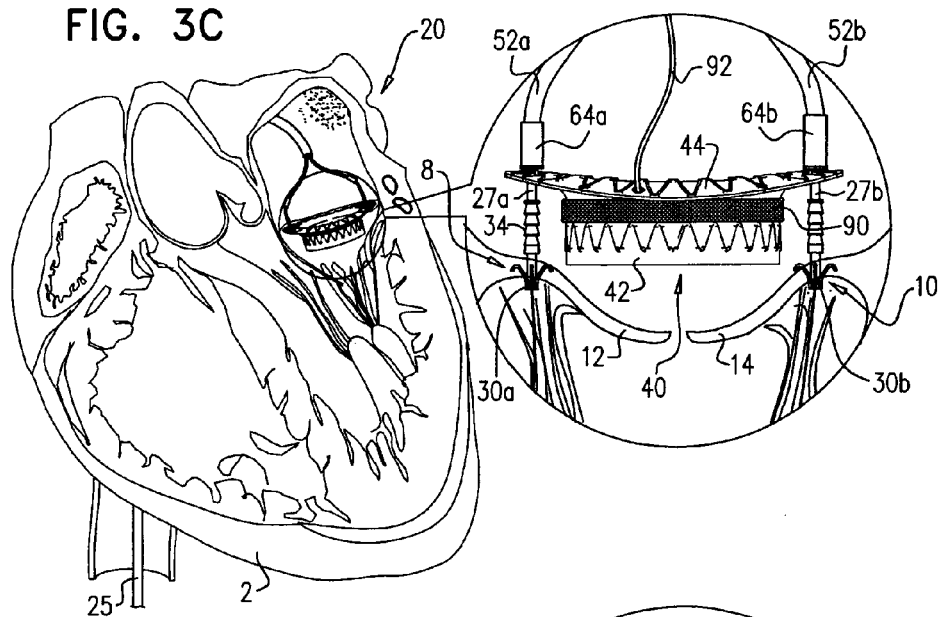
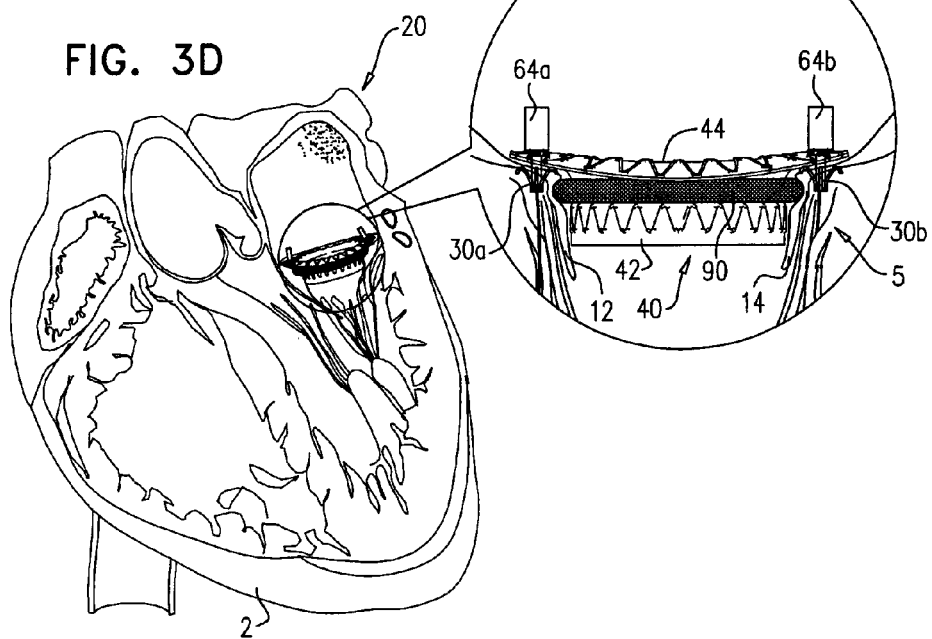

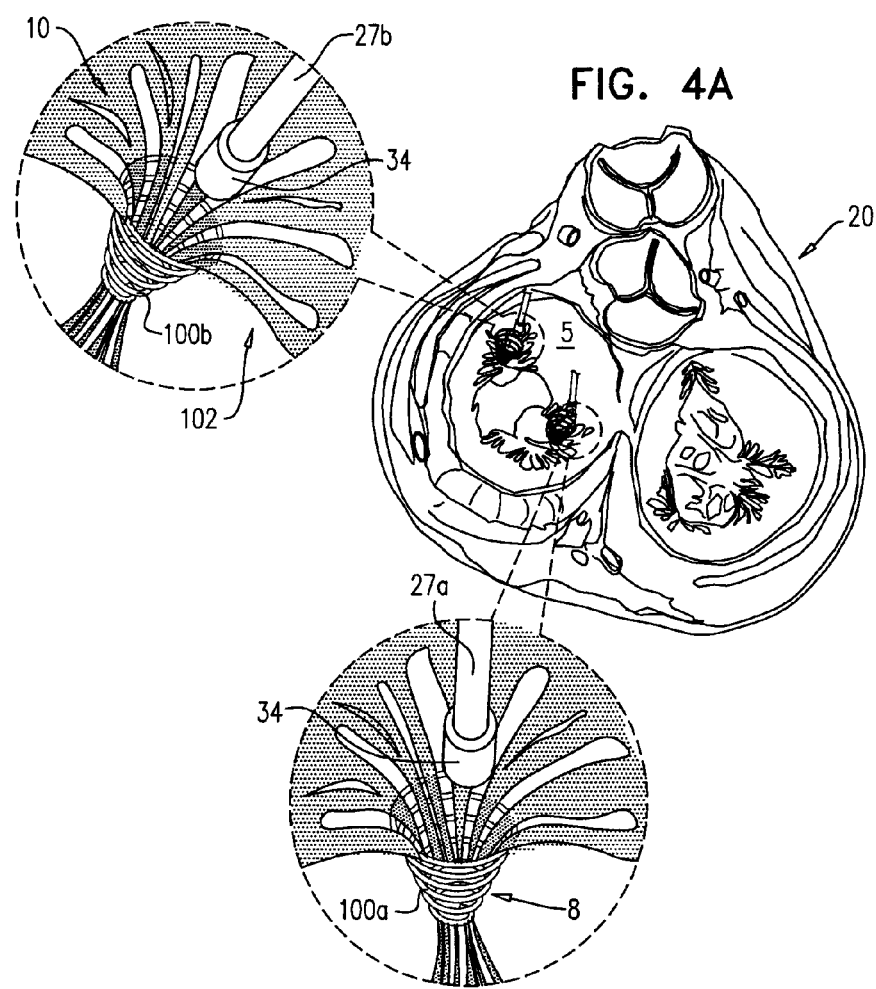

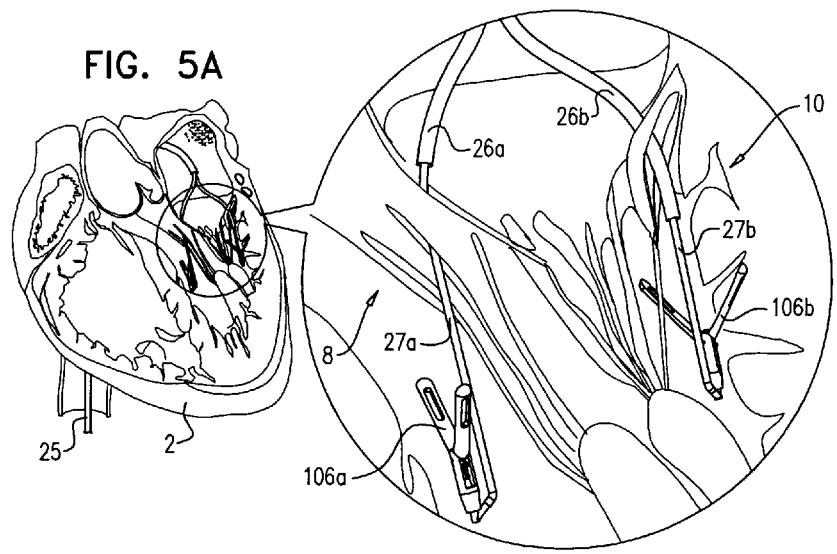
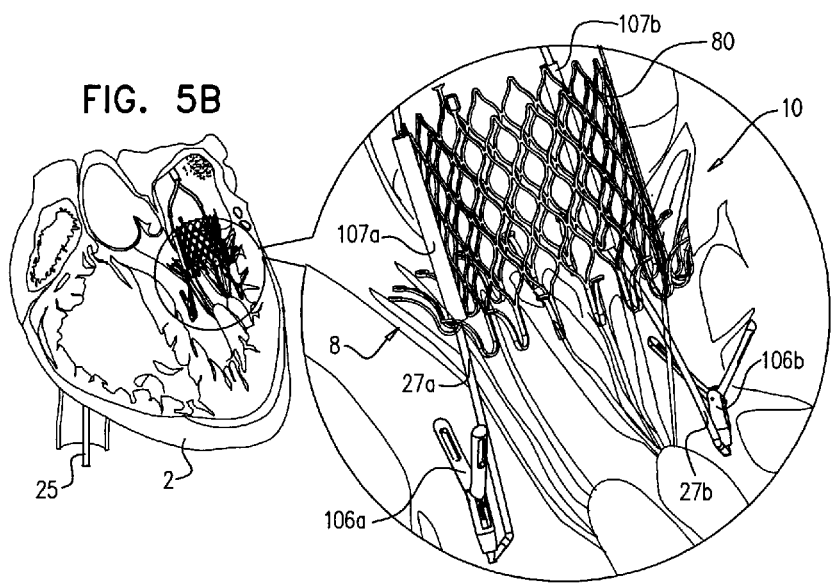

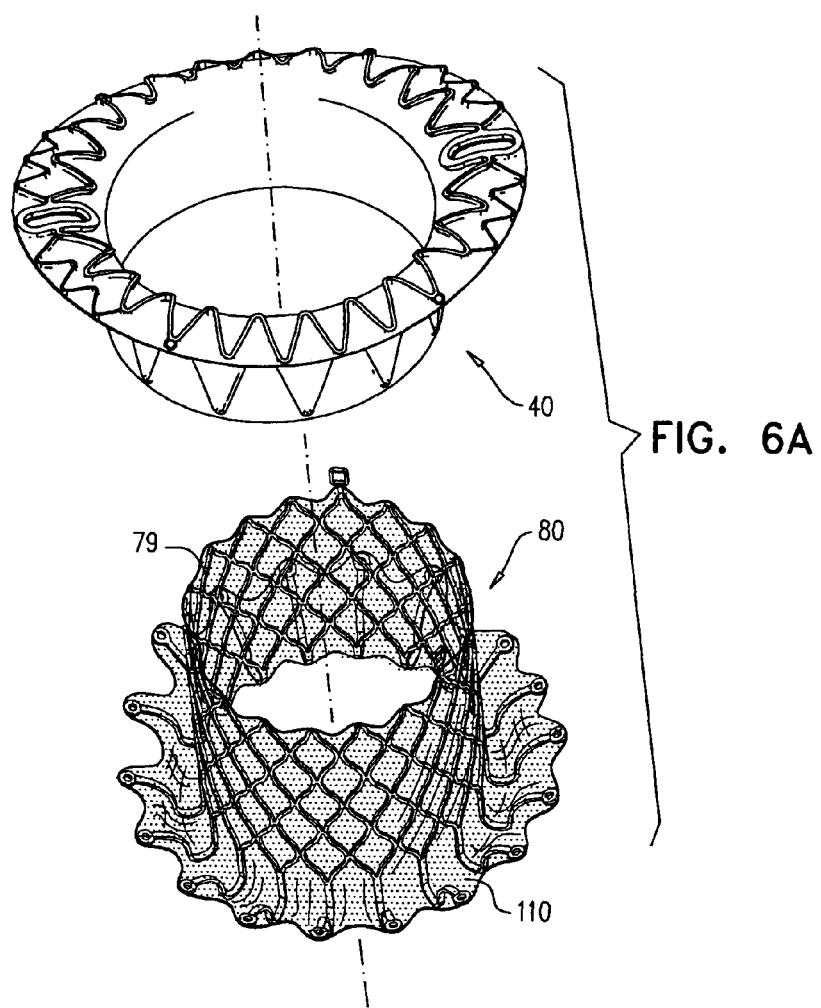

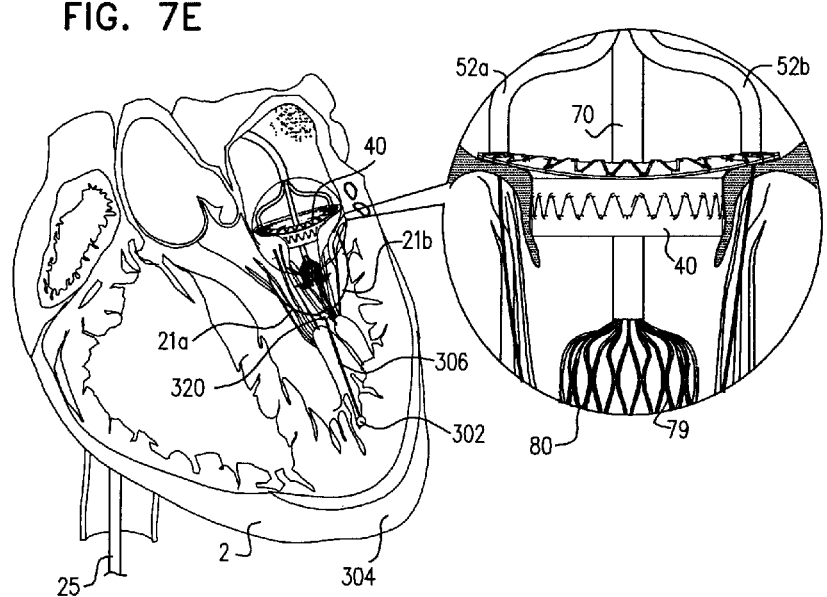
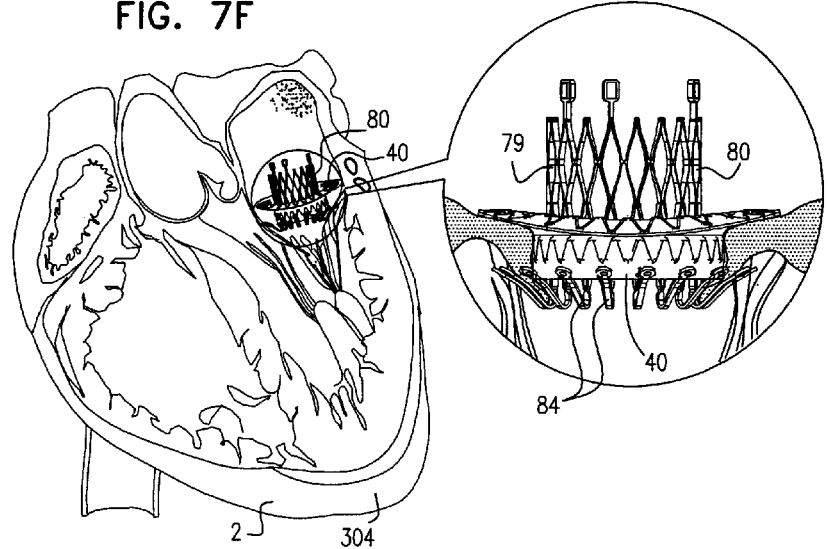

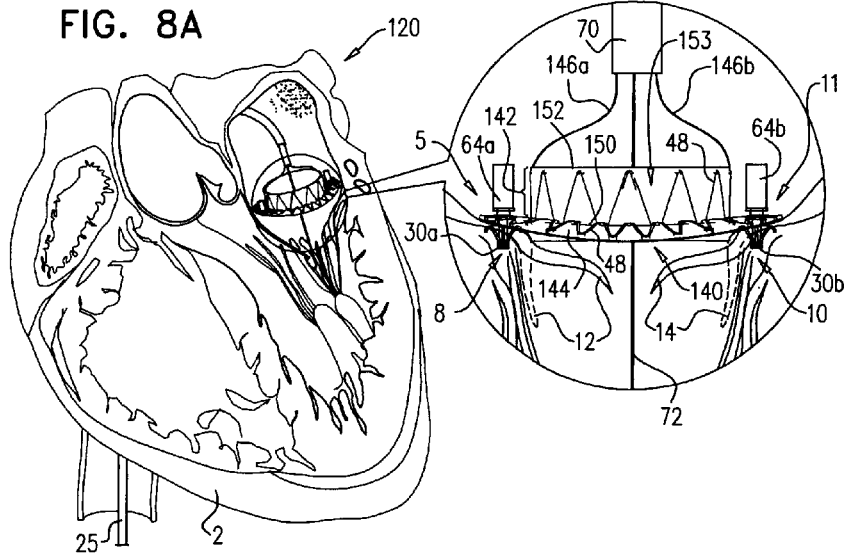
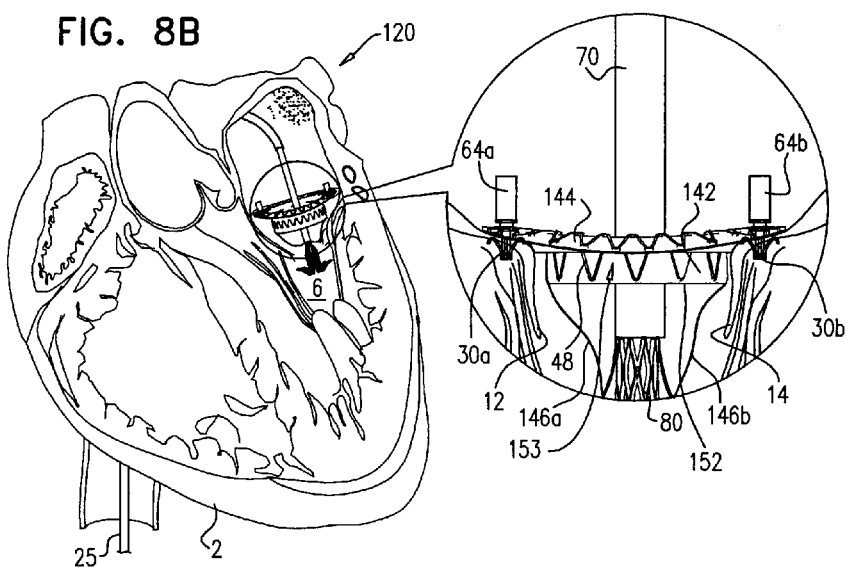

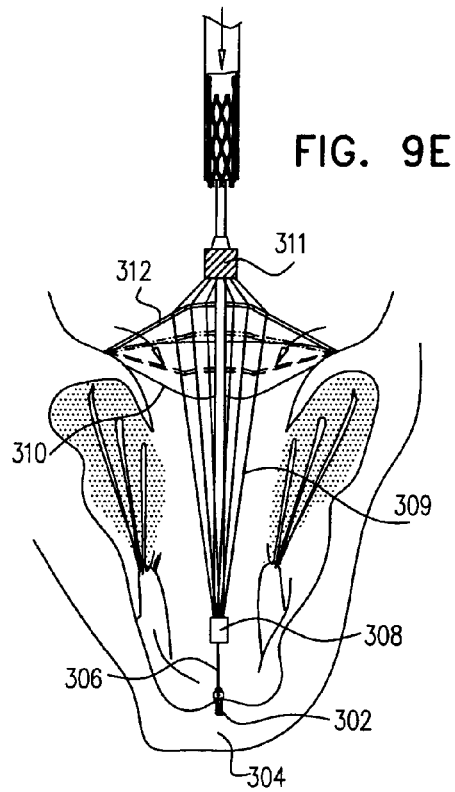
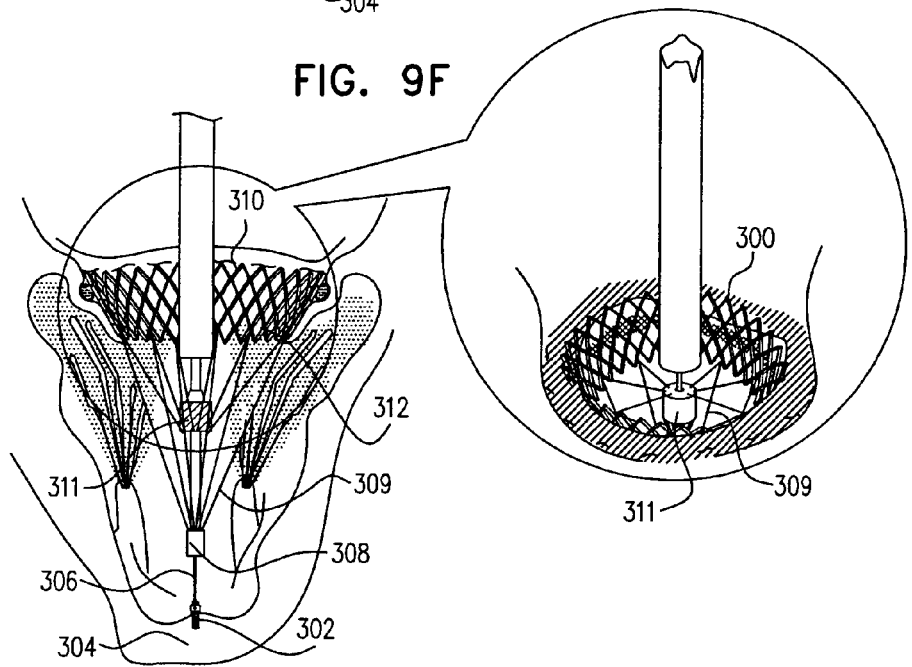

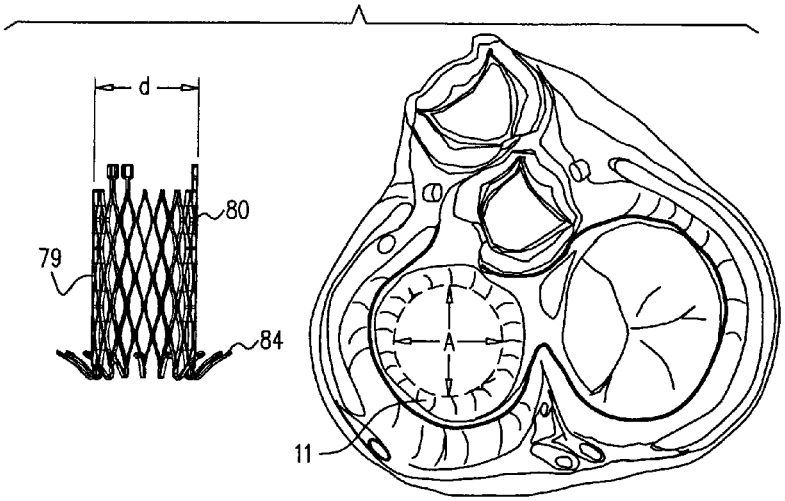
FIG. 10
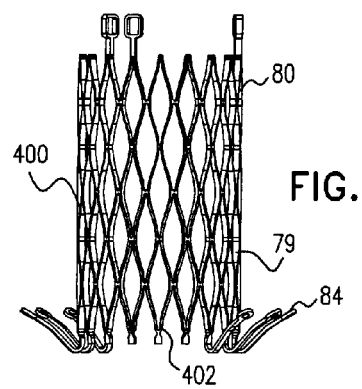
FIG. 11A
FIG. 11B                    FIG. 11C
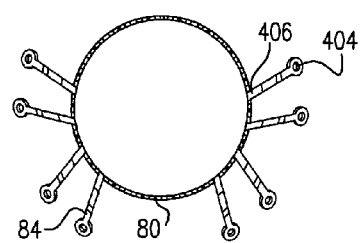        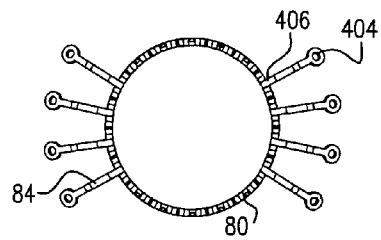

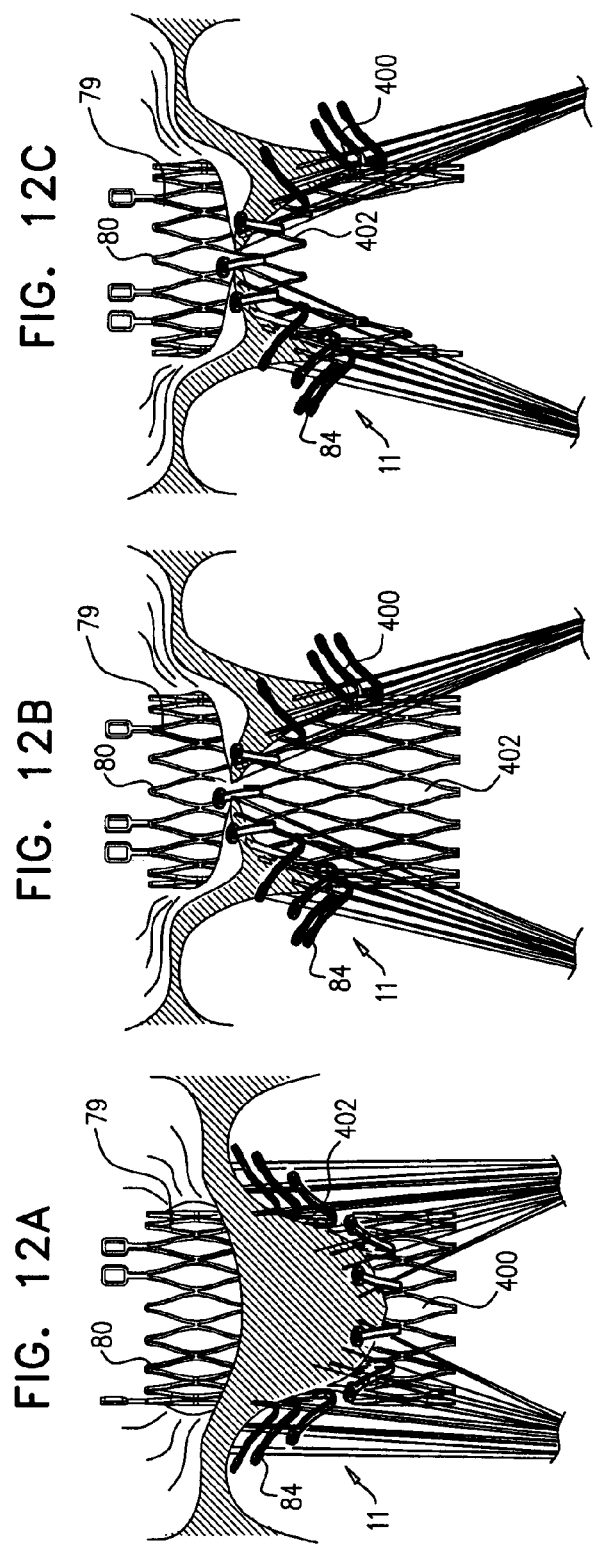

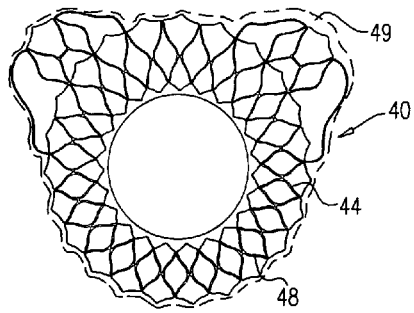
FIG. 14A
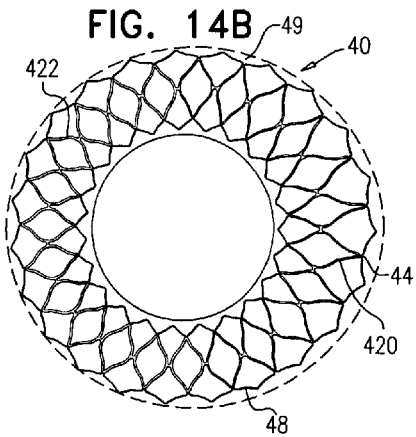
FIG. 14B
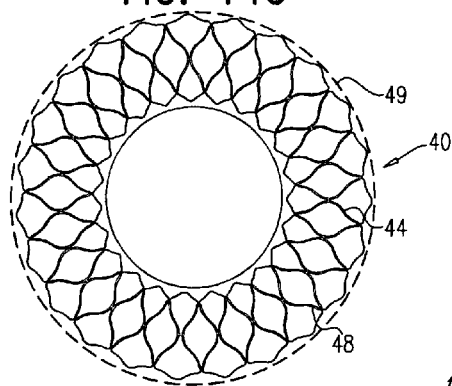
FIG. 14C
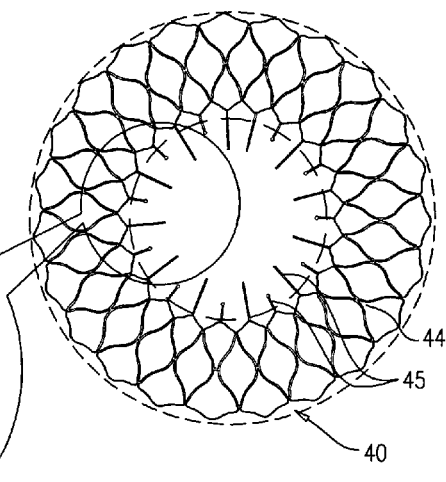
FIG. 14D
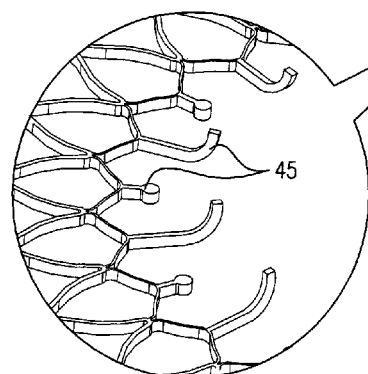

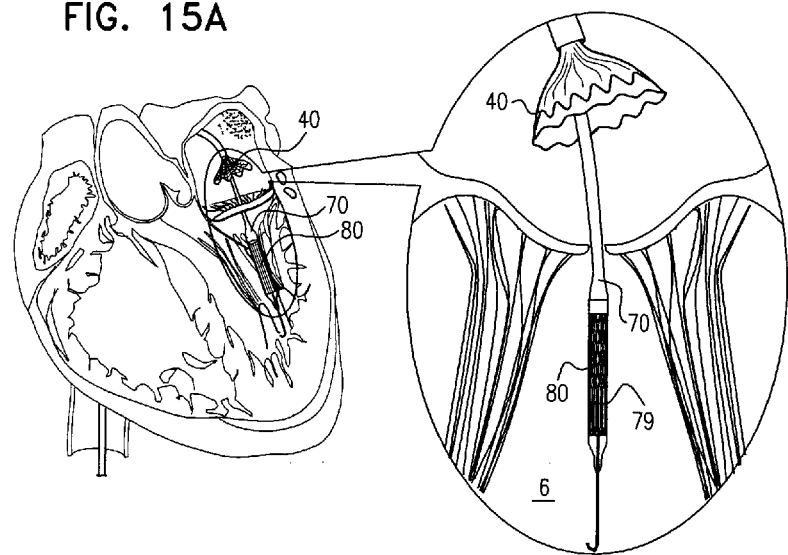
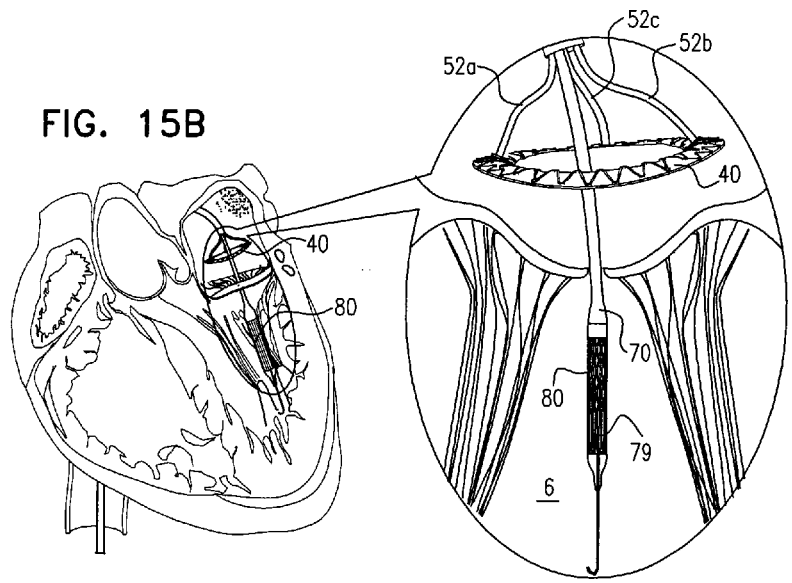

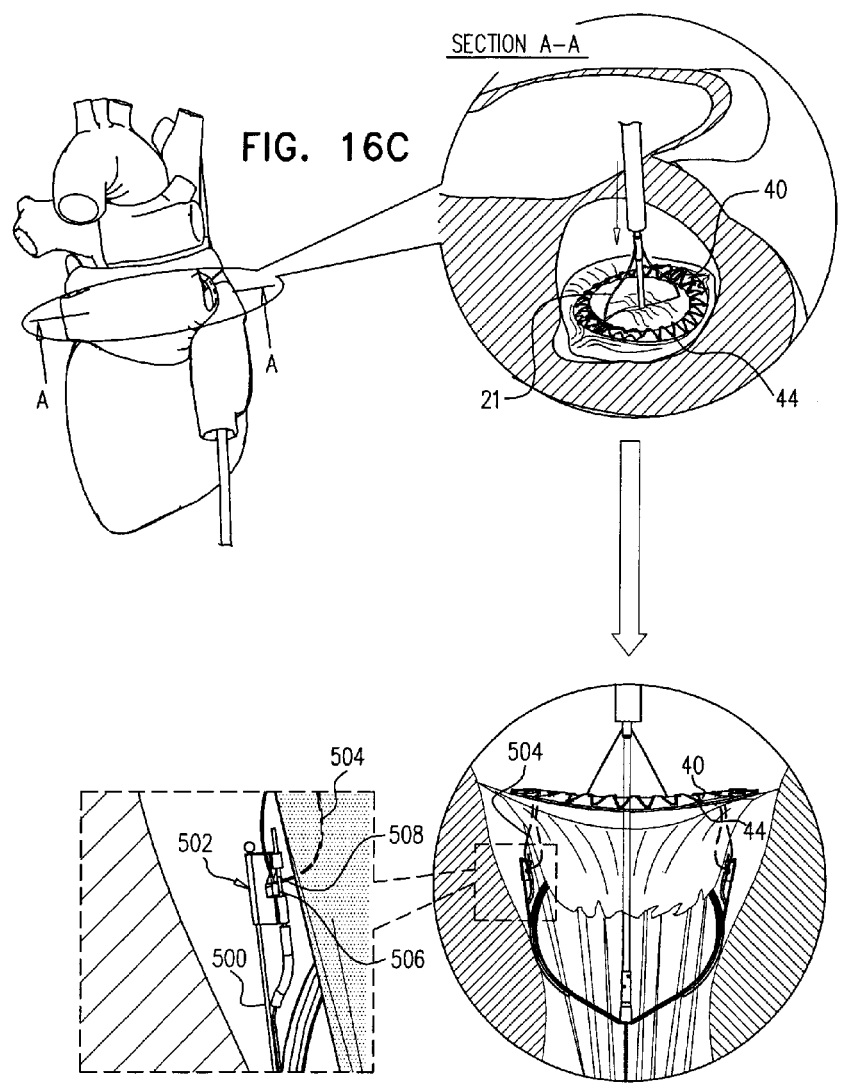

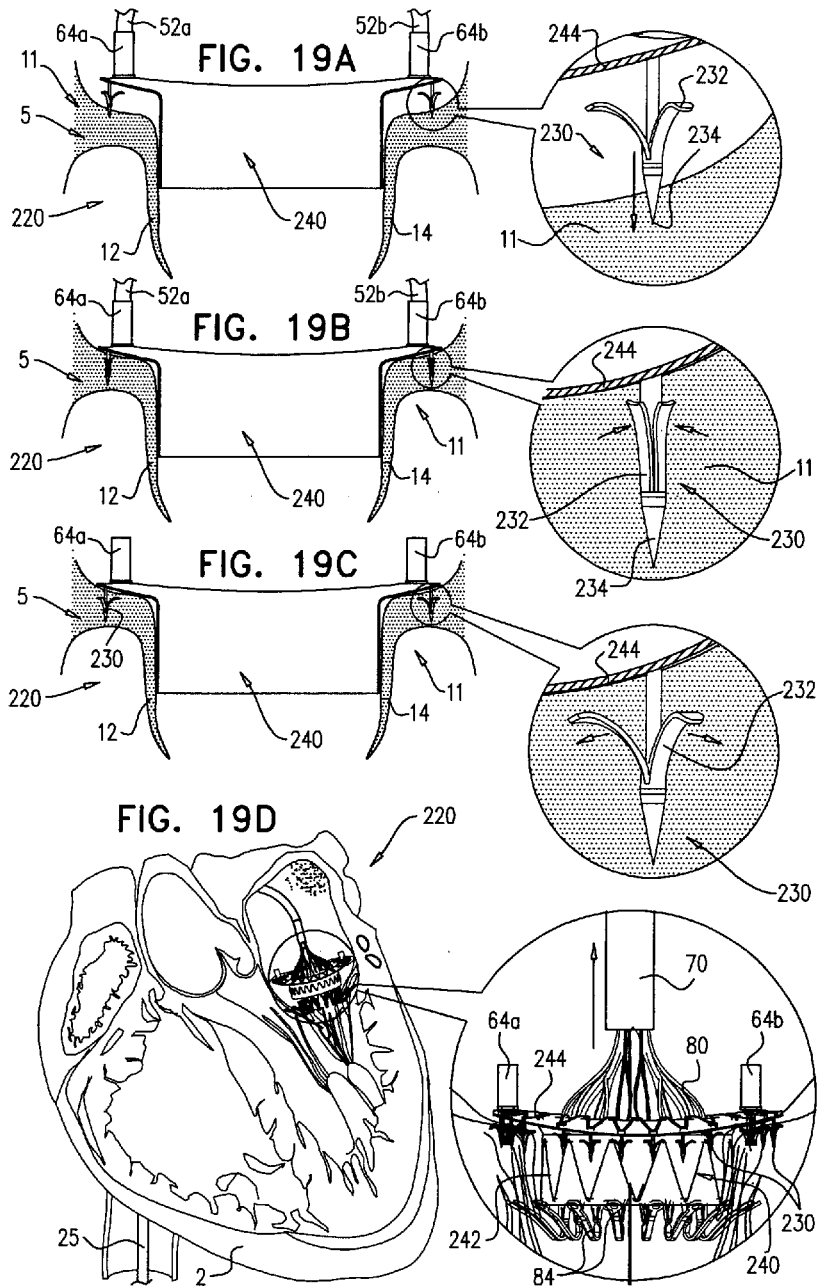

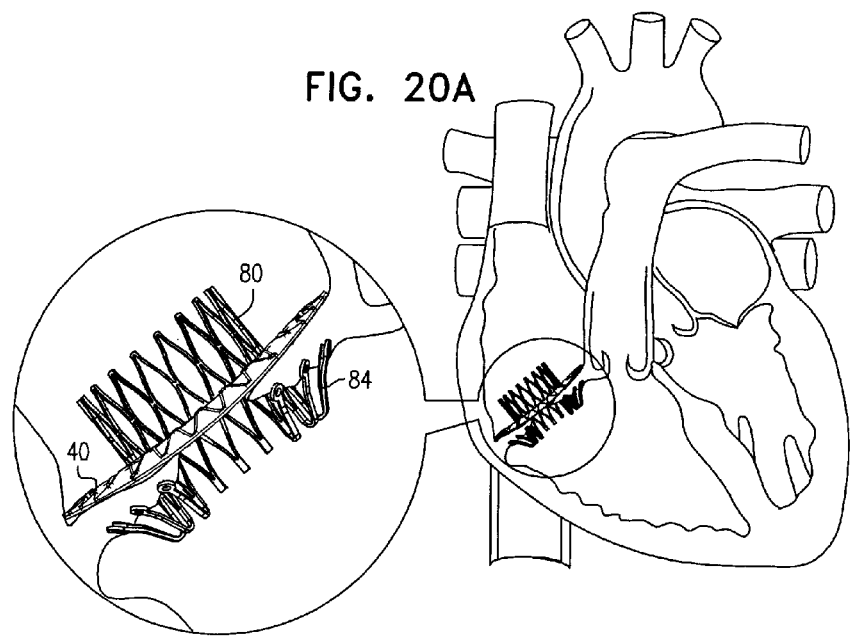
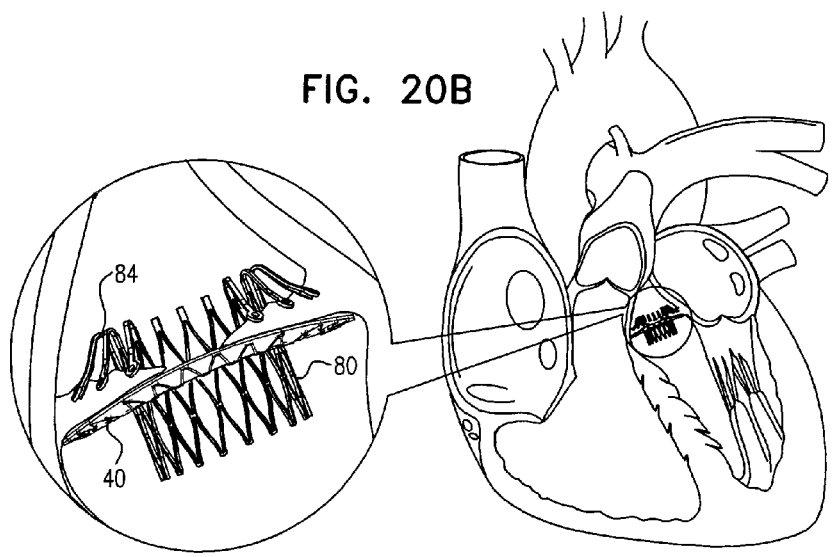

TECHNIQUES FOR PERCUTANEOUS MITRAL VALVE REPLACEMENT AND SEALING

CROSS-REFERENCES TO RELATED APPLICATIONS

The present application claims priority and is a continuation-in-part of:

(a) U.S. Ser. No. 12/840,463 to Hacohen, filed Jul. 21, 2010, entitled "Guide wires with commissural anchors to advance a prosthetic valve," which published as US 2012/0022639, (b) U.S. Ser. No. 13/033,852 to Gross, filed Feb. 24, 2011, entitled "Techniques for percutaneous mitral valve replacement and sealing," which published as US 2012/0022640, and which is a continuation-in-part of U.S. Ser. No. 12/840,463 to Hacohen; and claims priority from U.S. Provisional Patent Application 61/492,449 to Gross, filed Jun. 2, 2011, entitled, "Techniques for percutaneous mitral valve replacement and sealing."

All of the above-referenced applications are incorporated herein by reference.

FIELD OF THE INVENTION

Embodiments of the present invention relate in general to valve replacement. More specifically, embodiments of the present invention relate to prosthetic valves for replacement of an atrioventricular valve.

BACKGROUND

Dilation of the annulus of the mitral valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium. Dilation of the annulus is sometimes treated by implanting a prosthetic mitral valve at a patient's native mitral valve.

SUMMARY

For some applications of the present invention, one or more guide members (e.g., wires, sutures, or strings) is configured to be anchored to respective commissures of a native atrioventricular valve of a patient, and each guide member facilitates the advancement therealong of respective commissural anchors. The commissural anchors are shaped so as to define a plurality of barbs or prongs which are expandable to restrict proximal movement of the anchors following their deployment. The guide members facilitate advancement of a collapsible prosthetic valve support (e.g., a skirt) which serves as a base for and receives a collapsible prosthetic mitral valve which is subsequently coupled to the support. The support comprises a proximal annular element, or ring, and a distal cylindrical element. The cylindrical element is configured to push aside and press against the native leaflets of the native valve, and the proximal annular element is shaped so as to define one or more holes for sliding the valve support along the one or more guide members. The proximal annular element is configured to be positioned along the annulus of the native valve.

The collapsible prosthetic valve is configured for implantation in and/or at least partial replacement (e.g., full replacement) of the native atrioventricular valve of the patient, such as a native mitral valve or a native tricuspid valve. The valve support and the prosthetic valve are configured to assume collapsed states for minimally-invasive delivery to the diseased native valve, such as by percutaneous or transluminal delivery using one or more catheters. For some applications, the valve support and the prosthetic valve are implanted during an open-heart procedure.

The prosthetic valve support is shaped so as to define a downstream skirt. The downstream skirt is configured to be placed at native valve, such that the downstream skirt passes through the orifice of the native valve and extends toward, and, typically partially into, a ventricle. The downstream skirt typically additionally pushes aside and presses against the native leaflets of the native valve, which are left in place during and after implantation of the prosthetic valve support and/or the prosthetic valve.

The proximal annular element has upper and lower surfaces. For some applications of the present invention, one or more, e.g., a plurality of, tissue anchors are coupled to the lower surface and facilitate anchoring of the proximal annular element to the annulus of the native valve. For some applications, the one or more anchors comprise at least first and second commissural anchors that are configured to be implanted at or in the vicinity of the commissures of the native valve.

The cylindrical element of the valve support has first and second ends and a cylindrical body disposed between the first and second ends. The first end of the cylindrical element is coupled to the annular element while the second end defines a free end of the cylindrical element. For some applications of the present invention, the cylindrical element of the valve support is invertible such that (1) during a first period, the second end and the cylindrical body of the cylindrical element are disposed above the annular element (e.g., in the atrium of the heart), and (2) during a second period, the second end and the cylindrical body of the cylindrical element are disposed below the annular element (e.g., in the ventricle of the heart).

For some applications, techniques are applied to facilitate sealing of the interface between the valve support and the native valve, and/or the interface between the prosthetic valve and the native valve. For example, a sealing balloon may be placed on a valve-facing, lower side of the annular element of the valve support, the sealing balloon being configured to be inflated such that the balloon seals the interface between the valve support and the native valve. Alternatively or additionally, commissural helices are wrapped around chordae tendineae of the patient in order to facilitate sealing of the valve commissures around the valve support and/or around the valve. Further alternatively or additionally, the valve commissures are grasped by grasping elements that act in order to facilitate sealing of the commissures around the valve support and/or around the valve. For some applications, one or more of the aforementioned sealing elements facilitates anchoring of the prosthetic valve to the native valve in addition to facilitating sealing.

For some applications, the prosthetic valve comprises an expandable frame (e.g., a wire frame), and a sealing material (such as latex) is disposed on the outer surface of the frame so as to form webbing between at least some of the struts of the wire frame, and to provide sealing between the wire frame and the native valve.

For some applications, an invertible prosthetic valve support is used to support a prosthetic valve. Typically, a sealing element is disposed circumferentially around a surface of the invertible prosthetic valve support that is initially an inner surface of the invertible prosthetic valve support. The invertible prosthetic valve support is anchored to the native valve, and is subsequently inverted. Subsequent to the inversion of the invertible prosthetic valve support, the sealing element is disposed on the outer surface of the invertible prosthetic valve support and acts to seal the interface between the outer surface and the native valve.

There is therefore provided, in accordance with some applications of the present invention, apparatus, including:

a prosthetic valve support configured to be placed at an annulus of a native atrioventricular valve of a patient, the prosthetic valve support defining an annular element that defines an inner cross-sectional area thereof;

an expandable prosthetic valve configured to be placed into a ventricle of the patient, the prosthetic valve including:

an expandable frame; and prosthetic valve leaflets coupled to the expandable frame;

the expandable frame of the prosthetic valve being configured such that when the frame is in a non-constrained state thereof, a cross-sectional area of the frame, along at least a given portion of a length of the frame, is greater than the cross-sectional area defined by the annular element of the prosthetic valve support, the prosthetic valve thereby being couplable to the prosthetic valve support at any location along the portion, responsively to radial forces acted upon the valve support by the expandable frame, by the expandable frame being expanded when the location along the portion is aligned with the annular element of the prosthetic valve support.

For some applications, the valve support is collapsible for transcatheter delivery.

For some applications, the native atrioventricular valve includes a mitral valve, and the prosthetic valve includes three prosthetic leaflets.

For some applications, the annular element of the valve support is asymmetrically shaped.

For some applications, the annular element is shaped to define a hole, and a center of the hole is disposed asymmetrically with respect to an outer perimeter of the annular element.

For some applications, the frame includes proximally-facing protrusions at a distal end thereof, the protrusions being configured to prevent proximal migration of the valve into an atrium.

For some applications, the protrusions are disposed at an angle from the frame of more than 40 degrees.

For some applications, the protrusions are disposed at an angle from the frame of less than 80 degrees.

For some applications, a length of each of the protrusions is less than 5 mm.

For some applications, the frame includes a single proximally-facing protrusion corresponding to each native valve leaflet of the valve, each of the protrusions having a width of less than 1 mm.

For some applications, the protrusions are disposed in a sinusoidal configuration such that the protrusions conform with a saddle shape of the patient's native annulus.

For some applications, the protrusions are configured to prevent the native leaflets from interfering with a left ventricular outflow tract of the patient.

For some applications, the frame includes first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the frame, the second set of protrusions being disposed within a second circumferential arc with respect to the longitudinal axis of the prosthetic valve, on a second side of the distal end of the frame, the first and second sets being disposed so as to provide first and second gaps therebetween at the distal end of the frame, at least one of the gaps having a circumferential arc of at least 20 degrees, the apparatus further including one or more valve guide members configured to be delivered to one or more commissures of the native valve, and to guide the valve such that the first and second circumferential arcs are aligned with respective leaflets of the native valve and such that the first and second gaps are aligned with respective commissures of the native valve.

For some applications, the at least one of the gaps has a circumferential arc of at least 60 degrees.

For some applications, the first circumferential arc defines an angle of between 25 degrees and 90 degrees about the longitudinal axis of the prosthetic valve.

For some applications, the second circumferential arc defines an angle of between 25 degrees and 90 degrees about the longitudinal axis of the prosthetic valve.

For some applications, the first circumferential arc defines an angle of between 45 degrees and 75 degrees about the longitudinal axis of the prosthetic valve.

For some applications, the second circumferential arc defines an angle of between 45 degrees and 75 degrees about the longitudinal axis of the prosthetic valve.

For some applications, the expandable frame of the prosthetic valve is configured such that when the frame is in a non-constrained state thereof the frame has a maximum diameter of less than 25 mm.

For some applications, the expandable frame of the prosthetic valve is configured such that when the frame is in a non-constrained state thereof the frame has a maximum diameter of more than 15 mm.

For some applications, the expandable frame of the prosthetic valve is configured such that when the frame is in a non-constrained state thereof the frame has a maximum diameter of less than 20 mm.

For some applications, the expandable frame of the prosthetic valve is configured such that when the frame is in a non-constrained state thereof, a cross-sectional area of the frame at a proximal end of the frame is greater than a cross-sectional area of the frame at a distal end of the frame.

For some applications, the expandable frame of the prosthetic valve is configured such that when the frame is in the non-constrained state thereof the frame defines a frustoconical shape.

For some applications, the expandable frame of the prosthetic valve is configured such that when the frame is in the non-constrained state thereof the frame defines a trumpet shape.

There is further provided, in accordance with some applications of the present invention, a method, including:

placing a prosthetic valve support at an annulus of a native atrioventricular valve of a patient, the prosthetic valve support defining an annular element that defines an inner cross-sectional area thereof;

placing into a ventricle of the patient, an expandable prosthetic valve, the prosthetic valve including an expandable frame, and prosthetic valve leaflets coupled to the expandable frame, the expandable frame of the prosthetic valve being configured such that when the frame is in a non-constrained state thereof, a cross-sectional area of the frame, along at least a given portion of a length of the frame, is greater than the cross-sectional area defined by the annular element of the prosthetic valve support;

determining a location anywhere along the portion at which to couple the expandable valve the prosthetic valve support; and in response thereto, aligning the location along the portion of the expandable frame with the annular element of the prosthetic valve support; and coupling the expandable valve to the prosthetic valve support at the location, responsively to radial forces acted upon the valve support by the expandable frame, by facilitating expansion of the expandable frame, when the location along the portion is aligned with the annular element of the prosthetic valve support.

For some applications, placing the valve support at the annulus includes transcatheterally placing the valve support at the annulus in a collapsed state.

For some applications, the native atrioventricular valve includes a mitral valve, and placing the prosthetic valve into the ventricle includes placing into the ventricle a prosthetic valve that includes three prosthetic leaflets.

For some applications, placing the prosthetic valve support at the annulus includes placing an asymmetrically-shaped prosthetic valve support at the annulus.

For some applications, placing the prosthetic valve support at the annulus includes placing at the annulus an annular element that is shaped to define a hole, a center of the hole being disposed asymmetrically with respect to an outer perimeter of the annular element, the annular element being placed such that a center of the hole is disposed asymmetrically with respect to the annulus.

For some applications, the frame includes proximally-facing protrusions at a distal end thereof, the protrusions being configured to prevent proximal migration of the valve into an atrium, and coupling the expandable valve to the prosthetic valve support includes preventing proximal migration of the valve by coupling the valve to the valve support such that the leaflets are disposed at least partially between the protrusions and the valve support.

For some applications, coupling the expandable valve to the prosthetic valve support includes preventing the native leaflets from interfering with a left ventricular outflow tract of the patient.

For some applications, coupling the expandable valve to the prosthetic valve support includes allowing movement of the leaflets with respect to the frame while preventing the proximal migration of the valve.

For some applications, the frame includes first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the frame, the second set of protrusions being disposed within a second circumferential arc with respect to the longitudinal axis of the prosthetic valve, on a second side of the distal end of the frame, the first and second sets being disposed so as to provide first and second gaps therebetween at the distal end of the frame, at least one of the gaps having a circumferential arc of at least 20 degrees, the method further including guiding the valve such that the first and second circumferential arcs are aligned with respective leaflets of the native valve and such that the first and second gaps are aligned with respective commissures of the native valve.

For some applications, facilitating expansion of the frame includes facilitating expansion of the frame to a maximum diameter of less than 25 mm.

For some applications, facilitating expansion of the frame includes facilitating expansion of the frame to a maximum diameter of more than 15 mm.

For some applications, facilitating expansion of the frame includes facilitating expansion of the frame to a maximum diameter of less than 20 mm.

For some applications, facilitating expansion of the frame includes facilitating expansion of the frame such that a cross-sectional area of the frame at a proximal end of the frame is greater than a cross-sectional area of the frame at a distal end of the frame.

For some applications, facilitating expansion of the frame includes facilitating expansion of the frame such that the frame defines a frustoconical shape.

For some applications, facilitating expansion of the frame includes facilitating expansion of the frame such that the frame defines a trumpet shape.

There is additionally provided, in accordance with some applications of the present invention, a method, including:

determining an indication of an area defined by an annulus of a native atrioventricular valve of a patient;

selecting a prosthetic valve support by determining that the prosthetic valve support defines an annular element that defines an inner cross-sectional area that is less than the area defined by the annulus;

placing the prosthetic valve support at the annulus of the native atrioventricular valve;

placing into a ventricle of the patient, an expandable prosthetic valve, the prosthetic valve including an expandable frame, and prosthetic valve leaflets coupled to the expandable frame;

coupling the expandable valve to the prosthetic valve support at the location, responsively to radial forces acted upon the valve support by the expandable frame, by facilitating expansion of the expandable frame, a cross-sectional area defined by the expandable frame of the prosthetic valve being limited by the cross-sectional area defined by the annular element of the prosthetic valve support, such as to facilitate sealing of the native valve with respect to the prosthetic valve by facilitating closing of leaflets of the native valve around the prosthetic valve, upon deployment of the prosthetic valve.

For some applications, facilitating closing of leaflets of the native valve around the prosthetic valve includes facilitating sealing of the native valve at commissures of the native valve.

For some applications, facilitating closing of leaflets of the native valve around the prosthetic valve includes facilitating closing of the leaflets of the native valve around an outer surface of the expandable frame.

For some applications, placing the valve support at the annulus includes transcatheterally placing the valve support at the annulus in a collapsed state.

For some applications, the native atrioventricular valve includes a mitral valve, and placing the prosthetic valve into the ventricle includes placing into the ventricle a prosthetic valve that includes three prosthetic leaflets.

For some applications, placing the prosthetic valve support at the annulus includes placing an asymmetrically-shaped prosthetic valve support at the annulus.

For some applications, placing the prosthetic valve support at the annulus includes placing at the annulus an annular element that is shaped to define a hole, a center of the hole being disposed asymmetrically with respect to an outer perimeter of the annular element, the annular element being placed such that a center of the hole is disposed asymmetrically with respect to the annulus.

For some applications, the frame includes proximally-facing protrusions at a distal end thereof, the protrusions being configured to prevent proximal migration of the valve into an atrium, and coupling the expandable valve to the prosthetic valve support includes preventing proximal migration of the valve by coupling the valve to the valve support such that the leaflets are disposed at least partially between the protrusions and the valve support.

For some applications, coupling the expandable valve to the prosthetic valve support includes preventing the native leaflets from interfering with a left ventricular outflow tract of the patient.

For some applications, coupling the expandable valve to the prosthetic valve support includes allowing movement of the leaflets with respect to the frame while preventing proximal migration of the valve.

For some applications, the frame includes first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the frame, the second set of protrusions being disposed within a second circumferential arc with respect to the longitudinal axis of the prosthetic valve, on a second side of the distal end of the frame, the first and second sets being disposed so as to provide first and second gaps therebetween at the distal end of the frame, at least one of the gaps having a circumferential arc of at least 20 degrees, the method further including guiding the valve such that the first and second circumferential arcs are aligned with respective leaflets of the native valve and such that the first and second gaps are aligned with respective commissures of the native valve.

For some applications, facilitating expansion of the frame includes facilitating expansion of the frame to a maximum diameter of less than 25 mm.

For some applications, facilitating expansion of the frame includes facilitating expansion of the frame to a maximum diameter of more than 15 mm.

For some applications, facilitating expansion of the frame includes facilitating expansion of the frame to a maximum diameter of less than 20 mm.

For some applications, facilitating expansion of the frame includes facilitating expansion of the frame such that a cross-sectional area of the frame at a proximal end of the frame is greater than a cross-sectional area of the frame at a distal end of the frame.

For some applications, facilitating expansion of the frame includes facilitating expansion of the frame such that the frame defines a frustoconical shape.

For some applications, facilitating expansion of the frame includes facilitating expansion of the frame such that the frame defines a trumpet shape.

There is additionally provided, in accordance with some applications of the present invention, a method, including:

placing a prosthetic valve support at an annulus of a native atrioventricular valve of a patient;

placing a prosthetic valve into a ventricle of the patient, the prosthetic valve including protrusions at a distal end thereof;

ensnaring one or more native leaflets of the native valve of the patient with the protrusions; and coupling the prosthetic valve to the native valve, by sandwiching native leaflets of the native valve between the protrusions and the valve support, by pulling the prosthetic valve proximally with respect to the valve support, and while the native leaflets are sandwiched between the protrusions and the valve support, coupling the prosthetic valve to the valve support, by facilitating radial expansion of the prosthetic valve such that the prosthetic valve is held in place with respect to the valve support responsively to radial forces acted upon the valve support by the prosthetic valve.

There is further provided, in accordance with some applications of the present invention, a method, including:

determining an indication of an area defined by an annulus of a native atrioventricular valve of a patient;

selecting a prosthetic valve to be placed in the native valve by determining that the valve defines a cross-sectional area that is less than 90% of the area defined by the annulus; and deploying the prosthetic valve at the native valve, the selecting of the prosthetic valve facilitating sealing of the native valve with respect to the prosthetic valve by facilitating closing of leaflets of the native valve around the prosthetic valve, upon deployment of the prosthetic valve.

For some applications, selecting the prosthetic valve includes selecting a prosthetic valve having a material disposed on an outer surface thereof.

For some applications, selecting the prosthetic valve includes selecting a prosthetic valve having a material that prevents tissue growth disposed on an outer surface thereof.

For some applications, selecting the prosthetic valve includes selecting a prosthetic valve having a material that promotes tissue growth disposed on an outer surface thereof.

For some applications, selecting the prosthetic valve to be placed in the native valve includes determining that the valve defines a cross-sectional area that is less than 80% of the area defined by the annulus.

For some applications, selecting the prosthetic valve to be placed in the native valve includes determining that the valve defines a cross-sectional area that is less than 60% of the area defined by the annulus.

There is further provided, in accordance with some applications of the present invention, apparatus, including:

one or more valve support guide members configured to be delivered to one or more commissures of a native atrioventricular valve of a patient;

one or more valve support anchors configured to be anchored to the one or more commissures of the native valve;

a prosthetic valve support advanceable toward the native valve along the one or more valve support guide members and anchored to the native valve at atgg least the one or more commissures; and a prosthetic valve configured to be coupled to the valve support.

For some applications, the valve support is collapsible for transcatheter delivery and expandable to contact the native atrioventricular valve.

For some applications, the one or more valve support anchors are configured to be anchored to the one or more commissures from ventricular surfaces thereof.

For some applications, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some applications, the one or more valve support anchors includes first and second tissue anchors, the first and second tissue anchors being configured to be anchored to respective first and second commissures of the atrioventricular valve of the patient.

For some applications:

the one or more valve support anchors each include one or more radially-expandable prongs, and the one or more prongs are disposed within a sheath in a compressed state prior to the anchoring, and exposed from within the sheath in order to expand and facilitate anchoring of the valve support anchor to the respective commissures.

For some applications, the prosthetic valve includes two or more prosthetic leaflets.

For some applications, the native atrioventricular valve includes a mitral valve, and the prosthetic valve includes three prosthetic leaflets.

For some applications, the valve support guide members are removable from the patient following the anchoring of the prosthetic valve support at the atrioventricular valve.

For some applications, the valve support is shaped so as to define a distal portion which is configured to push aside, at least in part, native leaflets of the valve of the patient.

For some applications, the one or more valve support anchors are advanceable along the one or more valve support guide members.

For some applications, the valve support is shaped so as to define one or more holes, the one or more holes being configured to facilitate slidable passage therethrough of a respective one of the one or more valve support guide members.

For some applications, the prosthetic valve is shaped so as to define one or more snares configured to ensnare one or more native leaflets of the native valve of the patient.

For some applications, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

For some applications, the apparatus includes one or more delivery lumens, and:

each one of the one or more valve support anchors is removably coupled to a distal end of a respective delivery lumen, the delivery lumen is configured to facilitate advancement of the one or more anchors along the one or more guide members, and the delivery lumen is decoupled from the anchor following the anchoring of the anchor to the one or more commissures.

For some applications, the one or more valve support guide members are removable from the body of the patient following the advancement of the one or more anchors along the one or more guide members.

For some applications:

the valve support is shaped so as to define one or more holes, the one or more holes are configured to facilitate slidable passage therethrough of a respective one of the one or more delivery lumens, and the one or more delivery lumens are decoupleable from the respective valve support anchor following the anchoring of the valve support to at least the one or more commissures.

For some applications, the one or more delivery lumens are removable from the body of the patient following the anchoring of the valve support to at least the one or more commissures.

For some applications, the valve support includes an annular element and a generally cylindrical element coupled to the annular element, the generally cylindrical element being configured to push aside native leaflets of the native valve, the cylindrical element has first and second ends and a cylindrical body that is disposed between the first and second ends.

For some applications, the apparatus includes one or more annular element tissue anchors, the annular element has an upper surface and a lower surface, and the lower surface is coupled to the one or more annular element tissue anchors, the one or more annular element tissue anchors being configured to puncture tissue of a native annulus of the native valve of the patient.

For some applications, one or more annular element tissue anchors includes a plurality of annular element tissue anchors positioned around the lower surface of the annular element.

For some applications, the one or more annular element tissue anchors includes a first commissural anchor configured to puncture tissue of the native valve at a first commissure thereof, and a second commissural anchor configured to puncture tissue of the native valve at a second commissure thereof.

For some applications, each anchor of the one or more annular element tissue anchors includes a distal pointed tip and one or more radially-expandable prongs, the prongs being configured to expand and facilitate anchoring of the anchor and restrict proximal motion of the annular element tissue anchor.

For some applications, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some applications:

the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some applications:

during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end and the body of the cylindrical element into the ventricle to invert the cylindrical element.

There is further provided, in accordance with some applications of the present invention, a method, including:

advancing one or more valve support guide members toward one or more commissures of a native atrioventricular valve of a patient;

advancing along the one or more valve support guide members one or more valve support tissue anchors toward the one or more commissures;

anchoring the one or more valve support tissue anchors to the one or more commissures;

anchoring a prosthetic valve support at the native atrioventricular valve by anchoring the prosthetic valve support at at least the one or more commissures; and coupling a prosthetic valve to the prosthetic valve support.

For some applications, the method includes removing the one or more valve support guide members following the anchoring of the prosthetic valve support at the native atrioventricular valve.

For some applications, advancing the one or more valve support guide members toward the one or more commissures includes advancing one guide member and looping the one guide member through first and second commissures of the native atrioventricular valve in a manner in which a looped portion of the guide member is disposed in a ventricle of the patient and first and second free ends of the guide member are accessible from a site outside a body of the patient.

For some applications, anchoring the one or more valve support anchors includes anchoring the one or more valve support anchors to ventricular surface of the respective commissures of the native valve.

For some applications, anchoring the one or more valve support anchors includes anchoring first and second tissue anchors to respective first and second commissures of the native valve.

For some applications:

advancing along the one or more valve support guide members the one or more valve support tissue anchors includes advancing the one or more valve support tissue anchors within a sheath, and anchoring the one or more valve support tissue anchors includes exposing the one or more valve support anchors from within the sheath and facilitating radial expansion of one or more radially-expandable prongs of the one or more anchors.

For some applications, coupling the prosthetic valve to the prosthetic valve support includes coupling a prosthetic valve having two or more leaflets.

For some applications, the native atrioventricular valve includes a mitral valve of the patient, and coupling the prosthetic valve to the prosthetic valve support includes coupling a prosthetic valve having three leaflets.

For some applications, anchoring the prosthetic valve support includes pushing aside, at least in part, native leaflets of the valve of the patient by at least a portion of the support.

For some applications, the prosthetic valve support is coupled to one or more annulus tissue anchors, and anchoring the prosthetic valve support includes pushing the one or more annulus tissue anchors into tissue of an annulus of the native valve.

For some applications, coupling the prosthetic valve to the prosthetic valve support includes ensnaring one or more native leaflets of the native valve of the patient by a portion of the prosthetic valve.

For some applications, the one or more valve support anchors includes one or more ventricular anchors, and the method further includes advancing one or more atrial anchors to an atrial surface of the valve support, and anchoring in place the valve support in a vicinity of a respective one of the ventricular anchors.

For some applications, the method includes advancing the valve support along the one or more valve support guide members prior to the anchoring of the valve support.

For some applications, the valve support is shaped so as to define one or more holes, and advancing the valve support along the one or more valve support guide members includes threading the one or more valve support guide members through the one or more holes of the valve support and sliding the valve support along the one or more guide members.

For some applications, the method includes removing the one or more valve support guide members from a body of the patient following the anchoring of the valve support.

For some applications, the valve support includes:

an annular element, and a generally cylindrical element having first and second ends and a cylindrical body that is disposed between the first and second ends, the first end being coupled to the annular element; and anchoring of the valve support, including anchoring the valve support in a manner in which:

the annular element is positioned along an annulus of the native valve, the second end of the cylindrical element is disposed above the annular element in an atrium of a heart of the patient, and the body of the cylindrical element is disposed above the annular element.

For some applications, the method includes, following the anchoring, inverting the cylindrical element to pull the second end of the cylindrical element below the annular element and into a ventricle of the heart, in a manner in which the body of the cylindrical element is disposed below the annular element and pushes aside one or more native leaflets of the valve of the patient.

For some applications:

inverting the cylindrical element includes advancing the prosthetic valve along one or more prosthetic valve guide members reversibly coupled to the cylindrical element in a vicinity of the second end thereof, advancing the prosthetic valve includes advancing the prosthetic valve into the ventricle to pull the prosthetic valve guide members and the second end of the cylindrical element into the ventricle, and the method further includes following the advancing of the prosthetic valve into the ventricle, pulling proximally the prosthetic valve such that a proximal portion of the valve contacts the valve support.

For some applications, pulling the prosthetic valve proximally includes ensnaring the one or more leaflets of the valve by a portion of the prosthetic valve.

For some applications, advancing the one or more valve support anchors includes:

providing a respective delivery lumen coupled at a distal end thereof to each one of the one or more anchors, advancing each delivery lumen along a respective one of the one or more valve support guide members, facilitating anchoring of each one of the one or more anchors to the one or more commissures by the respective delivery lumen, and decoupling the delivery lumen from each one of the one or more valve support anchors following the anchoring of the one or more valve support anchors.

For some applications, the method includes removing the one or more valve support guide members from a body of the patient following the anchoring of each one of the one or more valve support anchors to the one or more commissures.

For some applications, the method includes advancing the prosthetic valve support along the one or more delivery lumens prior to the anchoring the support at the native atrioventricular valve.

For some applications, the valve support is shaped so as to define one or more holes, and advancing the valve support along the one or more delivery lumens includes threading the one or more delivery lumens through the one or more holes of the valve support and sliding the valve support along the one or more delivery lumens.

For some applications, the method includes removing the one or more delivery lumens from a body of the patient following the anchoring the support at the atrioventricular valve.

There is additionally provided, in accordance with some applications of the present invention, apparatus including a valve support for receiving a prosthetic valve, the valve support including:

an annular element configured to be positioned along a native annulus of a native atrioventricular valve of a patient; and a flexible generally cylindrical element configured to be positioned in the native atrioventricular valve of the patient and to push aside native leaflets of the native valve, the cylindrical element having first and second ends and a cylindrical body that is disposed between the first and second ends, and:

the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some applications, the cylindrical element includes a flexible wireframe covered by a fabric.

For some applications, the valve support is collapsible for transcatheter delivery and expandable to contact the native atrioventricular valve.

For some applications, the annular element has an upper surface and a lower surface, the lower surface is coupled to one or more annular element tissue anchors configured to puncture tissue of the native annulus of the patient.

For some applications, the one or more annular element tissue anchors includes a plurality of annular element tissue anchors positioned around the lower surface of the annular element.

For some applications, the one or more annular element tissue anchors includes a first commissural annular element tissue anchor configured to puncture tissue of the native valve at a first commissure thereof, and a second commissural annular element tissue anchor configured to puncture tissue of the native valve at a second commissure thereof.

For some applications, each anchor of the one or more annular element tissue anchors includes a distal pointed tip and one or more radially-expandable prongs, the prongs being configured to expand and facilitate anchoring of the anchor and restrict proximal motion of the annular element tissue anchor.

For some applications, the apparatus includes one or more valve support guide members configured to be delivered to one or more commissures of the native atrioventricular valve of the patient, the one or more valve support guide members are configured to facilitate advancement of the valve support toward the native valve.

For some applications, the valve support is shaped so as to define one or more holes, the one or more holes configured to facilitate slidable passage therethrough of a respective one of the one or more valve support guide members.

For some applications, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some applications, the apparatus includes one or more valve support tissue anchors configured to be advanceable along the one or more valve support guide members and anchored to the one or more commissures of the valve.

For some applications, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

For some applications, the valve support guide members are removable from the patient following the anchoring of the valve support at the atrioventricular valve.

For some applications, the one or more valve support anchors are configured to be anchored to the one or more commissures from ventricular surfaces thereof prior to advancement of the valve support.

For some applications, the one or more valve support tissue anchors includes first and second valve support tissue anchors, the first and second valve support tissue anchors being configured to be anchored to respective first and second commissures of the atrioventricular valve of the patient.

For some applications:

the one or more valve support tissue anchors each include one or more radially-expandable prongs, and the one or more prongs are disposed within a sheath in a compressed state prior to the anchoring and exposed from within the sheath in order to expand and facilitate anchoring of the anchor to the respective commissures.

For some applications, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some applications, the apparatus includes the prosthetic valve, and the prosthetic valve is couplable to the valve support.

For some applications:

during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end of the cylindrical element into the ventricle to invert the cylindrical element.

For some applications, the prosthetic valve is collapsible for transcatheter delivery and expandable when exposed from within a delivery catheter.

For some applications, the prosthetic valve includes two or more prosthetic leaflets.

For some applications, the native atrioventricular valve includes a mitral valve, and the prosthetic valve includes three prosthetic leaflets.

For some applications, the prosthetic valve guide members are removable from the patient following the anchoring of the prosthetic valve at the atrioventricular valve.

For some applications, the prosthetic valve is shaped so as to define one or more snares configured to ensnare one or more native leaflets of the native valve of the patient.

There is yet additionally provided, in accordance with some applications of the present invention, a method, including:

advancing toward a native atrioventricular valve of a heart of a patient, a valve support including:
    an annular element, and
    a generally cylindrical element having first and second ends and a cylindrical body that is disposed between the first and second ends, the first end being coupled to the annular element;

anchoring the annular element to an annulus of the native atrioventricular valve, following the anchoring, the second end of the cylindrical element is disposed above the annular element in an atrium of the heart, in a manner in which the body of the cylindrical element is disposed above the annular element; and following the anchoring, inverting the cylindrical element to pull the second end of the cylindrical element below the annular element and into a ventricle of the heart, in a manner in which the body of the cylindrical element is disposed below the annular element and pushes aside one or more native leaflets of the valve of the patient.

For some applications, anchoring the annular element to the annulus of the native atrioventricular valve includes:

advancing one or more valve support anchors that are distinct from the valve support toward one or more commissures of the heart, and anchoring the annular element to the annulus using the one or more positioning anchors.

For some applications, the annular element is coupled to one or more annular element tissue anchors, and anchoring the annular element includes pushing the one or more annular element tissue anchors into tissue of the annulus.

For some applications:

inverting the cylindrical element includes advancing a prosthetic valve along one or more valve guide members reversibly coupled to the cylindrical element in a vicinity of the second end thereof, advancing the prosthetic valve includes advancing the prosthetic valve into the ventricle to pull the guide members and the second end of the cylindrical element into the ventricle, and the method further includes following the advancing of the prosthetic valve into the ventricle, pulling proximally the prosthetic valve such that a proximal portion of the valve contacts the valve support.

For some applications, pulling the prosthetic valve proximally includes ensnaring the one or more leaflets of the valve by a portion of the prosthetic valve.

There is also provided, in accordance with some applications of the present invention, apparatus including a valve support for receiving a prosthetic valve, the valve support including:

an annular element configured to be positioned along a native annulus of a native atrioventricular valve of a patient, the annular element having upper and lower surfaces; and one or more annular element tissue anchors coupled to the lower surface of the annular element, the one or more annular element tissue anchors being configured to puncture tissue of the native annulus of the patient.

For some applications, the valve support is collapsible for transcatheter delivery and expandable to contact the native atrioventricular valve.

For some applications, the one or more annular element tissue anchors includes a plurality of annular element tissue anchors positioned around the lower surface of the annular element.

For some applications, the one or more annular element tissue anchors includes a first commissural annular element tissue anchor configured to puncture tissue of the native valve at a first commissure thereof, and a second commissural annular element tissue anchor configured to puncture tissue of the native valve at a second commissure thereof.

For some applications, each anchor of the one or more annular element tissue anchors includes a distal pointed tip and one or more radially-expandable prongs, the prongs being configured to expand and facilitate anchoring of the anchor and restrict proximal motion of the anchor.

For some applications, the apparatus includes one or more valve support guide members configured to be delivered to one or more commissures of the native atrioventricular valve of the patient, the one or more valve support guide members are configured to facilitate advancement of the valve support toward the native valve.

For some applications, the valve support is shaped so as to define one or more holes, the one or more holes configured to facilitate slidable passage therethrough of a respective one of the one or more valve support guide members.

For some applications, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some applications, the apparatus includes one or more valve support tissue anchors that are distinct from the valve support and are configured to be advanceable along the one or more valve support guide members and anchored to the one or more commissures of the valve.

For some applications, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

For some applications, the one or more valve support guide members are removable from the patient following the anchoring of the valve support at the atrioventricular valve.

For some applications, the one or more valve support tissue anchors are configured to be anchored to the one or more commissures from ventricular surfaces thereof prior to advancement of the valve support.

For some applications, the one or more valve support tissue anchors includes first and second valve support tissue anchors, the first and second valve support tissue anchors being configured to be anchored to respective first and second commissures of the atrioventricular valve of the patient.

For some applications:

the one or more valve support tissue anchors each include one or more radially-expandable prongs, and the one or more prongs are disposed within a sheath in a compressed state prior to the anchoring and exposed from within the sheath in order to expand and facilitate anchoring of the anchor to the respective commissures.

For some applications, the valve support further includes a flexible generally cylindrical element coupled to the annular element and configured to be positioned in the native atrioventricular valve of the patient and to push aside native leaflets of the native valve, the cylindrical element having first and second ends and a cylindrical body that is disposed between the first and second ends.

For some applications, the cylindrical element includes a flexible wireframe covered by a fabric.

For some applications, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some applications, the apparatus includes the prosthetic valve, and the prosthetic valve is couplable to the valve support.

For some applications:
the first end of the cylindrical element is coupled to the annular element,
during a first period, the second end of the cylindrical element is disposed above the annular element in a manner in which the body of the cylindrical element is disposed above the annular element, and
the cylindrical element is invertible in a manner in which, during a second period, the second end of the cylindrical element is disposed below the annular element and the body of the cylindrical element is disposed below the annular element.

For some applications:
during the first period, the second end of the cylindrical element is disposed in an atrium of a heart of the patient,
the prosthetic valve is advanceable along the one or more prosthetic valve guide members into a ventricle of the heart of the patient, and
in response to advancement of the prosthetic valve into the ventricle, the one or more prosthetic valve guide members are pulled into the ventricle and pull the second end of the cylindrical element into the ventricle to invert the cylindrical element.

There is additionally provided, in accordance with some applications of the present invention, apparatus, including:
one or more valve support guide members configured to be delivered to one or more commissures of a native atrioventricular valve of a patient;
a prosthetic valve support configured to be advanced toward the native valve along the one or more valve support guide members and placed at the native valve;
a prosthetic valve configured to be coupled to the valve support; and
one or more sealing elements configured to facilitate sealing of an interface between the prosthetic valve support and the native valve.

For some applications, the sealing element includes a balloon disposed circumferentially around an outer surface of the prosthetic valve support.

For some applications, the sealing element includes one or more helices that are configured to facilitate sealing of commissures of the native valve with respect to the valve support by being wrapped around chordae tendineae of the native valve.

For some applications, the sealing element includes grasping elements that are configured to facilitate sealing of commissures of the native valve with respect to the valve support by grasping the commissures.

For some applications, the sealing element is configured to facilitate anchoring of the support to the native valve.

For some applications, the valve support is collapsible for transcatheter delivery and expandable to contact the native atrioventricular valve.

For some applications, the prosthetic valve includes two or more prosthetic leaflets.

For some applications, the native atrioventricular valve includes a mitral valve, and the prosthetic valve includes three prosthetic leaflets.

For some applications, the valve support guide members are removable from the patient following coupling of the prosthetic valve to the valve support.

For some applications, the valve support is shaped so as to define a distal portion which is configured to push aside, at least in part, native leaflets of the valve of the patient.

For some applications, the valve support is shaped so as to define one or more holes, the one or more holes being configured to facilitate slidable passage therethrough of a respective one of the one or more valve support guide members.

For some applications, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some applications, the apparatus further includes:
a guide wire configured to be advanced, via the native atrioventricular valve, into a ventricle of the patient, and coupled to an inner wall of the patient's ventricle; and
a valve support guide member tube coupled to the guide wire,
and a distal portion of the valve support guide member is configured to loop through the valve support guide member tube, such that, in response to the valve support guide member being pushed distally, portions of the valve support guide member are pushed to respective commissures of the native valve.

For some applications, the prosthetic valve is shaped so as to define one or more protrusions configured to ensnare one or more native leaflets of the native valve of the patient.

For some applications, the protrusions are disposed in a sinusoidal configuration such that the protrusions conform with a saddle shape of the patient's native annulus.

For some applications, the protrusions are configured to prevent the native leaflets from interfering with a left ventricular outflow tract of the patient, by sandwiching the leaflets between the protrusions and the prosthetic valve support.

For some applications, the valve support includes:
a first end that is configured to be placed on an atrial side of a native atrioventricular valve of a patient; and
a second end that is configured, during a first period, to be disposed inside the patient's atrium, above the first end of the valve support,
the valve support being at least partially invertible in a manner in which, during a second period, the second end of the valve support is disposed at least partially inside a ventricle of the patient, below the first end of the valve support.

For some applications, the valve support includes an annular element and a generally cylindrical element coupled to the annular element, the generally cylindrical element being configured to push aside native leaflets of the native valve, and the cylindrical element has first and second ends and a cylindrical body that is disposed between the first and second ends.

For some applications, the sealing element includes a balloon disposed underneath the annular element and configured to facilitate sealing of an interface between the annular element and the native valve.

For some applications, the apparatus further includes one or more prosthetic valve guide members, the prosthetic valve guide members being configured to facilitate advancement of the prosthetic valve therealong and toward the valve support.

For some applications:

the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

For some applications:

during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end and the body of the cylindrical element into the ventricle to invert the cylindrical element.

There is further provided, in accordance with some applications of the present invention, apparatus, including:

a prosthetic valve support configured to be advanced toward a native atrioventricular valve of a patient and placed at the native valve;

a prosthetic valve configured to be coupled to the valve support, the prosthetic valve being shaped so as to define first and second sets of one or more protrusions, each set of protrusions configured to ensnare a respective native leaflet of the native valve of the patient, the first set of protrusions being disposed within a first circumferential arc with respect to a longitudinal axis of the prosthetic valve, on a first side of a distal end of the prosthetic valve, the second set of protrusions being disposed within a second circumferential arc with respect to the longitudinal axis of the prosthetic valve, on a second side of the distal end of the prosthetic valve, the first and second sets being disposed so as to provide first and second gaps therebetween at the distal end of the prosthetic valve, at least one of the gaps having a circumferential arc of at least 20 degrees; and one or more valve guide members configured to be delivered to one or more commissures of the native valve, and to guide the valve such that the first and second circumferential arcs are aligned with respective leaflets of the native valve and such that the first and second gaps are aligned with respective commissures of the native valve.

For some applications, the at least one of the gaps has a circumferential arc of at least 60 degrees.

For some applications, the first circumferential arc defines an angle of between 25 degrees and 90 degrees about the longitudinal axis of the prosthetic valve.

For some applications, the second circumferential arc defines an angle of between 25 degrees and 90 degrees about the longitudinal axis of the prosthetic valve.

For some applications, the first circumferential arc defines an angle of between 45 degrees and 75 degrees about the longitudinal axis of the prosthetic valve.

For some applications, the second circumferential arc defines an angle of between 45 degrees and 75 degrees about the longitudinal axis of the prosthetic valve.

There is additionally provided, in accordance with some applications of the present invention, a method, including:

determining an area defined by an annulus of a native atrioventricular valve of a patient;

selecting a prosthetic valve to be placed in the native valve by determining that the valve defines a cross-sectional area that is less than 90% of the area defined by the annulus; and deploying the prosthetic valve at the native valve, the selecting of the prosthetic valve facilitating sealing of the native valve with respect to the prosthetic valve by facilitating closing of leaflets of the native valve around the prosthetic valve, upon deployment of the prosthetic valve.

For some applications, selecting the prosthetic valve includes selecting a prosthetic valve having a material disposed on an outer surface thereof.

For some applications, selecting the prosthetic valve includes selecting a prosthetic valve having a material that prevents tissue growth disposed on an outer surface thereof.

For some applications, selecting the prosthetic valve includes selecting a prosthetic valve having a material that promotes tissue growth disposed on an outer surface thereof.

For some applications, selecting the prosthetic valve to be placed in the native valve includes determining that the valve defines a cross-sectional area that is less than 80% of the area defined by the annulus.

For some applications, selecting the prosthetic valve to be placed in the native valve includes determining that the valve defines a cross-sectional area that is less than 60% of the area defined by the annulus.

There is further provided, in accordance with some applications of the present invention, apparatus including:

a valve support for receiving a prosthetic valve, the valve support including:

a first end that is configured to be placed on an atrial side of a native atrioventricular valve of a patient; and a second end that is configured, during a first period, to be disposed inside the patient's atrium, above the first end of the valve support, the valve support being at least partially invertible in a manner in which, during a second period, the second end of the cylindrical element is disposed at least partially inside a ventricle of the patient, below the first end of the valve support.

For some applications, the valve support includes a flexible wireframe covered by a fabric.

For some applications, the valve support is collapsible for transcatheter delivery and expandable to contact the native atrioventricular valve.

For some applications, the valve support defines a surface that is an inner surface of the valve support during the first period, and an outer surface of the valve support during the second period, and the apparatus further includes a sealing material that is disposed on the surface, such that during the second period the sealing material facilitates sealing between the valve support and the native valve.

For some applications, the first end includes a coupling element configured to couple the valve support to tissue of the native valve on the atrial side of the native valve.

For some applications, the first end is shaped to define barbs that are configured to couple the valve support to tissue of the native valve on the atrial side of the native valve For some applications, the valve support includes:

an annular element configured to be positioned along a native annulus of the native atrioventricular valve; and a flexible generally cylindrical element configured to be positioned in the native atrioventricular valve of the patient and to push aside native leaflets of the native valve, the first end of the cylindrical element defining the first end of the valve support, and the first end of the cylindrical element being coupled to the annular element.

For some applications, the apparatus further includes one or more valve support guide members configured to be delivered to one or more commissures of the native atrioventricular valve of the patient, and the one or more valve support guide members are configured to facilitate advancement of the valve support toward the native valve.

For some applications, the valve support is shaped so as to define one or more holes, the one or more holes configured to facilitate slidable passage therethrough of a respective one of the one or more valve support guide members.

For some applications, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

For some applications, the apparatus further includes:

a guide wire configured to be advanced, via the native atrioventricular valve, into a ventricle of the patient, and coupled to an inner wall of the patient's ventricle; and a valve support guide member tube coupled to the guide wire, and a distal portion of the valve support guide member is configured to loop through the valve support guide member tube, such that, in response to the valve support guide member being pushed distally, portions of the valve support guide member are pushed to respective commissures of the native valve.

For some applications, the apparatus further includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

For some applications, the apparatus further includes the prosthetic valve, and the prosthetic valve is couplable to the valve support.

For some applications:

during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end of the cylindrical element into the ventricle to invert the cylindrical element.

For some applications, the apparatus further includes one or more sealing elements configured to facilitate sealing of an interface between the prosthetic valve support and the native valve.

For some applications, the sealing element includes a balloon disposed circumferentially around a surface of the prosthetic valve support.

For some applications, the sealing element includes one or more helices that are configured to facilitate sealing of commissures of the native valve with respect to the valve support by being wrapped around chordae tendineae of the native valve.

For some applications, the sealing element includes grasping elements that are configured to facilitate sealing of commissures of the native valve with respect to the valve support by grasping the commissures.

For some applications, the sealing element is configured to facilitate anchoring of the support to the native valve.

For some applications, the apparatus further includes the prosthetic valve, and the prosthetic valve is couplable to the valve support.

For some applications, the prosthetic valve is collapsible for transcatheter delivery and expandable when exposed from within a delivery catheter.

For some applications, the prosthetic valve includes two or more prosthetic leaflets.

For some applications, the native atrioventricular valve includes a mitral valve, and the prosthetic valve includes three prosthetic leaflets.

For some applications, the prosthetic valve is shaped so as to define one or more protrusions configured to ensnare one or more native leaflets of the native valve of the patient.

For some applications, the protrusions are disposed in a sinusoidal configuration such that the protrusions conform with a saddle shape of the patient's native annulus.

For some applications, the protrusions are configured to prevent the native leaflets from interfering with a left ventricular outflow tract of the patient, by sandwiching the leaflets between the protrusions and the prosthetic valve support.

There is further provided, in accordance with some applications of the present invention, apparatus, including:

a guide wire configured to be advanced into a patient's ventricle via a native atrioventricular valve of the patient, and coupled to an inner wall of the patient's ventricle;

a valve support guide member tube coupled to the guide wire;

a valve support guide member, a distal portion of the valve support guide member looping through the valve support guide member tube, such that, in response to the valve support guide member being pushed distally, portions of the valve support guide member are pushed to respective commissures of the native valve;

a prosthetic valve support configured to be advanced toward the commissures of the native valve along the valve support guide member portions; and a prosthetic valve configured to be coupled to the valve support.

For some applications, first and second free ends of the valve support guide member are accessible from a site outside a body of the patient.

For some applications, the valve support includes:

an annular element configured to be positioned along a native annulus of the native atrioventricular valve; and a generally cylindrical element configured to be positioned in the native atrioventricular valve of the patient and to push aside native leaflets of the native valve, the cylindrical element being coupled to the annular element, at a first end of the cylindrical element.

For some applications, the valve support is shaped so as to define one or more holes, the one or more holes configured to facilitate slidable passage therethrough of respective portions of the portions of the valve support guide member.

For some applications, the guide member is configured to facilitate advancement of the prosthetic valve therealong and toward the valve support.

For some applications, the prosthetic valve is collapsible for transcatheter delivery and expandable when exposed from within a delivery catheter.

For some applications, the prosthetic valve includes two or more prosthetic leaflets.

For some applications, the native atrioventricular valve includes a mitral valve, and the prosthetic valve includes three prosthetic leaflets.

For some applications, the guide member is removable from the patient following the coupling of the prosthetic valve to the valve support.

For some applications, the prosthetic valve is shaped so as to define one or more protrusions configured to ensnare one or more native leaflets of the native valve of the patient.

For some applications, the protrusions are disposed in a sinusoidal configuration such that the protrusions conform with a saddle shape of the patient's native annulus.

For some applications, the protrusions are configured to prevent the native leaflets from interfering with a left ventricular outflow tract of the patient, by sandwiching the leaflets between the protrusions and the prosthetic valve support.

For some applications, the apparatus further includes one or more sealing elements configured to facilitate sealing of an interface between the prosthetic valve support and the native valve.

For some applications, the sealing element includes a balloon disposed circumferentially around a surface of the prosthetic valve support.

For some applications, the sealing element includes one or more helices that are configured to facilitate sealing of commissures of the native valve with respect to the valve support by being wrapped around chordae tendineae of the native valve.

For some applications, the sealing element includes grasping elements that are configured to facilitate sealing of commissures of the native valve with respect to the valve support by grasping the commissures.

For some applications, the sealing element is configured to facilitate anchoring of the support to the native valve.

There is additionally provided, in accordance with some applications of the present invention, apparatus, including:
one or more valve guide members configured to be delivered to one or more commissures of a native atrioventricular valve of a patient;
a prosthetic valve configured to be advanced to be advanced toward the native valve along the one or more valve guide members and placed at the native valve at at least the one or more commissures; and
one or more proximally-facing grasping elements that are configured to facilitate sealing of commissures of the native valve with respect to the valve by:
being inserted into a ventricle of the patient; and
being pulled proximally and being closed around tissue in a vicinity of the commissures.

For some applications, the grasping elements include two surfaces that are hingedly coupled to one another, and that are configured to facilitate the sealing of the commissures of the native valve with respect to the prosthetic valve by being closed about the hinge with respect to one another.

There is further provided, in accordance with some applications of the present invention, a method, including:

advancing one or more valve support guide members toward one or more commissures of a native atrioventricular valve of a patient;
placing a prosthetic valve support at the native atrioventricular valve by advancing the valve support along the one or more valve support guide members;
coupling a prosthetic valve to the prosthetic valve support; and
facilitating sealing of an interface between the prosthetic valve support and the native valve by deploying a sealing element in a vicinity of the interface.

There is additionally provided, in accordance with some applications of the present invention, a method including:
placing a first end of a prosthetic valve support on an atrial side of a native atrioventricular valve of a patient, such that a second end of the valve support is disposed, during a first period, inside the patient's atrium, above the first end of the valve support; and
subsequent to the placing of the valve support, inverting at least a portion of the valve support such that, during a second period, the second end of the valve support is disposed at least partially inside a ventricle of the patient, below the first end of the valve support.

There is additionally provided, in accordance with some applications of the present invention, a method, including:
advancing a guide wire, via a native atrioventricular valve, into a ventricle of the patient, a valve support guide member tube being coupled to the guide wire;
coupling a distal end of the guide wire to an inner wall of the patient's ventricle; and
causing portions of a valve support guide member to be pushed to respective commissures of the native valve, by pushing the guide member distally, a distal portion of the valve support guide member looping through the valve support guide member tube;
advancing a prosthetic valve support toward the commissures of the native valve along the valve support guide member portions; and
coupling a prosthetic valve to the valve support.

There is further provided, in accordance with some applications of the present invention, a method, including:
advancing one or more valve guide members toward one or more commissures of a native atrioventricular valve of a patient;
placing a prosthetic valve at the native atrioventricular valve by advancing the valve along the one or more valve guide members; and
facilitating sealing of commissures of the native valve with respect to the valve by:
inserting into a ventricle of the patient one or more grasping elements that are coupled to the prosthetic valve;
pulling the grasping elements proximally; and
closing the grasping elements around tissue in a vicinity of the commissures.

The present invention will be more fully understood from the following detailed description of embodiments thereof, taken together with the drawings, in which:

BRIEF DESCRIPTION OF THE DRAWINGS

FIGS. 2A-D are schematic illustrations of the advancement of a prosthetic valve support toward a native atrioventricular valve of a patient, in accordance with some applications of the present invention;

FIGS. 2G-K are schematic illustrations of the advancement of a prosthetic valve and the coupling of the prosthetic valve to the valve support, in accordance with some applications of the present invention;

FIGS. 3C-D are schematic illustrations of locking of the prosthetic valve support at the native valve, the valve support including the sealing balloon, in accordance with some applications of the present invention;

FIGS. 4A-C are schematic illustrations of a valve support being used with commissural helices that facilitate anchoring and/or sealing of the valve support, in accordance with some applications of the present invention;

FIGS. 5A-D are schematic illustrations of grasping elements being used to anchor and/or provide sealing of a prosthetic valve, in accordance with some applications of the present invention;

FIGS. 6A-B are schematic illustrations of a prosthetic valve that includes a sealing material, in accordance with some applications of the present invention;

FIGS. 7A-F are schematic illustrations of a guide wire delivery system, in accordance with some applications of the present invention;

FIGS. 8A-C are schematic illustrations of a valve support that has a cylindrical element that is invertible, in accordance with some applications of the present invention;

FIG. 9E is a schematic illustration of inversion of the invertible prosthetic valve support at the native valve, in accordance with some applications of the present invention;

FIGS. 9F-H are schematic illustrations of the advancement of a prosthetic valve and the coupling of the prosthetic valve to the invertible valve support, in accordance with some applications of the present invention;

FIG. 10 is a schematic illustration of a prosthetic valve, the cross-sectional area of which is smaller than the area defined by the patient's native valve annulus, in accordance with some applications of the present invention;

FIGS. 11A-D are schematic illustrations of a prosthetic valve that defines protrusions from portions of the distal end of the valve, in accordance with some applications of the present invention;

FIGS. 12A-C are schematic illustrations of a prosthetic valve that defines distal protrusions that are disposed sinusoidally around the circumference of the valve, in accordance with some applications of the present invention;

FIGS. 14A-D are schematic illustrations of respective configurations of a prosthetic valve support, in accordance with some applications of the present invention;

FIGS. 15A-E are schematic illustrations of respective steps of a procedure for deploying a prosthetic valve, in accordance with some applications of the present invention;

FIGS. 16A-H are schematic illustrations of respective steps of an alternative procedure for deploying a prosthetic valve, in accordance with some applications of the present invention;

FIGS. 19A-D are schematic illustrations of the valve support of FIGS. 18A-B being implanted in the native valve of the patient and facilitating implantation of a prosthetic valve, in accordance with some applications of the present invention; and FIGS. 20A-B are schematic illustrations of a prosthetic valve and a prosthetic valve support deployed, respectively, at a tricuspid valve, and at an aortic valve, in accordance with some applications of the present invention.

DETAILED DESCRIPTION OF THE EMBODIMENTS

Figure 1A:
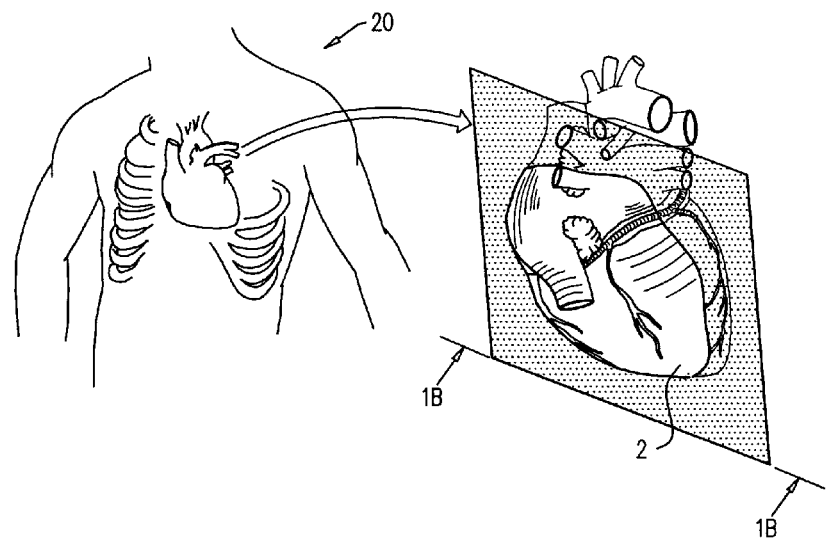
FIGS. 1A-B are schematic illustrations of advancement of one or more guide members toward respective commissures of a mitral valve, in accordance with some applications of the present invention.
Figure 1B:
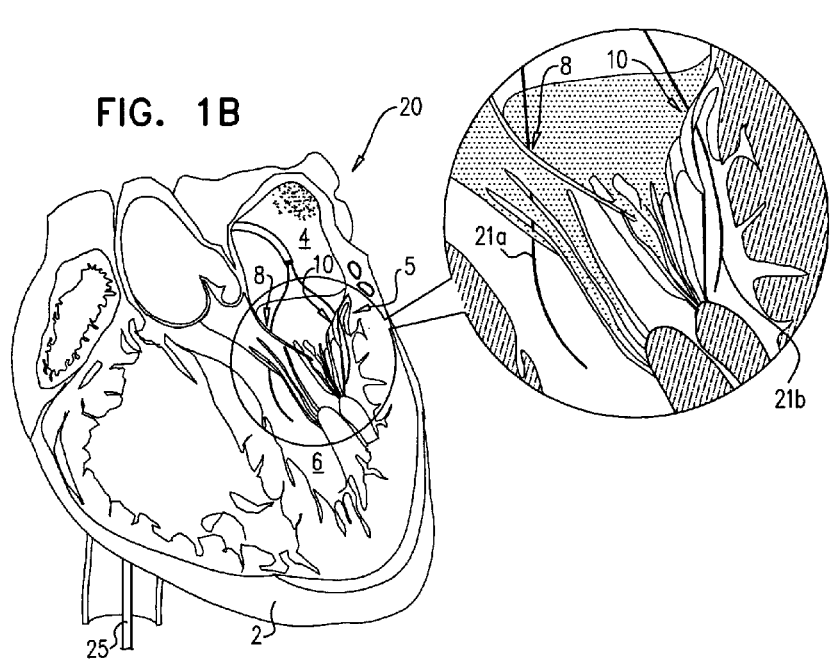
Figure 1C:
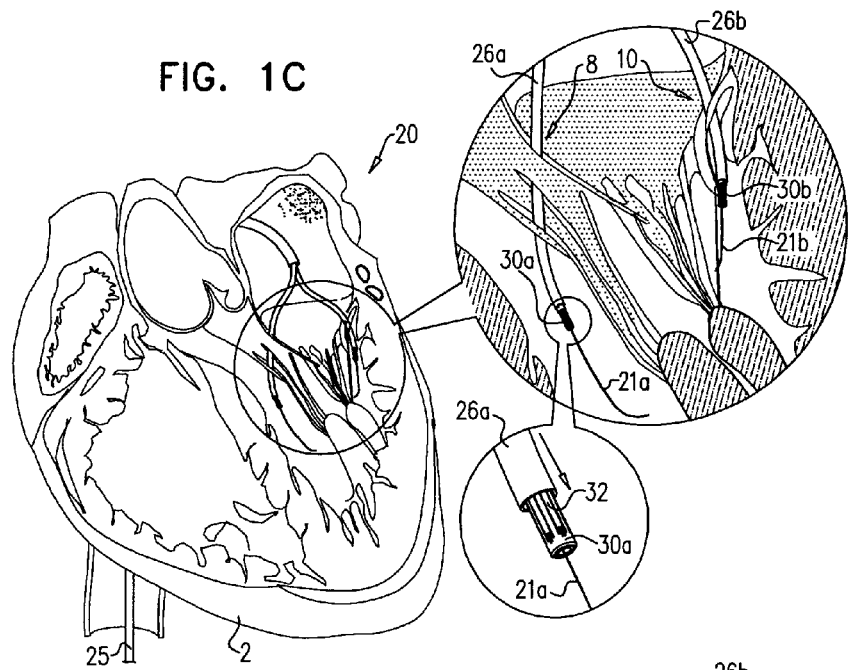
FIGS. 1C-D are schematic illustrations of the advancement and deployment of commissural anchors via the guide members, in accordance with some applications of the present invention.

Reference is now made to FIGS. 1A-B, which are schematic illustrations of a system 20 for replacing an atrioventricular valve 5 of a patient comprising one or more guide members 21a and 21b which are advanced toward first and second commissures 8 and 10 of valve 5 of a heart 2 of the patient, in accordance with some applications of the present invention. For some applications, guide members 21a and 21b comprise distinct guide members. Alternatively (as shown in FIGS. 7A-F), only one guide member is looped through commissures 8 and 10 in a manner in which the guide member defines a looped portion between commissures 8 and 10 (i.e., a portion of the guide member that is disposed in a ventricle 6 of heart 2), and first and second free ends which are disposed and accessible at a site outside the body of the patient. For such applications, the guide member defines portions 21a and 21b.

It is noted that for applications in which valve 5 is the patient's mitral valve, first and second commissures 8 and 10 are the anterior and posterior commissures. For applications in which valve 5 is the patient's tricuspid valve (which includes three commissures), the first and second commissures are typically the anterior and posterior commissures of the tricuspid valve.

For some applications, guide members 21a and 21b comprise guide wires having a diameter of 0.035 inches.

The transcatheter procedure typically begins with the advancing of a semi-rigid guide wire into a right atrium 4 of the patient. The semi-rigid guide wire provides a guide for the subsequent advancement of a sheath 25 therealong and into the right atrium. Once sheath 25 has entered the right atrium, the semi-rigid guide wire is retracted from the patient's body. Sheath 25 typically comprises a 13-20 F sheath, although the size may be selected as appropriate for a given patient. Sheath 25 is advanced through vasculature into the right atrium using a suitable point of origin typically determined for a given patient. For example:

sheath 25 may be introduced into the femoral vein of the patient, through an inferior vena cava, into the right atrium, and into the left atrium transseptally, typically through the fossa ovalis;

sheath 25 may be introduced into the basilic vein, through the subclavian vein to the superior vena cava, into the right atrium, and into the left atrium transseptally, typically through the fossa ovalis; or sheath 25 may be introduced into the external jugular vein, through the subclavian vein to the superior vena cava, into the right atrium, and into the left atrium transseptally, typically through the fossa ovalis.

In some applications of the present invention, sheath 25 is advanced through the inferior vena cava of the patient and into the right atrium using a suitable point of origin typically determined for a given patient.

Sheath 25 is advanced distally until sheath 25 reaches the interatrial septum. For some applications, a resilient needle and a dilator (not shown) are advanced through the sheath and into the heart. In order to advance the sheath transseptally into the left atrium, the dilator is advanced to the septum, and the needle is pushed from within the dilator and is allowed to puncture the septum to create an opening that facilitates passage of the dilator and subsequently the sheath therethrough and into the left atrium. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 25 through the septum and into the left atrium is followed by the extraction of the dilator and the needle from within sheath 25.

FIGS. 1C-D and 2A-B show advancement of one or more tissue anchors 30a and 30b along guide members 21a and 21b, respectively. Anchors 30a and 30b comprise a flexible, biocompatible material (e.g., nitinol) and comprise one or more (e.g., a plurality of) radially-expandable prongs 32 (e.g., barbs). Each anchor 30a and 30b is reversibly coupled to a respective delivery lumen 27a and 27b. Each delivery lumen 27 slides around a respective guide member 21. A respective surrounding sheath 26a and 26b surrounds each delivery lumen 27a and 27b and around anchors 30a and 30b at least in part in order to compress and prevent expansion of prongs 32 of tissue anchors 30a and 30b.

Figure 1D:
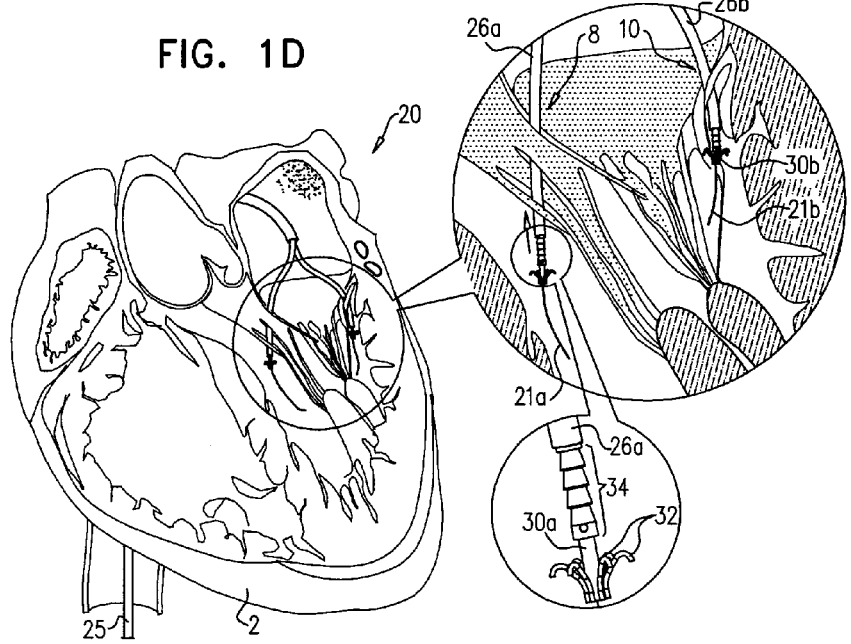

As shown in FIG. 1D, the distal ends of lumens 27a and 27b are reversibly coupled to ribbed crimping structures 34. As described hereinbelow, anchors 30a and 30b are anchored to ventricular surfaces of commissures 8 and 10. Following the anchoring, ribbed crimping structures 34 extend from anchors 30a and 30b through commissures 8 and 10, respectively, and toward the atrial surfaces of commissures 8 and 10. Ribbed crimping structures 34 are configured to facilitate anchoring of a valve support (described hereinbelow) to the atrial surfaces of commissures 8 and 10.

Anchors 30a and 30b, ribbed crimping structures 34, and the distal ends of surrounding sheaths 26a and 26b are advanced into ventricle 6. Subsequently, anchors 30a and 30b are pushed distally from within sheaths 26a and 26b, (or sheaths 26a and 26b are pulled proximally with respect to anchors 30a and 30b) to expose anchors 30a and 30b. As anchors 30a and 30b are exposed from within sheaths 26a and 26b, prongs 32 are free to expand, as shown in FIG. 1D. Prongs 32 expand such that anchors 30a and 30b assume a flower shape. Prongs 32, collectively in their expanded state, create a larger surface area to engage tissue than in their compressed states. Following the exposing of anchors 30a and 30b, sheaths 26a and 26b are extracted.

Figure 2A:
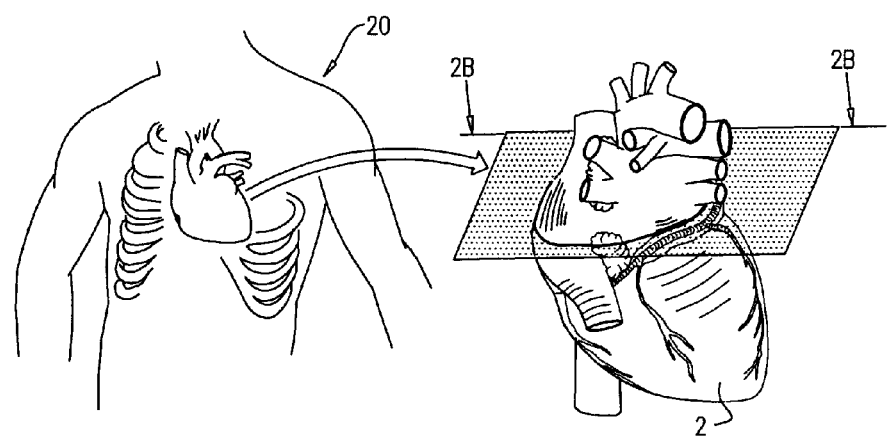
Figure 2B:
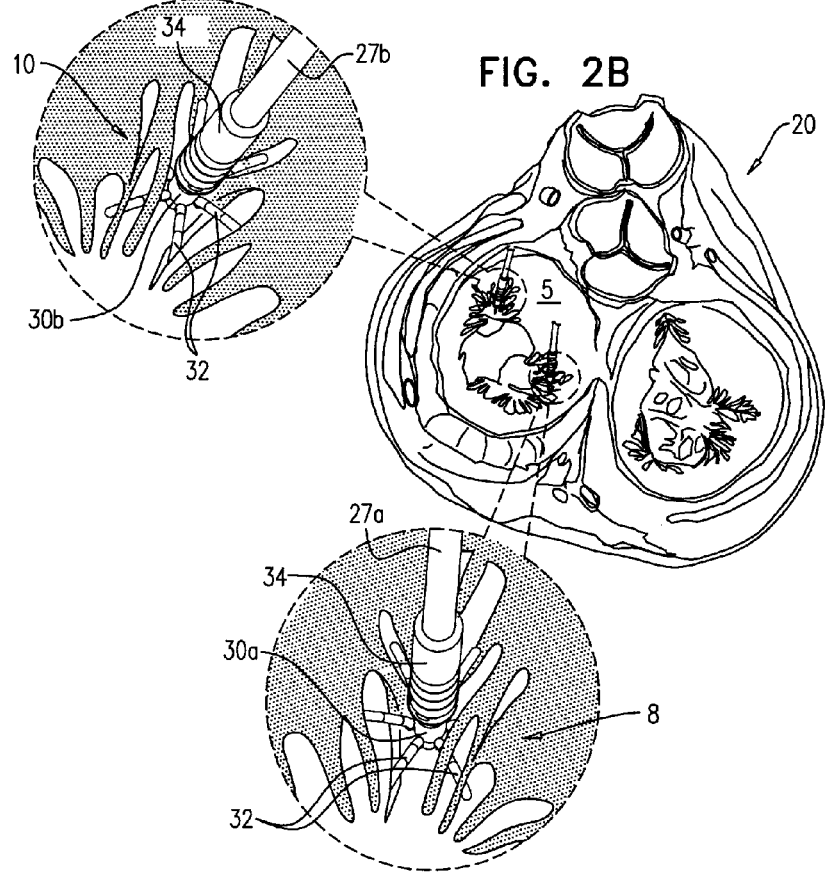

As shown in FIG. 2B, lumens 27a and 27b are pulled proximally so that prongs 32 of anchors 30a and 30b engage respective ventricular surface of commissures 8 and 10. Prongs 32 create a large surface area which restricts proximal motion of anchors 30a and 30b from commissures 8 and 10, respectively.

For some applications, following the anchoring of anchors 30a and 30b to commissures 8 and 10, respectively, guide members 21a and 21b are removed from the body of the patient.

Reference is now made to FIGS. 2C-F, which are schematic illustrations of the advancement of a prosthetic valve support 40 along lumens 27a and 27b, in accordance with some applications of the present invention. In such a manner, lumens 27a and 27b function as valve support guide members. Support 40 comprises a collapsible skirt having a proximal annular element 44 and a distal cylindrical element 42. Support 40 is configured to assume a collapsed state (e.g., surrounded by a sheath or overtube 50 shown in FIG. 2C) for minimally-invasive delivery to the diseased native valve, such as by percutaneous or transluminal delivery using one or more catheters. FIG. 2C and the other figures show support 40 in an expanded state after delivery in right atrium 4 and advancement toward the native valve. As shown in FIG. 2D, support 40 is shaped so as to define one or more (e.g., two, as shown in View A) holes 46a and 46b for slidable advancement of support 40 along lumens 27a and 27b, respectively. That is, prior to introduction of support 40 into the body of the patient, lumens 27a and 27b are threaded through holes 46a and 46b, respectively, and support 40 is slid along lumens 27a and 27b. Support 40 is slid by pushing elements 52a and 52b which surround delivery lumens 27a and 27b, respectively.

It is to be noted that support 40 is slid along lumens 27a and 27b by way of illustration and not limitation. That is, for some applications, following the anchoring of anchors 30a and 30b to commissures 8 and 10, respectively, guide members 21a and 21b are not removed from the body of the patient, but rather lumens 27a and 27b are removed (e.g., by being decoupled from crimping structures 34) leaving behind anchors 30a and 30b and guide members 21a and 21b. Guide members 21a and 21b may then be threaded through holes 46a and 46b, respectively, and support 40 is slid along guide members 21a and 21b. In such a manner, guide members 21a and 21b function as valve support guide members.

Figure 2E:
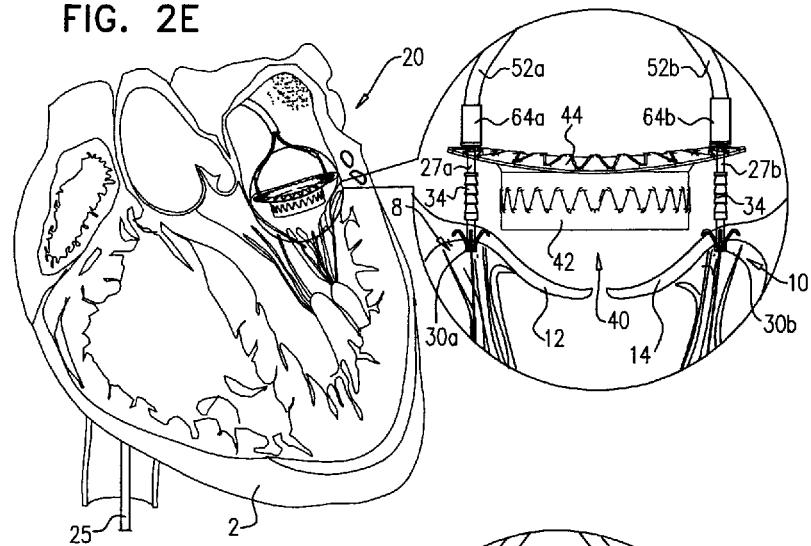
FIGS. 2E-F are schematic illustrations of locking of the prosthetic valve support at the native valve, in accordance with some applications of the present invention.

Support 40 comprises a collapsible flexible support frame 48, which is at least partially covered by a covering 49. Support 40 is configured to be placed at native valve 5, such that cylindrical element 42 passes through the orifice of the native valve and extends towards, and, typically partially into, ventricle 6 (as shown in FIG. 2E). Cylindrical element 42 typically pushes aside and presses against native leaflets of native valve 5 at least in part, which are left in place during and after implantation of the prosthetic valve. Annular element 44 is configured to be placed around a native annulus 11 of the native valve, and to extend at least partially into an atrium 4 such that annular element 44 rests against the native annulus. Annular element 44 is typically too large to pass through the annulus, and may, for example, have an outer diameter of between 30 and 60 mm.

For some applications, collapsible support frame 48 comprises a stent, which comprises a plurality of struts. The struts may comprise, for example, a metal such as nitinol or stainless steel. For some applications, frame 48 comprises a flexible metal, e.g., nitinol, which facilitates compression of support 40 within a delivery sheath or overtube 50. For some applications, covering 49 comprises a fabric, such as a woven fabric, e.g., Dacron. Covering 49 is typically configured to cover at least a portion of cylindrical element 42, and at least a portion of annular element 44. The covering may comprise a single piece, or a plurality of pieces sewn together.

As shown in FIG. 2D, pushing elements 52a and 52b are each coupled to locking crimping elements 64a and 64b, respectively. Locking crimping elements 64a and 64b are disposed adjacently, proximally to holes 46a and 46b respectively of valve support 40. These techniques enable the surgeon to readily bring crimping elements 64a and 64b to the appropriate sites along annular element 44, without the need for excessive imaging, such as fluoroscopy.

FIG. 2E shows valve support 40 prior to implantation at annulus 11. As shown, ribbed crimping structures 34 project away from anchors 30a and 30b, through commissures 8 and 10, and toward atrium 4. Valve support 40 is advanced along lumens 27a and 27b toward structures 34 by being pushed by pushing elements 52a and 52b and locking crimping elements 64a and 64b.

Figure 2F:
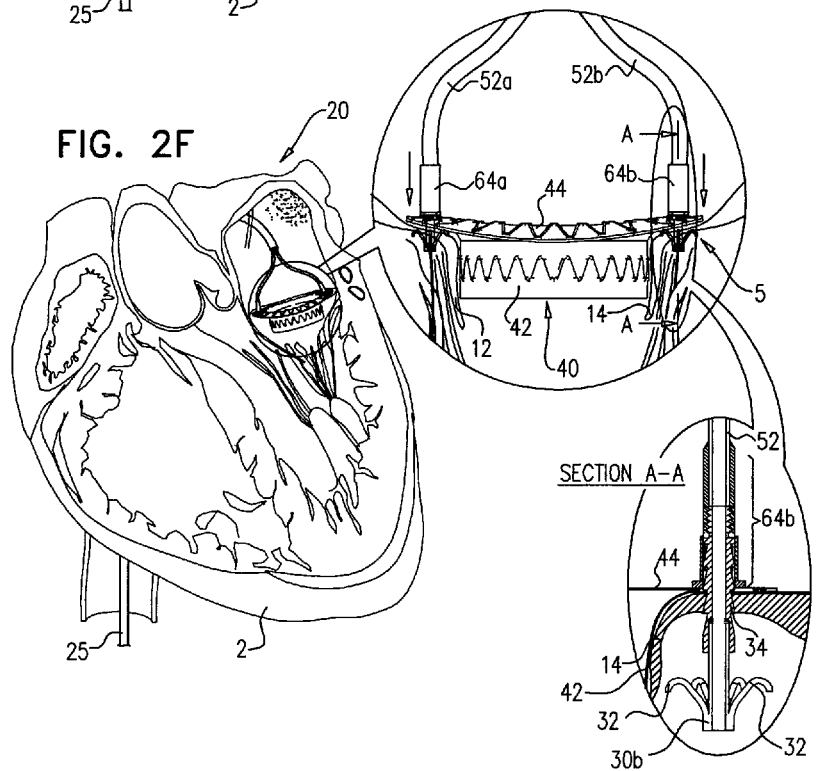

In FIG. 2F, valve support 40 is further pushed by pushing elements 52a and 52b and locking crimping elements 64a and 64b such holes 46a and 46b of support 40 advance around ribbed crimping structures 34. As holes 46a and 46b are advanced around ribbed crimping structures 34, locking crimping elements 64a and 64b advance over and surround ribbed crimping elements 34 to lock in place valve support 40 from an atrial surface of valve 5.

Responsively to the placement of valve support 40 at native valve 5, cylindrical element 42 is positioned partially within ventricle 6 and native leaflets 12 and 14 of native valve 5 are pushed aside.

As shown in section A-A, ribbed crimping structures 34 are shaped so as to define a plurality of male couplings. Locking crimping elements 64a and 64b each comprise a cylindrical element having an inner lumen that is shaped so as to surround a respective ribbed crimping structure 34. Each inner lumen of locking crimping elements 64a and 64b is shaped so as to define female couplings to receive the male couplings of ribbed crimping structure 34. The female couplings of locking crimping element 64 are directioned such that they facilitate distal advancement of locking crimping element 64 while restricting proximal advancement of locking crimping element 64. When the female couplings of locking crimping element 64 receive the male couplings of ribbed crimping structure 34, valve support 40 is locked in place from an atrial surface of valve 5. It is to be noted that for some applications, ribbed crimping elements 34 comprise female couplings, and locking crimping elements 64 comprise male couplings.

Reference is now made to FIGS. 2G-K which are schematic illustrations of the coupling of a prosthetic atrioventricular valve 80 to valve support 40, in accordance with some applications of the present invention. Support 40 receives the prosthetic valve and functions as a docking station. Thus, the docking station is a coupling element that provides coupling between two other elements (in this case, between annulus 11 and the prosthetic valve.)

Following the placement of support 40 at annulus 11, pushing elements 52a and 52b and sheath or overtube 50 are removed from the body of the patient, leaving behind lumens 27a and 27b, as shown in FIG. 2G.

As shown in FIG. 2G, a guide wire 72 is advanced toward ventricle 6 and facilitates the advancement of an overtube 70 through sheath 25 and the positioning of a distal end of overtube 70 within ventricle 6. Overtube 70 facilitates the advancement of prosthetic valve 80 in a compressed state, toward valve support 40.

FIG. 2H shows partial deployment of valve 80 within ventricle 6 of heart 2. Valve 80 is shown comprising an expandable frame 79 comprising a plurality of stent struts by way of illustration and not limitation. The wireframe of valve 80 comprises a flexible metal, e.g., nitinol or stainless steel. It is to be noted that the wireframe of valve 80 is covered by a covering (not shown for clarity of illustration) comprising a braided mesh or in a fabric such as a woven fabric, e.g., Dacron. The covering is typically configured to cover at least a portion of the frame. The covering may comprise a single piece, or a plurality of pieces sewn together. Expandable frame 79 is typically self-expandable, although the scope of the present invention includes using a prosthetic valve that includes a balloon expandable frame, mutatis mutandis.

Following the partial deployment of valve 80 in ventricle 6, overtube 70 is pulled proximally to pull valve 80 proximally such that cylindrical element 42 and/or annular element 44 of valve support 40 surrounds a proximal portion of prosthetic valve 80. Valve 80 has a tendency to expand such that valve 80 is held in place with respect to valve support 40 responsively to radial forces acted upon valve support 40 by prosthetic valve 80.

Valve 80 comprises a plurality of distal protrusions 84 (e.g., snares). When valve 80 is pulled proximally, as described hereinabove, protrusions 84 ensnare and engage the native leaflets of the atrioventricular valve. By the ensnaring of the native leaflets, protrusions 84 sandwich the native valve between protrusions 84 and prosthetic valve support 40. Such ensnaring helps further anchor prosthetic valve 80 to the native atrioventricular valve. The scope of the present invention includes using any sort of protrusions (e.g., hooks) that protrude from the distal end of expandable frame 79 of prosthetic valve 80 and that are configured such that the native valve is sandwiched between the protrusions and valve support 40. Typically, the protrusions cause sandwiching of the native valve leaflets, such that the leaflets do not interfere with the left ventricular outflow tract (LVOT).

For some applications, protrusions 84 are such as to (a) prevent proximal migration of the valve into the patient's atrium, while (b) allowing movement of the native leaflets with respect to the frame of the prosthetic valve. For example, the protrusions may have the aforementioned functionalities by having lengths of less than 5 mm, and/or by a total width of each set of protrusions corresponding to respective leaflets of the native valve being less than 5 mm. For example, the valve may include a single protrusion corresponding to each leaflet of the native valve, the width of each of the single protrusions being less than 1 mm. Thus, the valve may be stopped from proximally migrating into the atrium, by the protrusions preventing the distal end of the valve from migrating further proximally than edges of native leaflets of the valve. Furthermore, the protrusions may allow movement of the native leaflets with respect to the frame of the prosthetic valve by not generally squeezing the native leaflets between the protrusions and the frame of the valve. For some applications, by allowing movement of the native leaflets with respect to the frame of the prosthetic valve, sealing of the native leaflets against the outer surface of the frame of the prosthetic valve is facilitated, in accordance with the techniques described hereinbelow with reference to FIG. 10. Typically, valve support 40 prevents the valve from migrating distally into the patient's ventricle.

For some applications, during the procedure, the prosthetic valve is pulled back proximally with respect to valve support, as described hereinabove. The prosthetic valve is pulled back to a position with respect to valve support that is such that protrusions 84 prevent the native leaflets from interfering with the LVOT, by sandwiching the native leaflets between the protrusions and the valve support, and/or by anchoring ends of the native leaflets as described hereinabove. The prosthetic valve is then deployed at this position.

For some applications, protrusions are disposed on the valve on the sides of the valve that are adjacent to the anterior and posterior leaflets of the native valve, and the valve does not includes protrusions on the portions of the valve that are adjacent to the commissures of the native valve, as described with reference to FIGS. 11A-D. For some applications, the protrusions are disposed in a sinusoidal configuration in order to conform with the saddle shape of the native valve, as described hereinbelow with reference to FIGS. 12A-C.

Additionally, as shown in FIG. 2J, valve 80 comprises one or more (e.g., a plurality, as shown) coupling elements 81 at the proximal end of valve 80. Overtube 70, which facilitates the advancement of prosthetic valve 80, is reversibly coupled to valve 80, via coupling elements 81.

Prosthetic valve 80 is configured for implantation in and/or at least partial replacement of a native atrioventricular valve 5 of the patient, such as a native mitral valve or a native tricuspid valve. Prosthetic valve 80 is configured to assume a collapsed state for minimally-invasive delivery to the diseased native valve, such as by percutaneous or transluminal delivery using one or more catheters. FIG. 2J shows prosthetic valve 80 in an expanded state after delivery to the native valve.

Figure 2K:
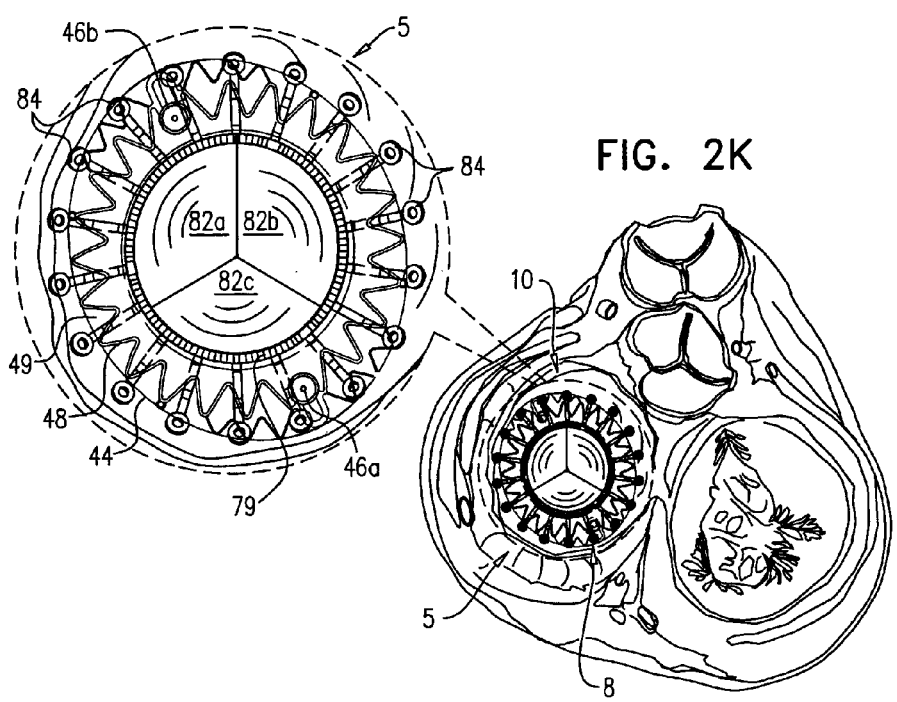

Reference is now made to FIG. 2K which shows a bird's-eye view of valve 80. Prosthetic valve 80 further comprises a plurality of valve leaflets 82, which may be artificial or tissue-based. The leaflets are typically coupled to an inner surface of the valve prosthesis. Leaflets 82 are coupled, e.g., sewn, to expandable frame 79 and/or to the covering. For applications in which the prosthetic valve is configured to be implanted at the native mitral valve, the prosthetic valve typically comprises three leaflets 82a, 82b, and 82c, as shown in FIG. 2K.

Figure 3A:
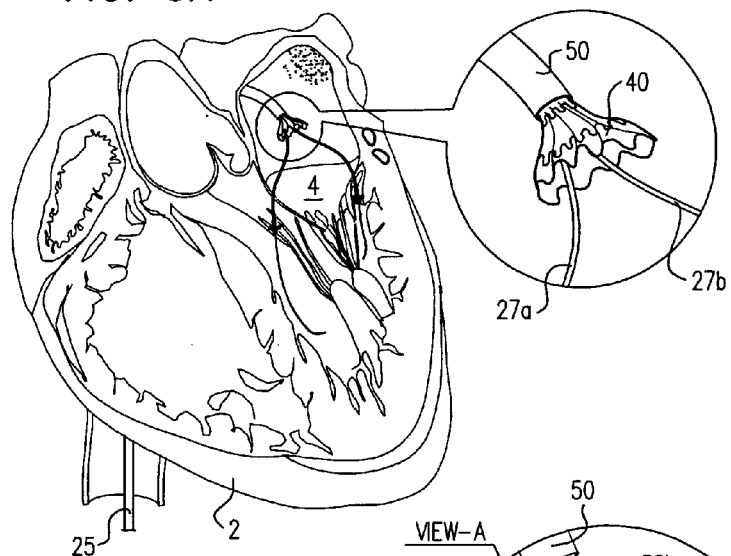
FIGS. 3A-B are schematic illustrations of the advancement of a prosthetic valve support toward a native atrioventricular valve of a patient, the valve support including a sealing balloon, in accordance with some applications of the present invention.
Figure 3B:
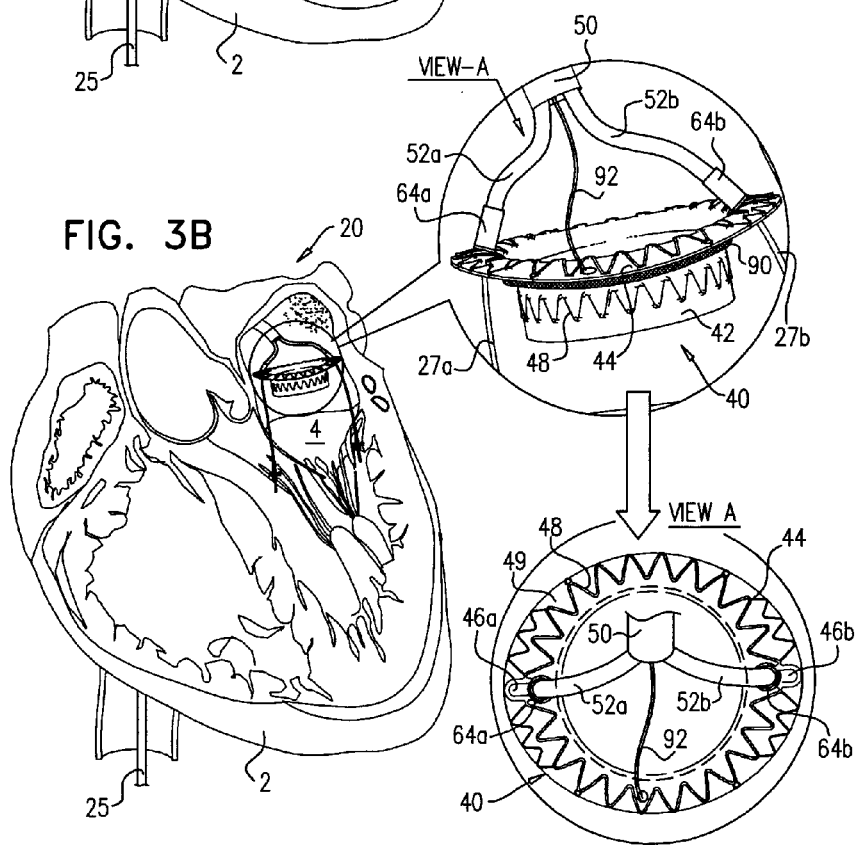

Reference is now made to FIGS. 3A-D, which are schematic illustrations of the advancement of prosthetic valve support 40 toward native atrioventricular valve 5 of a patient, the valve support including a sealing balloon 90, in accordance with some applications of the present invention. The steps shown in FIGS. 3A-C are generally similar to those shown in FIGS. 2C-F. For some applications, sealing balloon 40 is disposed on the valve-facing, lower side of annular element 44 of the prosthetic valve support. FIG. 3D shows valve support 40, the valve support having been implanted at annulus 11. Typically, at this stage, balloon 40 is inflated, as shown in the transition from FIG. 3C to FIG. 3D. The balloon is inflated via an inflation lumen 92, shown in FIG. 3C, for example. For some applications, the balloon seals the interface between the prosthetic valve support and native annulus 11, thereby reducing retrograde blood flow from ventricle 6 into atrium 4, relative to retrograde blood flow in the absence of a sealing balloon. For some applications, the balloon is inflated prior to the placement of the prosthetic support at annulus 11.

Figure 4B:
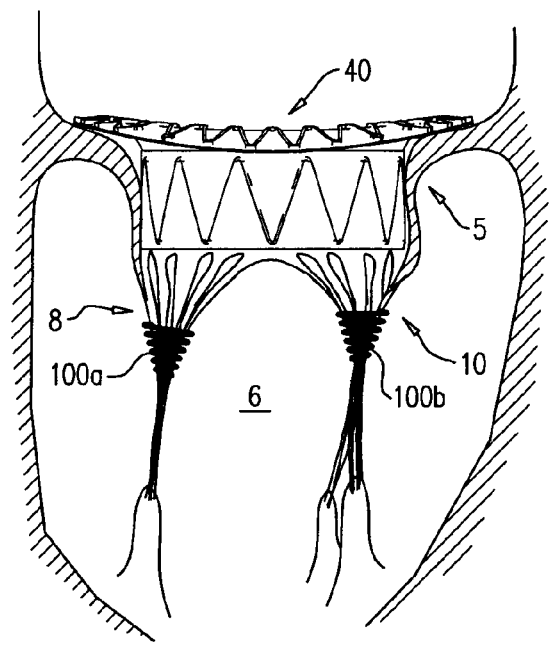
Figure 4C:
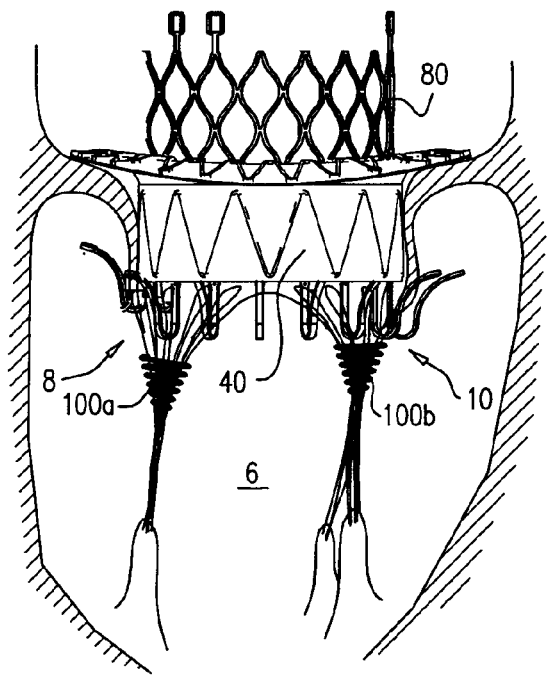

Reference is now made to FIGS. 4A-C, which are schematic illustrations of prosthetic valve support 40 being used with commissural helices 100a and 100b that facilitate anchoring and/or sealing of the valve support, in accordance with some applications of the present invention. For some applications, commissural helices are used as an alternative or in addition to anchors 30a and 30b and/or other anchoring elements described herein, in order to facilitate the anchoring of valve support 40.

Commissural helices 100a and 100b are typically placed at commissures 8 and 10 in a generally similar technique to that described with reference to anchors 30a and 30b. Typically, each helix 30a and 30b is reversibly coupled to a respective delivery lumen 27a and 27b. As described above, each delivery lumen 27 slides around a respective guide member 21, and a respective surrounding sheath 26a and 26b surrounds each delivery lumen 27a and 27b.

Commissural helices 100a and 100b (optionally, ribbed crimping structures 34), and the distal ends of surrounding sheaths 26a and 26b are advanced into ventricle 6. The helices are pushed out of the distal ends of surrounding sheaths 26a and 26b.

Subsequently, the helices are rotated proximally such that the helices wrap around at least some chordae tendineae 102 of the patient. Following the advancement of the helices out of sheaths 26a and 26b, the sheaths are extracted. For some applications the helices are conical helices (as shown), and the wider end of the conical helix is disposed at the proximal end of the helix.

Subsequent to the placement of commissural helices 100a and 100b around the chordae tendineae, prosthetic valve support 40 is placed at annulus 11, in accordance with the techniques described hereinabove, and as shown in FIG. 4B. Subsequently, prosthetic valve 80 is coupled to the prosthetic valve support, in accordance with the techniques described hereinabove, and as shown in FIG. 4C.

Typically, commissural helices 100a and 100b facilitate sealing of native commissures 8 and 10, thereby reducing retrograde blood flow via the commissures, relative to retrograde blood flow in the absence of the helices. Further typically, the sealing of the native commissures facilitates anchoring of the prosthetic valve support to native valve 5.

Figure 5C:
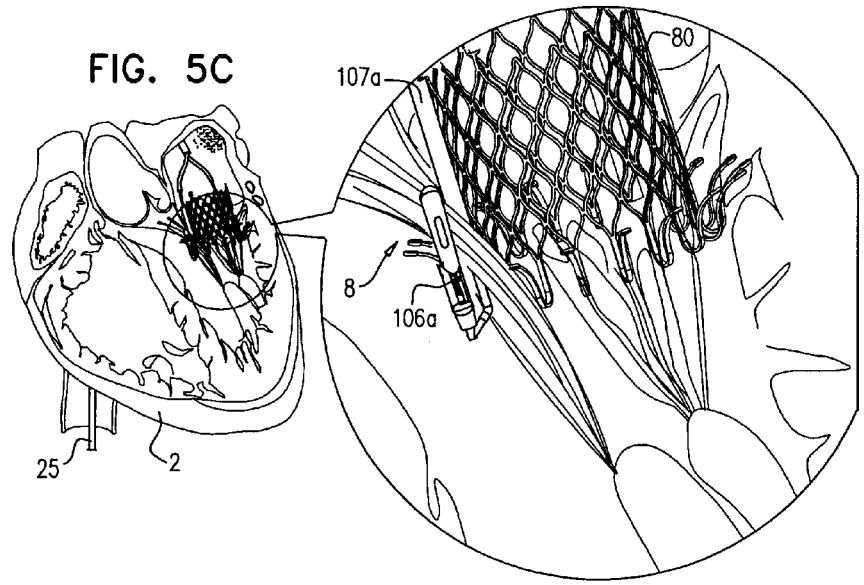

Reference is now made to FIGS. 5A-D, which are schematic illustrations of grasping elements 106a and 106b being used to anchor prosthetic valve 80, in accordance with some applications of the present invention. For some applications, guide members 21a and 21b are advanced toward first and second commissures 8 and 10 of valve 5 of the patient, as described hereinabove. Grasping elements 106a and 106b are reversibly coupled to distal ends of delivery lumen 27a and 27b, the delivery lumens being advanced over respective guide members, as described hereinabove. For some applications, the guiding members and the grasping elements are advanced toward the patient's commissures via surrounding sheaths 26a and 26b, the surrounding sheaths being generally as described hereinabove. The grasping elements are typically placed distally to the commissures in a proximally-facing configuration, as shown in FIG. 5A. For example, as shown, the grasping elements may be configured to be proximally facing due to the coupling of the grasping elements to the guide members.

Figure 5D:
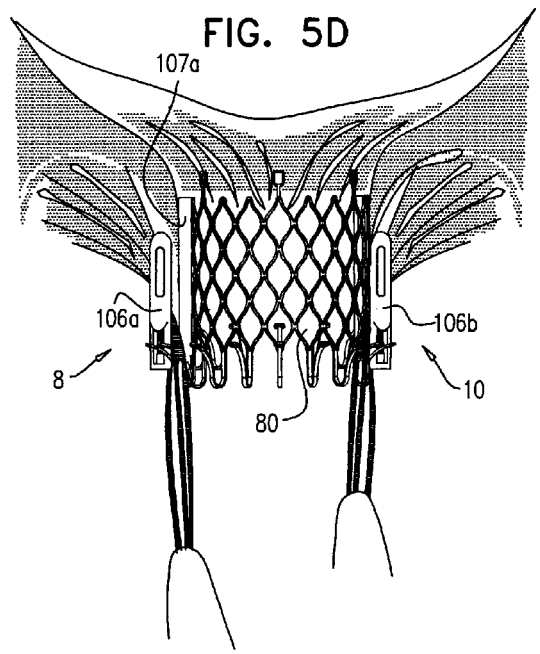

Subsequent to the placement of grasping elements 106a and 106b distally to native commissures 8 and 10, prosthetic valve 80 is advanced toward native valve 5, as shown in FIG. 5B. For example, the prosthetic valve may be advanced over delivery lumens 27a and 27b, as shown. The prosthetic valve is placed at the native valve and, subsequently, the grasping elements are retracted proximally toward commissures 8 and 10, as shown in the transition from FIG. 5B to FIG. 5C. For some applications, the grasping elements are coupled to valve 80 via coupling tubes 107a and 107b, the coupling tubes being coupled to the sides of the valve, as shown. The grasping elements are closed such that the native commissures are grasped and sealed by the grasping elements, as shown in FIG. 5D. Typically, the grasping elements define two surfaces that are hingedly coupled to each other. For example, the grasping elements may include forceps, as shown. The grasping elements are closed by closing the surfaces about the hinge, with respect to one another.

Typically, grasping elements 106a and 106b facilitate sealing of native commissures 8 and 10, thereby reducing retrograde blood flow via the commissures, relative to retrograde blood flow in the absence of the grasping elements. Further typically, the sealing of the native commissures facilitates anchoring of the prosthetic valve to native valve 5.

Although not shown, for some applications, prosthetic valve support 40 is used in addition to grasping elements 106a and 106b, in order to anchor prosthetic valve 80 to native valve 5. For some applications, the grasping elements are used to anchor and/or provide sealing for prosthetic valve support 40 (instead of, or in addition to, being used to anchor prosthetic valve 80, as shown). For such applications, generally similar techniques are used to those described with respect to the use of the grasping elements for anchoring the prosthetic valve, mutatis mutandis.

Figure 6B:
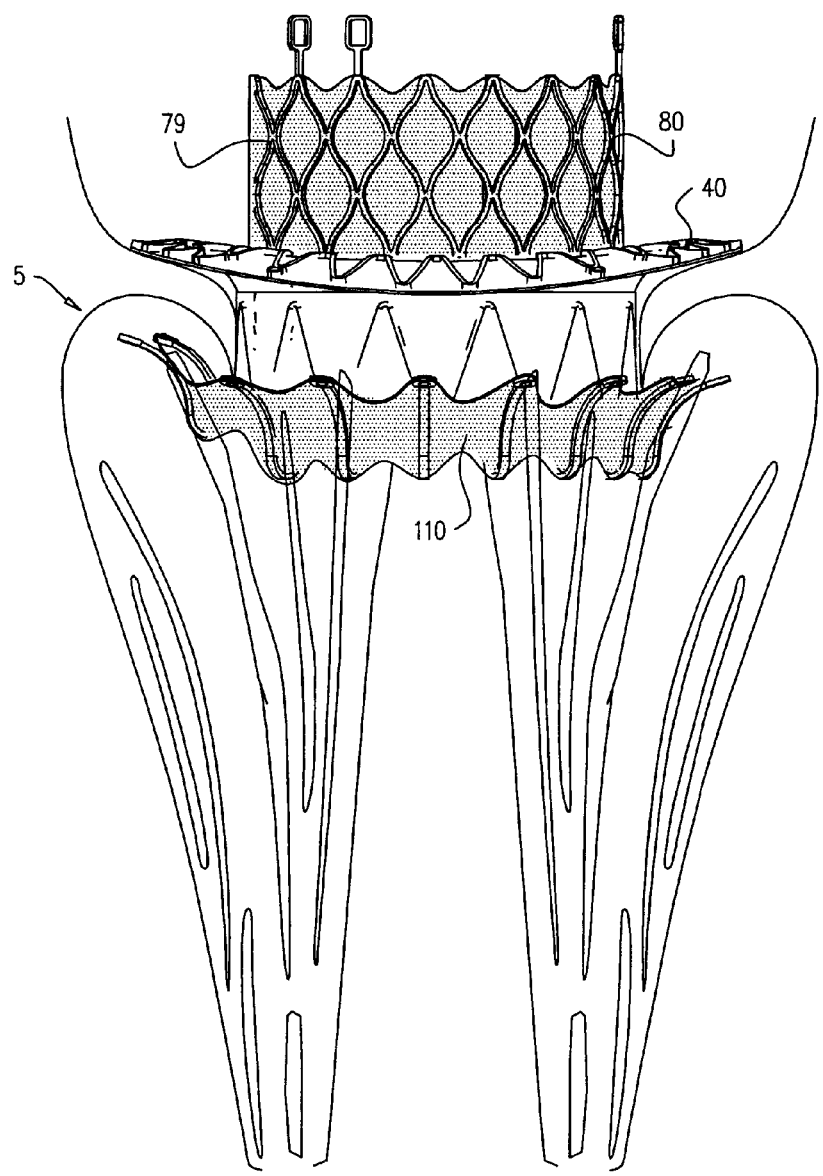

Reference is now made to FIGS. 6A-B, which are schematic illustrations of prosthetic valve 80, the prosthetic valve comprising a sealing material 110 on an outer surface of the valve, in accordance with some applications of the present invention. For some applications, prosthetic valve 80 is used in conjunction with prosthetic valve support 40, as described hereinabove. The techniques for implanting prosthetic valve 80 as shown in FIGS. 6A-B are generally similar to those described hereinabove. Typically, sealing material 110 seals the interface between the prosthetic valve and native valve 5. The sealing material reduces retrograde blood flow from ventricle 6 into atrium 4, relative to retrograde blood flow in the absence of the sealing material. Typically, the sealing material is composed of latex, dacron, and/or any other suitable biocompatible material. The sealing material is typically placed around at least a portion of expandable frame 79 of the prosthetic valve so as to form a webbing between struts of the expandable frame.

Reference is now made to FIGS. 7A-F, which are schematic illustrations of a guide wire delivery system, in accordance with some applications of the present invention. As described hereinabove (e.g., with reference to FIGS. 2C-F), for some applications, guide members 21a and 21b, function as valve support guide members, by support 40 being slid along guide members 21a and 21b. For some applications, only one guide member 21 is looped through commissures 8 and 10 in a manner in which the guide member defines a looped portion between commissures 8 and 10 (i.e., a portion of the guide member that is disposed in a ventricle 6 of heart 2), and first and second free ends, which are disposed and accessible at a site outside the body of the patient. For such applications, the guide member defines portions 21a and 21b.

Figure 7A:
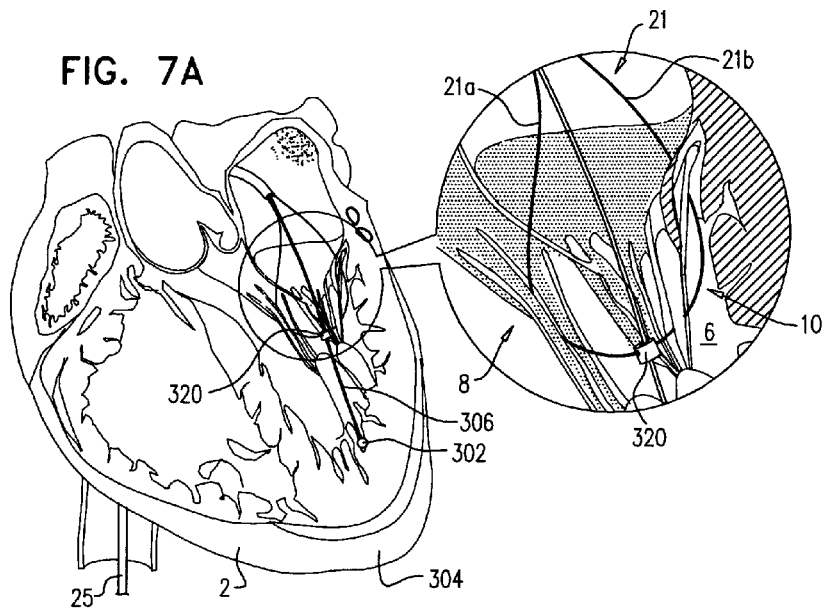

For some applications, an anchor 302 is advanced toward the vicinity of apex 304 of heart 2, via sheath 25, and is anchored to the vicinity of the apex, as shown in FIG. 7A. A guidewire 306 extends proximally from anchor. Guide member 21 passes through a guide member tube 320, the guide member tube being coupled to guidewire 306. Guide member 21 is pushed distally. Guide member tube 320 is unable to advance distally over guidewire 306, due to the coupling of the guide member tube to the guidewire. Therefore, the pushing of guide member 21 distally, causes portions 21a and 21b to spread apart from one another and to be pushed against commissures 8 and 10 of native valve 5. Portions 21a and 21b are then used to guide valve support 40 to the commissures, as shown in FIGS. 7B-C, using generally similar techniques to those described hereinabove, except for the differences described hereinbelow.

Figure 7B:
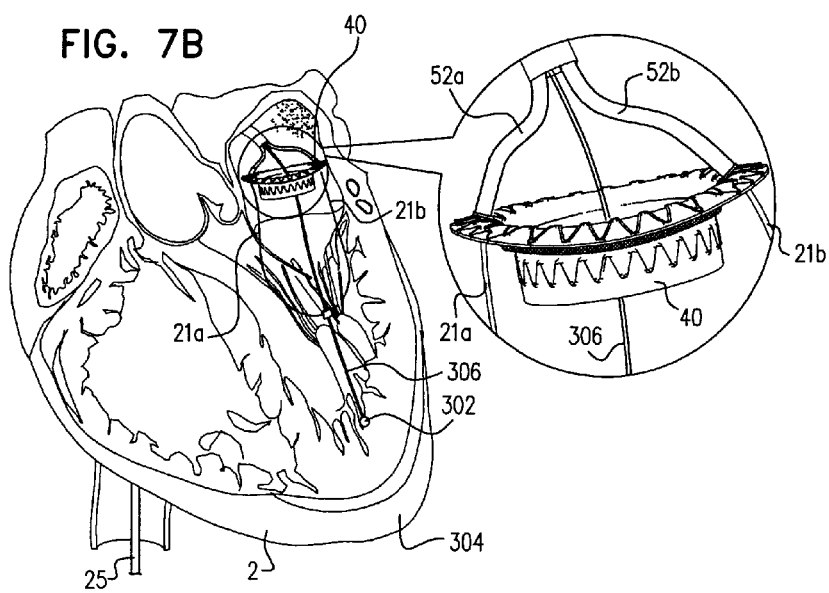
Figure 7C:
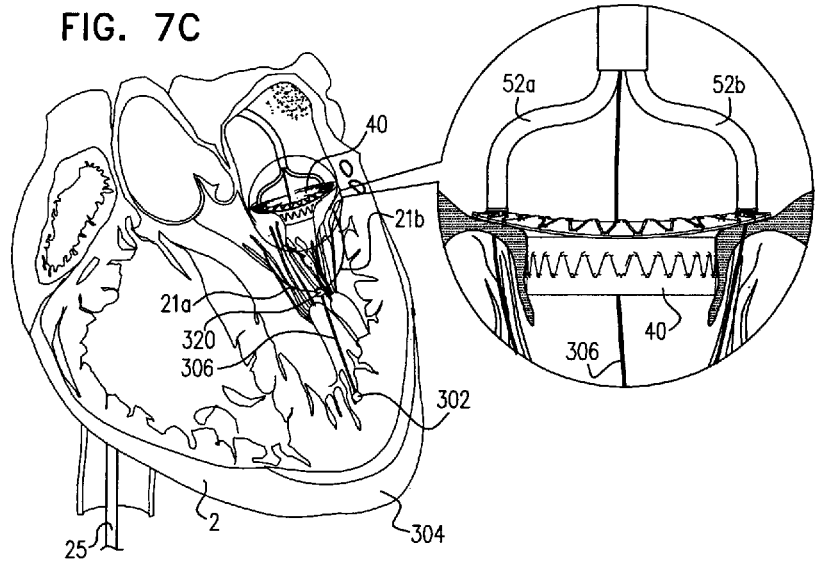

As shown in FIG. 7B, valve support 40 is slid over guide member portions 21a and 21b, by pushing elements 52a and 52b. Since the guide member portions are positioned at commissures 8 and 10, the guide member portions guide the distal ends of pushing elements 52a and 52b, such that the pushing elements push the valve support against the commissures, as shown in FIG. 7C.

Figure 7D:
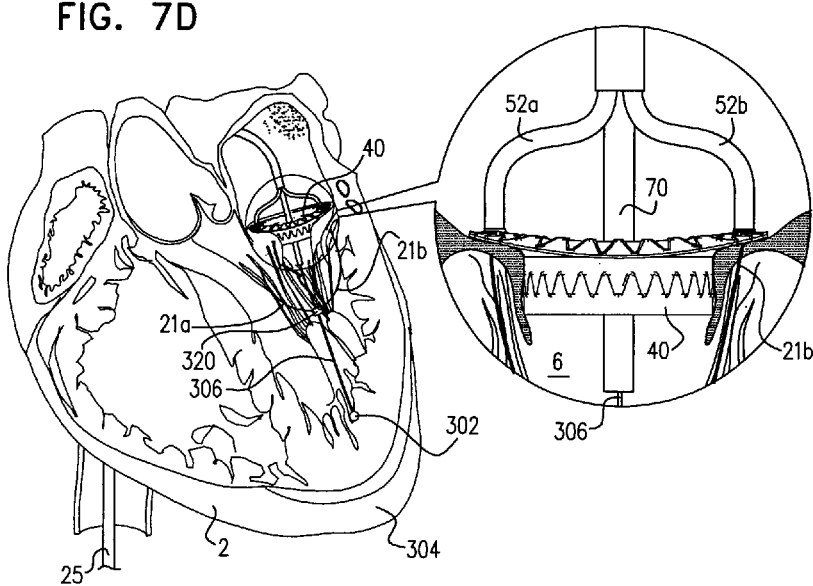

Subsequent to the placement of valve support 40 at the native valve, prosthetic atrioventricular valve 80 is coupled to valve support 40. For some applications, pushing elements 52a and 52b continue to push the valve support against the native valve, during the coupling of the prosthetic valve to the valve support. As described hereinabove, overtube 70 is advanced into ventricle 6, as shown in FIG. 7D. FIG. 7E shows prosthetic valve having been partially deployed in the ventricle. Following the partial deployment of valve 80 in ventricle 6, overtube 70 is pulled proximally to pull valve 80 proximally such that cylindrical element 42 and/or annular element 44 of valve support 40 surrounds a proximal portion of prosthetic valve 80. Valve 80 has a tendency to expand such that valve 80 is held in place with respect to valve support 40 responsively to radial forces acted upon valve support 40 by prosthetic valve 80. During the pulling back of overtube 70, pushing elements 52a and 52b push valve support 40 against the valve, thereby providing a counter force against which overtube 70 is pulled back. For some applications, the pushing of the valve support against the commissures is such that it is not necessary to use anchors for anchoring the valve support to the native valve during the coupling of the prosthetic valve to the valve support. Alternatively, in addition to the pushing elements providing a counter force against which the prosthetic valve is pulled, anchors are used to anchor the valve support to the native valve during the coupling of the prosthetic valve to the valve support.

As described hereinabove, valve 80 comprises a plurality of distal protrusions 84. When valve 80 is pulled proximally, as described hereinabove, protrusions 84 ensnare and engage the native leaflets of the atrioventricular valve. By the ensnaring of the native leaflets, protrusions 84 sandwich the native valve between protrusions 84 and prosthetic valve support 40. Such ensnaring helps further anchor prosthetic valve 80 to the native atrioventricular valve.

For some applications, as described hereinabove, protrusions 84 are such as to (a) prevent proximal migration of the valve into the patient's atrium, while (b) allowing movement of the native leaflets with respect to the frame of the prosthetic valve. For example, the protrusions may have the aforementioned functionalities by having lengths of less than 5 mm and/or by a total width of each set of protrusions corresponding to respective leaflets of the native valve being less than 5 mm. For example, the valve may include a single protrusion corresponding to each leaflet of the native valve, the width of each of the single protrusions being less than 1 mm. Thus, the valve may be stopped from proximally migrating into the atrium, by the protrusions preventing the distal end of the valve from migrating further proximally than edges of native leaflets of the valve. Furthermore, the protrusions may allow movement of the native leaflets with respect to the frame of the prosthetic valve by not generally squeezing the native leaflets between the protrusions and the frame of the valve. For some applications, by allowing movement of the native leaflets with respect to the frame of the prosthetic valve, sealing of the native leaflets against the outer surface of the frame of the prosthetic valve is facilitated, in accordance with the techniques described hereinbelow with reference to FIG. 10.

Subsequent to the placement of the prosthetic valve at the native valve, sheath 25, overtube 70, pushing elements 52a and 52b, guide member 21, anchor 302, and guidewire 306 are removed from the patient's body, as shown in FIG. 7F, which shows the prosthetic valve in its deployed state. For some applications, in order to remove guide member 21 from the patient's body, guide member portions 21a and 21b are decoupled from guide member tube 320. For example, the guide member portions may be coupled to the guide member tube via threading, the guide member portions being decoupled from the guide member tube by unscrewing the guide member portions from the guide member tube.

Figure 8C:
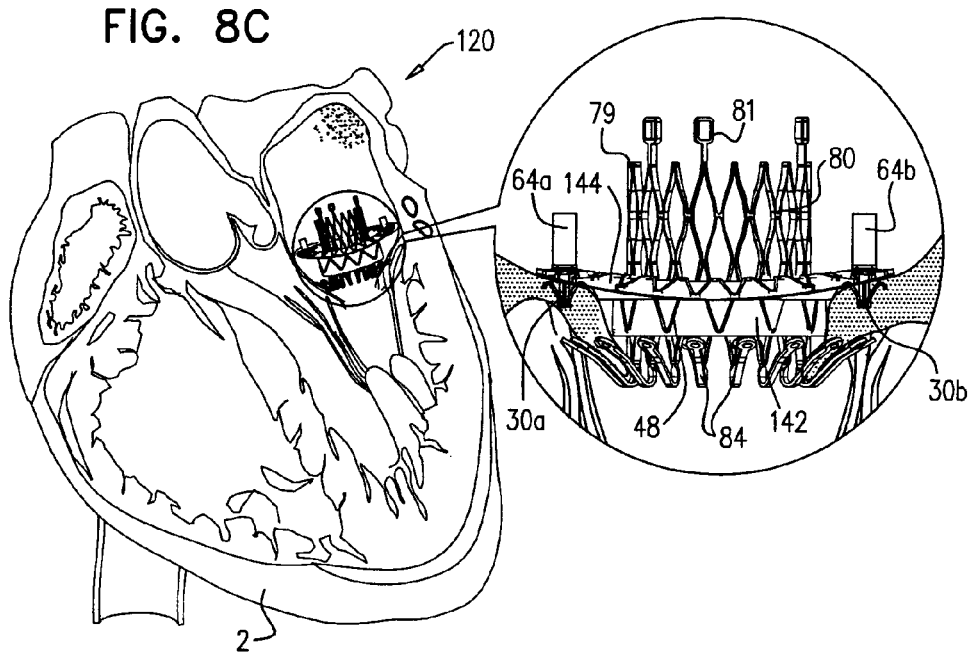

Reference is now made to FIGS. 8A-C which are schematic illustrations of a system 120 comprising an invertible valve support 140, in accordance with some applications of the present invention. Invertible valve support 140 is identical to valve support 40 described herein, with the exception that the cylindrical element of valve support 140 is invertible, as is described hereinbelow. Additionally, the method of advancing toward and implanting valve support 140 at annulus 11 is identical to the methods of advancing toward and implanting valve support 40 at annulus 11, as described hereinabove.

Valve support 140 comprises an annular element 144 (that is identical to annular element 44 described hereinabove) and a cylindrical element 142. Cylindrical element 142 has a first end 150, a second end 152, and a cylindrical body 153 disposed between first and second ends 150 and 152. Cylindrical element 142 is attached to annular element 144 at first end 150 of cylindrical element 142.

During and following implantation of support 140 at annulus 11, as shown in FIG. 8A, cylindrical element 142 is disposed above annular element 144 in a manner in which second end 152 and cylindrical body 153 are disposed above annular element 144 and within atrium 4. One or more elongate guide members 146a and 146b are reversibly coupled to cylindrical element 142 in a vicinity of second end 152. Elongate guide members 146a and 146b facilitate (a) advancement of prosthetic valve 80 therealong and toward valve support 140, and (b) inversion of cylindrical element 142 toward ventricle 6 when at least a portion of valve 80 is deployed within ventricle 6 (as shown in FIG. 8B).

The configuration of valve support 140 as shown in FIG. 8A (i.e., the configuration in which cylindrical element 142 is disposed within atrium 4) eliminates the obstruction of native valve 5 and of leaflets 12 and 14 by any portion of valve support 140. In this manner, valve support 140 may be implanted at valve 5 while valve 5 resumes its native function and leaflets 12 and 14 resume their natural function (as shown by the phantom drawing of leaflets 12 and 14 in FIG. 8A which indicates their movement). This atrially-inverted configuration of valve support 140 reduces and even eliminates the amount of time the patient is under cardiopulmonary bypass. Only once prosthetic valve 80 is delivered and coupled to valve support 140 and cylindrical element 142 is thereby ventricularly-inverted, native leaflets 12 and 14 are pushed aside (FIG. 8B).

FIG. 8B shows the inversion of cylindrical element 142 by the partial positioning and deployment of prosthetic valve 80 within ventricle 6. Elongate guide members 146a and 146b are reversibly coupled to prosthetic valve 80 and extend within overtube 70. Following the full deployment of valve 80 and the coupling of valve 80 to valve support 140, elongate guide members 146a and 146b are decoupled from prosthetic valve 80 and from cylindrical element 142. For example, a cutting tool may be used to decouple elongate members 146a and 146b from the valve support 140. Alternatively, elongate members 146a and 146b may be looped through the cylindrical element 142, such that both ends of each elongate member 146a and 146b remain outside of the patient's body. The operating physician decouples elongate members 146a and 146b from valve support 140 by releasing one end of each of elongate members 146a and 146b and pulling on the other end, until elongate members 146a and 146b are drawn from valve support 140 and removed from within the body of the patient.

FIG. 8C shows prosthetic valve 80 coupled to valve support 140. Valve 80 is identical to the valve described hereinabove.

Reference is now made to FIGS. 9A-E, which are schematic illustrations of the advancement of an invertible prosthetic valve support 300 toward a native atrioventricular valve of a patient, and inversion of the valve support, in accordance with some applications of the present invention. Prosthetic valve support 300 is used to anchor prosthetic valve 80 to native valve 5 in a generally similar manner to that described with reference to prosthetic valve support 40.

Figure 9A:
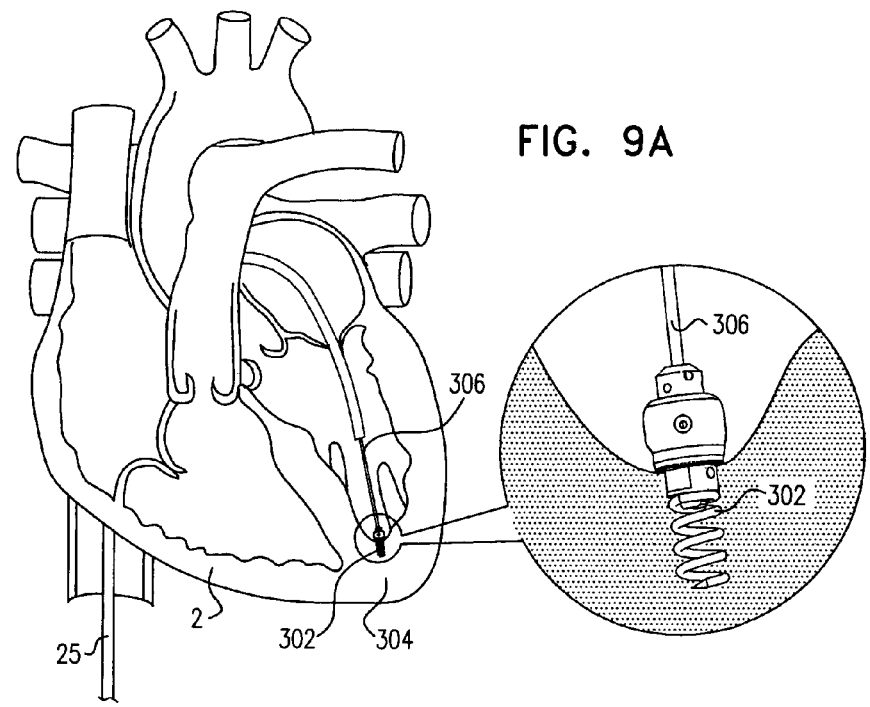
FIGS. 9A-D are schematic illustrations of the advancement of an invertible prosthetic valve support toward a native atrioventricular valve of a patient, in accordance with some applications of the present invention.
Figure 9B:
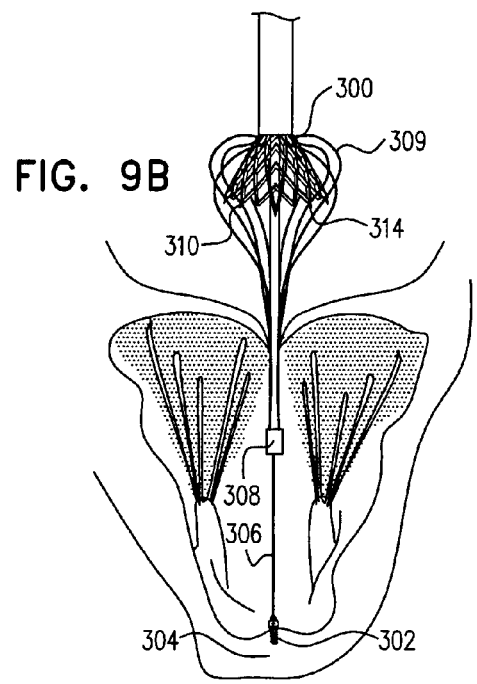
Figure 9C:
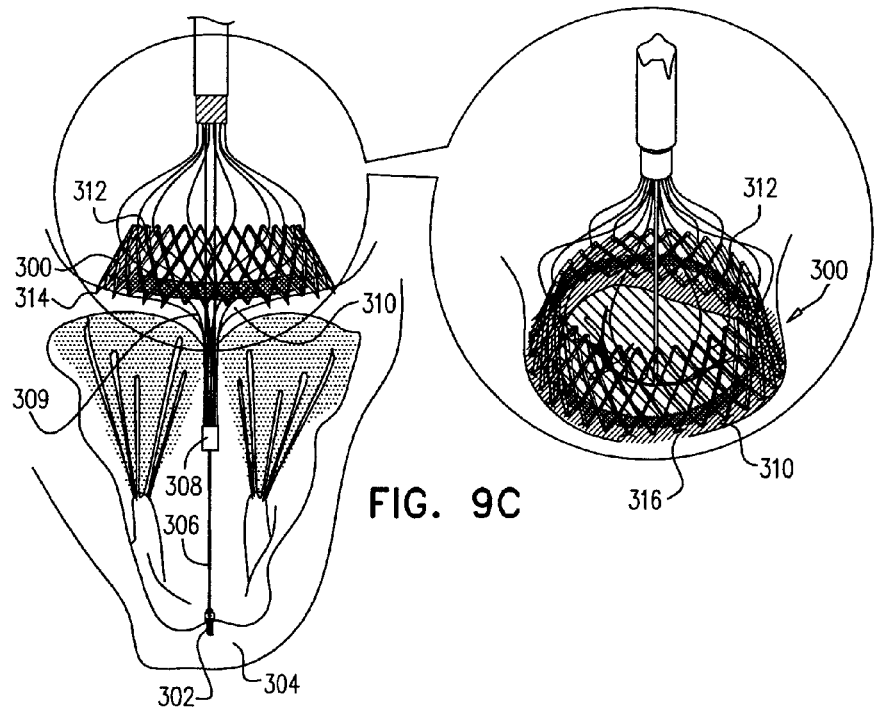
Figure 9D:
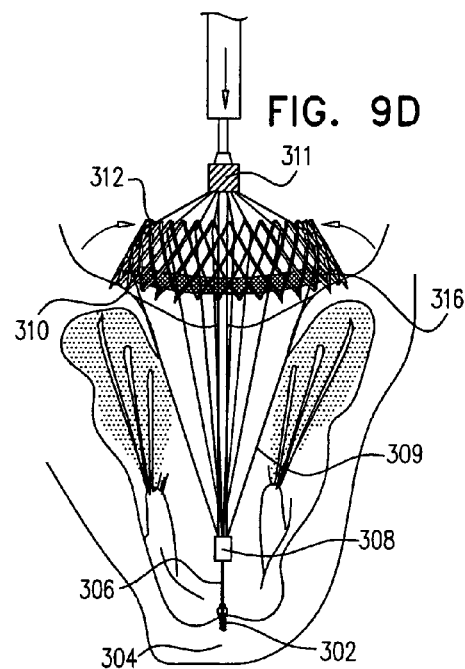

During a typical procedure, anchor 302 is advanced toward the vicinity of apex 304 of heart 2, via sheath 25, and is anchored to the vicinity of the apex, as shown in FIG. 8A. A guidewire 306 extends proximally from anchor. A distal tensioning element 308 (e.g., a plunger) is advanced over guidewire 306 into ventricle 6, and prosthetic valve support 300 is advanced out of the distal end of sheath 25, as shown in FIG. 9B. A first end 310 of prosthetic valve support 300 (which at this stage is the distal end of the prosthetic valve support), comprises barbs 314 (shown in FIG. 9B), or other anchoring elements for anchoring the first end of the prosthetic valve support to tissue of native valve 5. Prosthetic valve support 300 is pushed distally such that the barbs are pushed into the native valve tissue, thereby anchoring the first end of the prosthetic valve support to the native valve, as shown in FIG. 9C. A plurality of wires 309 pass from distal tensioning element 308 to a proximal tensioning element 311 (shown in FIG. 9D), via a second end 312 of valve support 300 (which at this stage is the proximal end of the prosthetic valve support). For some applications, a sealing element 316 is disposed circumferentially around a surface of the invertible prosthetic valve support that is initially an inner surface of the invertible prosthetic valve support (a shown in FIGS. 8A-D). For example, the sealing material may be latex, dacron, or another suitable biocompatible sealing material.

Subsequent to the anchoring of first end 310 of prosthetic valve support 300 to native valve tissue (as shown in FIG. 9C), distal tensioning element 308 is further advanced distally into ventricle 6, and proximal tensioning element 311 is advanced toward the ventricle. As shown in the transition from FIG. 9D-F, as the proximal tensioning element passes through the valve support, wires 309 cause valve support 300 to invert, by pulling second end 312 of the valve support through first end 310 of the valve support. Subsequent to the inversion of the valve support, sealing material 316 is disposed circumferentially around the outside of the valve support, thereby providing a seal at the interface between valve support 300 and native valve 5.

Figure 9G:
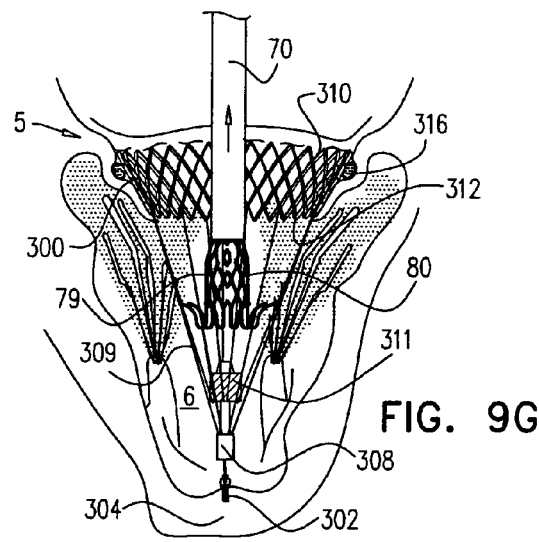
Figure 9H:
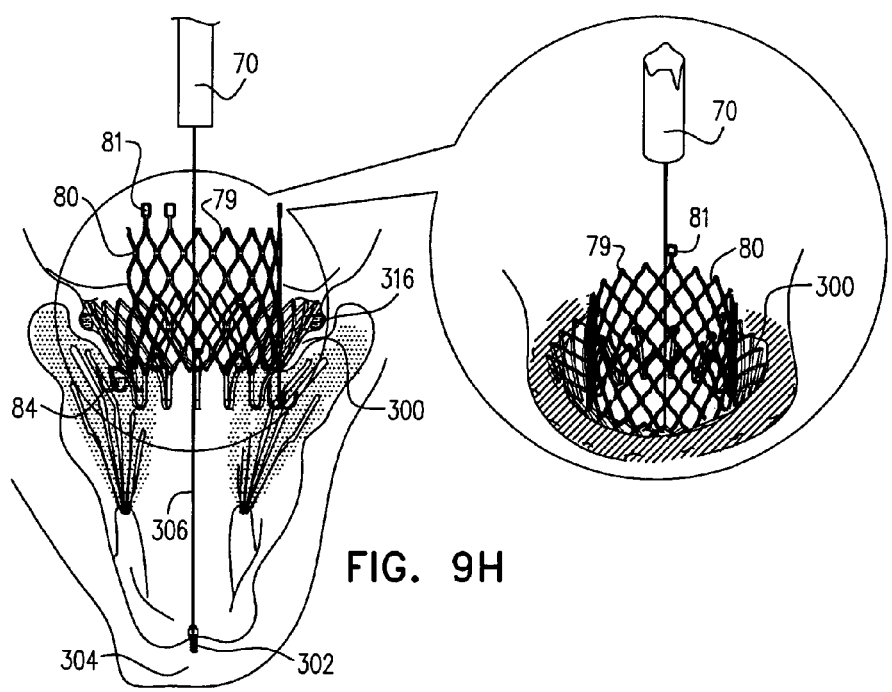

Reference is now made to FIGS. 9G-H, which are schematic illustrations of the deployment of prosthetic valve 80 and the coupling of the prosthetic valve to invertible valve support 300, in accordance with some applications of the present invention.

The deployment of prosthetic valve 80 is generally similar to the techniques described hereinabove with reference to FIGS. 2H-J. The valve is partially deployed in ventricle 6, via overtube 70. Following the partial deployment of valve 80 in ventricle 6, overtube 70 is pulled proximally (as shown in FIG. 8G) to pull valve 80 proximally such that valve support 300 surrounds a proximal portion of prosthetic valve 80, as shown in FIG. 8H. Valve 80 has a tendency to expand such that valve 80 is held in place with respect to valve support 300 responsively to radial forces acted upon valve support 300 by prosthetic valve 80.

As described hereinabove, for some applications, valve 80 comprises a plurality of distal protrusions 84. When valve 80 is pulled proximally, protrusions 84 ensnare and engage the native leaflets of the atrioventricular valve. By the ensnaring of the native leaflets, protrusions 84 sandwich the native valve between protrusions 84 and prosthetic valve support 300. Such ensnaring helps further anchor prosthetic valve 80 to the native atrioventricular valve.

For some applications, as described hereinabove, protrusions 84 are such as to (a) prevent proximal migration of the valve into the patient's atrium, while (b) allowing movement of the native leaflets with respect to the frame of the prosthetic valve. For example, the protrusions may have the aforementioned functionalities by having lengths of less than 5 mm, and/or by a total width of each set of protrusions corresponding to respective leaflets of the native valve being less than 5 mm. For example, the valve may include a single protrusion corresponding to each leaflet of the native valve, the width of each of the single protrusions being less than 1 mm. Thus, the valve may be stopped from proximally migrating into the atrium, by the protrusions preventing the distal end of the valve from migrating further proximally than edges of native leaflets of the valve. Furthermore, the protrusions may allow movement of the native leaflets with respect to the frame of the prosthetic valve by not generally squeezing the native leaflets between the protrusions and the frame of the valve. For some applications, by allowing movement of the native leaflets with respect to the frame of the prosthetic valve, sealing of the native leaflets against the outer surface of the frame of the prosthetic valve is facilitated, in accordance with the techniques described hereinbelow with reference to FIG. 10.

Additionally, as shown in FIG. 9H, and as described hereinabove, valve 80 comprises one or more coupling elements 81 (for example, a plurality of coupling elements, as shown) at the proximal end of valve 80. Overtube 70, which facilitates the advancement of prosthetic valve 80, is reversibly coupled to valve 80, via coupling elements 81.

Subsequent to the coupling of valve 80 to valve support 300, overtube 70, distal and proximal tensioning elements 308 and 311, and wires 309 are removed from the patient's body, via sheath 25. Typically, wires 309 are cut, in order to facilitate the removal of the wires from the patient's body. Guidewire 306 and anchor 302 are removed from the patient's body by detaching the anchor from apex 304, and withdrawing the anchor and the guidewire, via sheath 25.

Reference is now made to FIG. 10, which is a schematic illustration of prosthetic valve 80, for placing inside atrioventricular valve 5 of the patient, in accordance with some applications of the present invention. The expandable frame 79 of the prosthetic valve has a diameter d, and a corresponding cross-sectional area. Native annulus 11, which is typically saddle-shaped, defines an area A, as shown. For some applications, area A, which is defined by the native annulus is measured, e.g., using a measuring ring. A prosthetic valve is chosen to be placed in the annulus, the cross-sectional area of the prosthetic valve being less than 90% (e.g., less than 80%, or less than 60%) of area A. For some applications, diameter d of the prosthetic valve is less than 25 mm, e.g., less than 20 mm, and/or more than 15 mm, e.g., 15-25 mm. For some applications, placing a prosthetic valve inside the native valve with the dimensions of the native valve annulus and the prosthetic valve as described, facilitates sealing of the prosthetic valve with respect to the native valve, by the native valve leaflets closing around the outer surface of the prosthetic valve.

For some applications, a prosthetic valve support 40 that includes annular element 44 (e.g., as shown in FIGS. 14A-C) is chosen to be placed at the annulus, the annular element defining an inner cross-sectional area that is less than 90% (e.g., less than 80%, or less than 60%) of area A. Prosthetic valve 80 is deployed at the native valve by coupling the prosthetic valve to the prosthetic valve support at the location, responsively to radial forces acted upon the valve support by the expandable frame, by facilitating expansion of the expandable frame, as described herein. The cross-sectional area defined by the expandable frame of the prosthetic valve, upon expansion of the expandable frame, is limited by the cross-sectional area defined by the annular element of the prosthetic valve support to less than 90% (e.g., less than 80%, or less than 60%) of area A. For some applications, placing a prosthetic valve support at the annulus with the dimensions of the native valve annulus and valve support 40, as described, facilitates sealing of the prosthetic valve with respect to the native valve, by the native valve leaflets closing around the outer surface of the prosthetic valve.

Typically, placing a prosthetic valve inside the native valve with the dimensions of the native valve annulus, the prosthetic valve 80, and/or valve support 40 as described in the above paragraphs, facilitates sealing of the prosthetic valve with respect to the native valve. For some applications, the sealing is facilitated by the native leaflets being pushed against, and closing against, the outer surface of the frame of the valve during systole, in a similar manner to the manner in which native valve leaflets coapt during systole, in a healthy mitral valve. Typically, as the diameter of the prosthetic valve is increased, the length of the native leaflets that is pushed against the outer surface of the valve during systole is increased, thereby enhancing the sealing of the native leaflets with respect to the frame of the prosthetic valve. However, beyond a given diameter, as the diameter of the prosthetic valve is increased, the native valve leaflets are pushed apart at the commissures, thereby causing retrograde leakage of blood through the commissures. Therefore, in accordance with some applications of the present invention, prosthetic valve 80, and/or valve support 40 are chosen such that the cross-sectional area of the prosthetic valve when expanded inside the valve support is less than 90% (e.g., less than 80%, or less than 60%) of area A. Thus the valve support facilitates sealing of the prosthetic valve with respect to the native valve, by the native valve leaflets closing around the outer surface of the prosthetic valve, while not causing retrograde leakage of blood through the commissures.

For some applications, in order to facilitate the sealing of the native valve around the outer surface of the prosthetic valve, a material is placed on the outer surface of the prosthetic valve in order to provide a sealing interface between the prosthetic valve and the native valve. For example, a smooth material that prevents tissue growth (e.g., polytetrafluoroethylene (PTFE), and/or pericardium) may be placed on the outer surface of the prosthetic valve. Alternatively or additionally, a material that facilitates tissue growth (such as dacron) may be placed on the outer surface of the prosthetic valve, in order to (a) act as a sealing interface between the native valve and the prosthetic valve, and (b) facilitate tissue growth around the prosthetic valve to facilitate anchoring and/or sealing of the prosthetic valve.

Reference is now made to FIGS. 11A-D, which are schematic illustrations of prosthetic valve 80, in accordance with some applications of the present invention. For some applications, protrusions 84 are disposed on the valve on portions 400 of the valve that are placed adjacent to the anterior and posterior leaflets of the native valve, and the valve does not includes protrusions on portions 402 of the valve that are placed adjacent to the commissures of the native valve.

Figure 11D:
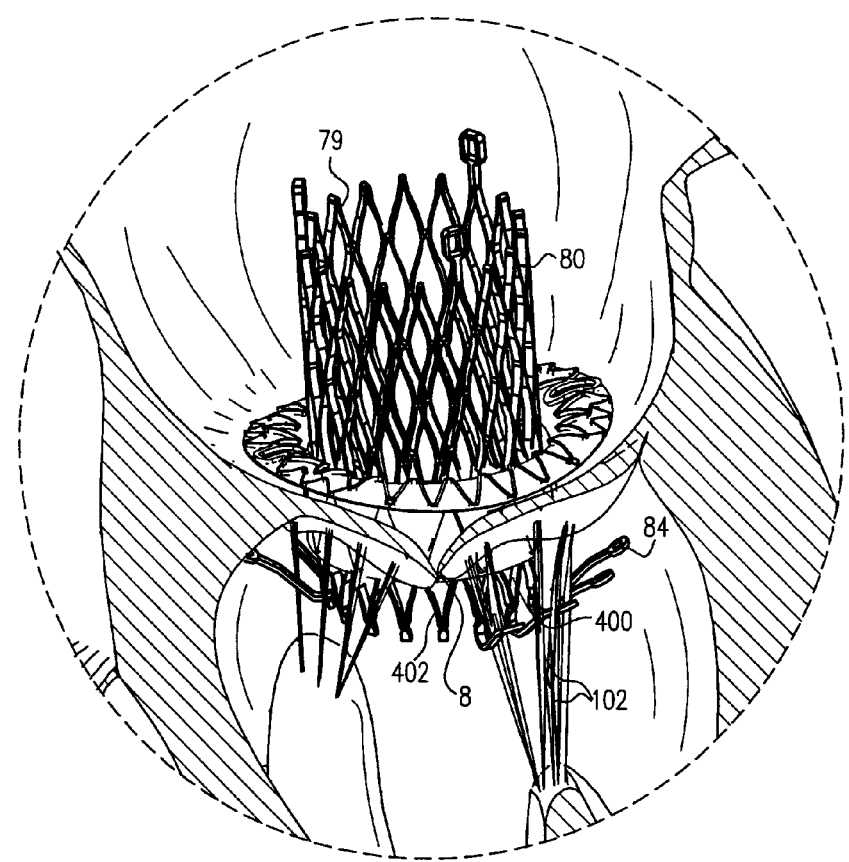

FIGS. 11B-D show bottom views (i.e., views of the distal ends) of respective configurations of prosthetic valve 80 and protrusions 84. The protrusions converge from the proximal ends 404 of the protrusion to the distal ends 406 of the protrusions. The protrusions are configured such as to ensnare chordae tendineae, and to pull the chordae tendineae toward each other when the prosthetic valve is pulled proximally, due to the convergence of the snares with respect to each other. FIG. 11D shows the prosthetic valve deployed at native valve 5. As shown, the protrusions ensnare chordae tendineae 102 of the patient. The protrusions facilitate sealing and anchoring of the prosthetic valve with respect to the native valve by pulling the chordae tendinae toward each other, as described. As described hereinabove, for some applications the prosthetic valve does not define protrusions 84 on portions 402 that are placed next to the native commissures, e.g., commissure 8, shown in FIG. 11D.

For some applications, as described hereinabove, protrusions 84 are such as to (a) prevent proximal migration of the valve into the patient's atrium, while (b) allowing movement of the native leaflets with respect to the frame of the prosthetic valve. For example, the protrusions may have the aforementioned functionalities by having lengths of less than 5 mm, and/or by a total width of each set of protrusions corresponding to respective leaflets of the native valve being less than 5 mm. For example, the valve may include a single protrusion corresponding to each leaflet of the native valve, the width of each of the single protrusions being less than 1 mm. Thus, the valve may be stopped from proximally migrating into the atrium, by the protrusions preventing the distal end of the valve from migrating further proximally than edges of native leaflets of the valve. Furthermore, the protrusions may allow movement of the native leaflets with respect to the frame of the prosthetic valve by not generally squeezing the native leaflets between the protrusions and the frame of the valve. For some applications, by allowing movement of the native leaflets with respect to the frame of the prosthetic valve, sealing of the native leaflets against the outer surface of the frame of the prosthetic valve is facilitated, in accordance with the techniques described hereinabove with reference to FIG. 10.

For some applications, a first set of protrusions 84 from the distal end of prosthetic valve 80 are disposed within a first circumferential arc with respect to a longitudinal axis of the prosthetic valve, on a first side of the distal end of the prosthetic valve, the first side of the distal end being configured to be placed adjacent to the anterior leaflet of the native valve. A second set of protrusions are disposed within a second circumferential arc with respect to a longitudinal axis of the prosthetic valve, on a second side of the distal end of the prosthetic valve, the second side of the distal end being configured to be placed adjacent to the posterior leaflet of the native valve.

The first and second sets of protrusions are disposed so as to provide first and second gaps therebetween at the distal end of the prosthetic valve. Typically, at least one of the gaps between the two sets of protrusions has a circumferential arc of at least 20 degrees (e.g., at least 60 degrees, or at least 100 degrees), and/or less than 180 degrees (e.g., less than 140 degrees), e.g., 60-180 degrees, or 100-140 degrees. Further typically, one or both of the first and second circumferential arcs defines an angle of at least 25 degrees (e.g., at least 45 degrees), and/or less than 90 degrees (e.g., less than 75 degrees), e.g., 25-90 degrees, or 45-75 degrees.

Valve guide members (e.g., guide members 21a and 21b, and/or delivery lumen 27a and 27b, as described hereinabove) are delivered to commissures of the native valve, and guide the valve such that the first and second circumferential arc are aligned with respective leaflets of the native valve and such that the first and second gaps are aligned with respective commissures of the native valve.

Reference is now made to FIGS. 12A-C, which are schematic illustrations of prosthetic valve 80, the valve defining distal protrusions 84 that are disposed sinusoidally around the circumference of the valve, in accordance with some applications of the present invention. For some applications the protrusions are shaped sinusoidally, in order to conform with the saddle-shape of native valve annulus 11, thereby facilitating the sandwiching of the native valve leaflets between the protrusions and valve support 40. As shown, the peaks of the sinusoid that is defined by the protrusions is disposed on portions 402 that are placed next to the native commissures and the troughs of the sinusoid is placed on portions of the valve that are placed in the vicinity of the centers of the anterior and posterior leaflets of the native valve. As shown in FIG. 12C, for some applications the distal end of the prosthetic valve defines a sinusoidal shape.

Figure 13A:
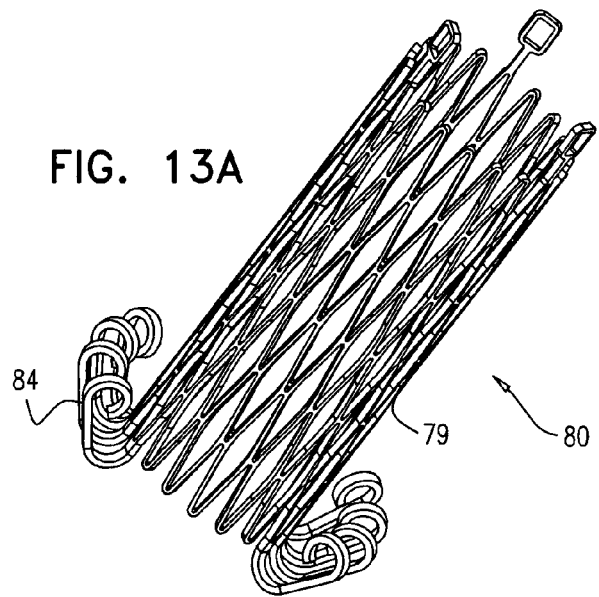
FIGS. 13A-E are schematic illustrations of respective configurations of a frame of a prosthetic valve, in accordance with some applications of the present invention.
Figure 13B:
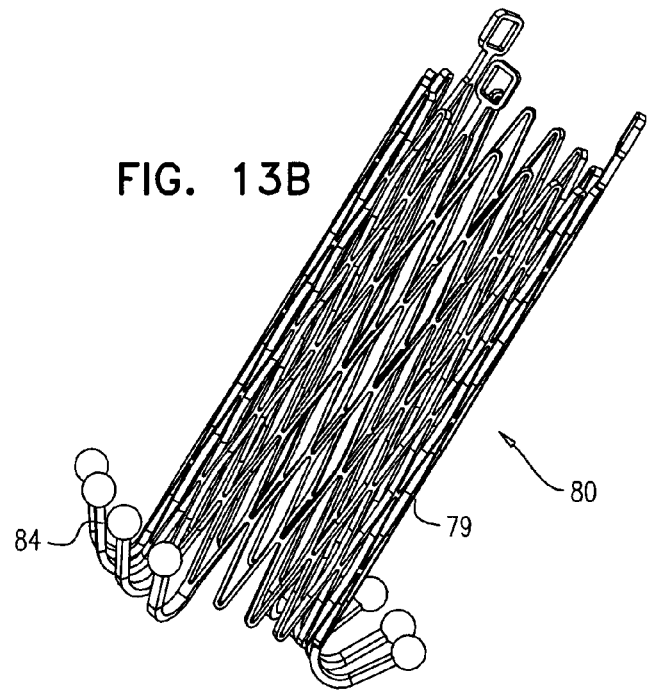
Figures 13C, 13D, 13E:
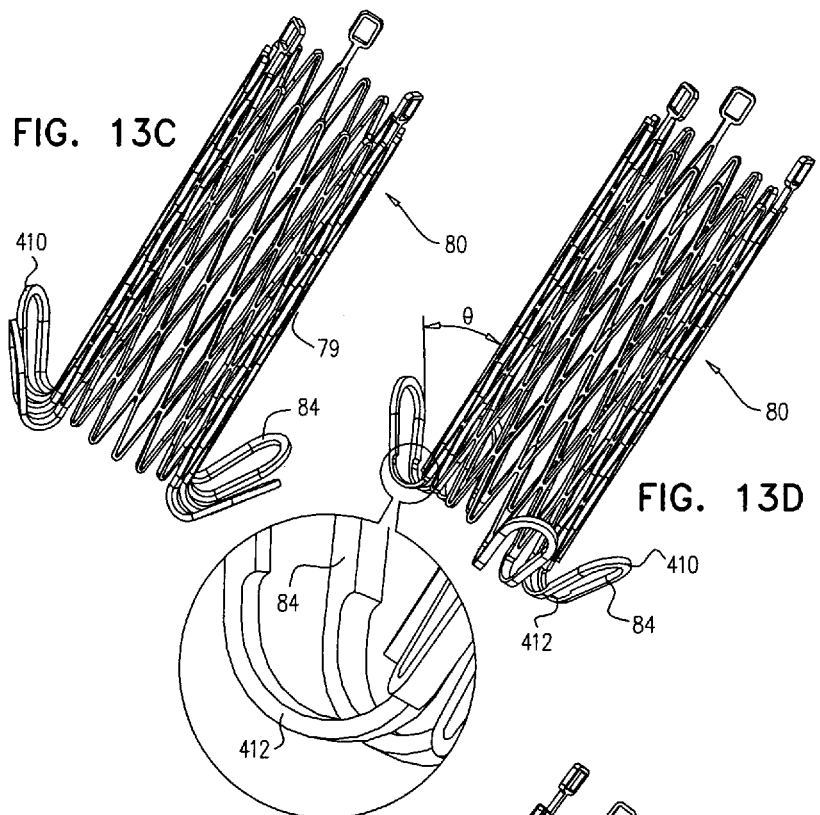

Reference is now made to FIGS. 13A-E, which are schematic illustrations of respective configurations of expandable frame 79 of prosthetic valve 80, in accordance with some applications of the present invention. As described hereinabove, for some applications, valve 80 defines distal protrusions 84 that are configured to facilitate sandwiching of the native valve leaflets between the protrusions and valve support 40. For some applications, tips of the distal protrusions are shaped so as to prevent the tips from piercing, and/or otherwise damaging, tissue of the native leaflets. For example, the tips of the protrusions may be curved, as shown in FIG. 13A. Or, the distal tips of the protrusions may be shaped as balls, as shown in FIG. 13, and/or a different rounded shape. For some applications, the distal tip of each of the protrusions is joined to the distal tip of an adjacent protrusion by an arch 410, as shown in FIGS. 13C and 13D.

For some applications, the protrusions are configured to be distally-facing during the insertion of prosthetic valve 80 into the subject's left ventricle. For example, the valve may be inserted through overtube 70 (shown in FIG. 7E, for example). The valve is crimped during the insertion of the valve through the overtube, and the protrusions are constrained in their distally-facing configurations by the overtube. The protrusions are pre-shaped such that in the resting state of the protrusions, the protrusions assume proximally-facing configurations, as shown in FIG. 13D, for example. Thus, upon emerging from overtube 70, the protrusions assume proximally-facing configurations. For some applications, when the protrusions assume the proximally-facing configurations, the protrusions are disposed at an angle theta (FIG. 13D) from expandable frame 79 of more than 40 degrees (e.g., more than 50 degrees), and/or less than 80 degrees (e.g., less than 70 degrees).

Typically, protrusions 84 are coupled to frame 79 of valve 80 at joints 412. For some applications, joints 412 are thinner than portions of the protrusions and of the frame surrounding the joints, as shown in FIG. 13D. For some applications, the thinness of the joints with respect to the surrounding portions facilitates the crimping of the protrusions into distally-facing configuration during the insertion of the valve into the heart.

For some applications, barbs 416 extend from a proximal portion of expandable frame 79 of valve 80, as shown in FIG. 13E. For example, the barbs may be configured to anchor the prosthetic valve to the native valve by piercing tissue of the native valve. Alternatively or additionally, the barbs may be configured to anchor the prosthetic valve to the valve support 40, by becoming coupled to portions of the valve support. For some applications the barbs protrude from the top-central corner of respective cells of expandable frame 79. Typically, when the prosthetic valve is crimped, the barbs fit within gaps of respective cells of the expandable frame, and do not substantially increase the crimping profile of the prosthetic valve, relative to a generally similar prosthetic valve that does not include barbs.

For some applications, the barbs are not generally used for coupling prosthetic valve support 80 to valve support 40. Rather, the prosthetic valve is coupled to the valve support by virtue of radial expansion of the prosthetic valve against annular element 44 of the valve support. Barbs 416 are used to prevent prosthetic valve from migrating distally into the patient's left ventricle, and/or to prevent valve support 40 from migrating proximally into the subject's left atrium.

For some applications (not shown), barbs protrude from coupling elements 81 of prosthetic valve 80, the barbs being generally similar in shape and function to that described with reference to barbs 416. For some applications (not shown), radially-inwardly facing barbs 45 protrude from annular element 44 of valve support 40, as shown in FIG. 14D. As described with reference to barbs 416, the barbs that protrude from annular element 44 may facilitate coupling of the prosthetic valve to the valve support. Alternatively or additionally, the barbs that protrude from annular element 44 are used to prevent prosthetic valve from migrating distally into the patient's left ventricle, and/or to prevent valve support 40 from migrating proximally into the subject's left atrium.

For some applications, a proximal end of expandable frame 79 of prosthetic valve 80 defines a larger cross-section area than more distal portions of the expandable frame. For example, the expandable frame may have a frustoconical shape, the walls of the expandable frame diverging from a distal end of the frame to a proximal end of the frame. Alternatively, the expandable frame may have a trumpet shape (i.e., the frame may be generally tubular, with a dilated proximal end). For some applications, the larger cross-sectional area of the proximal end of the frame prevents the prosthetic valve from migrating distally into the patient's left ventricle, and/or prevents valve support 40 from migrating proximally into the subject's left atrium.

Reference is now made to FIGS. 14A-D, which are schematic illustrations of respective configurations of prosthetic valve support 40, in accordance with some applications of the present invention. As described hereinabove, for some applications, the valve support comprises a collapsible skirt having a proximal annular element 44 and a distal cylindrical element 42 (e.g., as shown in FIG. 2D). Alternatively, the valve support does not include a distal cylindrical element. For example, the valve support may only include annular element 44. As described hereinabove, annular element 44 is configured to be placed around native annulus 11 of the native valve, and to extend at least partially into atrium 4 such that annular element 44 rests against the native annulus. Annular element 44 is typically too large to pass through the annulus, and may, for example, have an outer diameter of between 30 and 60 mm.

FIGS. 14A-D show annular element 44 of valve support 40 in respective configurations, in accordance with some applications of the present invention. For some applications, the annular element is D-shaped, as shown in FIG. 14A. Alternatively or additionally, the annular element has a generally round shape, as shown in FIGS. 14B-C. For some applications the annular element is asymmetrical. For example, FIG. 14B shows a generally rounded annular element that is wider on a first side 420 of the element than on a second side 422 of the element. Typically, the wider side of the annular element is placed on the anterior side of the native annulus. In accordance with some applications, the annular element is symmetrical, asymmetrical, oval, round, defines a hole that is centered with respect to the annular element, and/or defines a hole that is off-center with respect to the annular element. For some applications, the stiffness of the annular element varies around the circumference of the annular element.

For some applications, annular element 44 is asymmetrical, as shown in FIG. 14B. Typically, the asymmetry of the annular element is such that the center of the hole defined by the annular element is disposed asymmetrically (i.e., off-center) with respect to the center of the annular element, as defined by the outer perimeter of the annular element. For some applications, the asymmetric disposition of the center of the hole defined by the annular element is such that when the prosthetic valve is placed inside the annular element, the longitudinal axis of the prosthetic valve is disposed asymmetrically (i.e., off-center) with respect to the center of the annular element, as defined by the outer perimeter of the annular element. Typically, the annular element is shaped such that, when the annular element is placed on the patient's mitral annulus, and the prosthetic valve is expanded inside the annular element, the longitudinal axis of the prosthetic valve is disposed in the vicinity of the location at which the patient's native leaflets coapt (this location being off-center with respect to the patient's native mitral annulus).

For some applications (not shown), radially-inwardly facing barbs 45 protrude from annular element 44 of valve support 40, as shown in FIG. 14D. As described with reference to barbs 416 shown protruding from prosthetic valve 80 in FIG. 13E, the barbs that protrude from annular element 44 may facilitate coupling of the prosthetic valve to the valve support. Alternatively or additionally, the barbs that protrude from annular element 44 are used to prevent prosthetic valve from migrating distally into the patient's left ventricle, and/or to prevent valve support 40 from migrating proximally into the subject's left atrium. For some applications, some or all of barbs 102 are curved. Typically, the curved barbs curve away from the plane of annular element 40, such that, when implanted, barbs 102 point into the patient's atrium.

Typically, the annular element includes frame 48, the frame being covered at least in part with covering 49, e.g., fabric. Typically, the upper surface of annular element 44 is covered with fabric, for example, in order to provide a generally smooth surface for coming into contact with the patient's blood flow. Further typically, the lower surface of the annular element (i.e., the side of the annular element that is placed in contact with the native annulus) is not covered with fabric, for example, in order to reduce a crimped volume (or cross-sectional area) of the annular element, relative to the volume of the annular element if the lower surface of the annular element were covered in fabric. Typically, a thickness of the fabric layer is less than 0.2 mm, e.g., less than 0.1 mm, or less than 0.05 mm.

For some applications, the side of the annular element that is placed in contact with the native annulus is covered with the fabric, the fabric being configured to facilitate coupling of the annular element to the native annulus, by facilitating fibrosis at the interface between the annular element and the native annulus. For some applications, the upper surface of the annular element is not covered with fabric. For example, the upper surface may not be covered in fabric in order to reduce a crimped volume (or cross-sectional area) of the annular element, relative to the volume of the annular element if the upper surface of the annular element were covered in fabric.

For some applications, annular element 44 is not covered with fabric, and/or is not configured to form a seal against frame 79 of prosthetic valve 80. For some applications, the annular element is configured to allow leakage of blood between the annular element and frame 79 of prosthetic valve 80. For example, the annular element may be configured to allow leakage of blood through the interface between the annular element and the frame of the prosthetic valve, in order to accommodate a flow of blood between the patient's atrium and the patient's ventricle that is greater than can be accommodated by blood flowing through the leaflets of the prosthetic valve.

Reference is now made to FIGS. 15A-E, which are schematic illustrations of respective steps of a procedure for deploying a prosthetic valve, in accordance with some applications of the present invention. As described hereinabove and hereinbelow (for example, with reference to FIGS. 2A-K, 7A-F, 8A-C, 9A-H, and 16A-G), for some procedures, valve support 40 is placed on the valve annulus and, subsequently, prosthetic valve 80 is inserted into the subject's left ventricle through the valve support. Alternatively, any of the procedures described herein (for example, procedures described with reference to FIGS. 2A-K, 7A-F, 8A-C, 9A-H, and 16A-G) may be performed by first placing the prosthetic valve inside the subject's left ventricle, and, subsequently, deploying the valve support at the annulus. For example, FIGS. 15A-E show a procedure in which the prosthetic valve is placed inside the subject's left ventricle, and, subsequently, the valve support is deployed at the annulus.

As shown in FIG. 15A, for some applications, prosthetic valve 80 is placed in the subject's ventricle, before prosthetic valve support 40 is placed at the native valve. The prosthetic valve is typically placed in the left ventricle in an undeployed state, via overtube 70. Subsequently, the valve support is placed at the native valve using pushing elements, as shown in FIG. 15B. For some applications, three pushing elements 52a, 52b, and 52c are used to push the valve support against the native valve, as shown in FIG. 15B.

Figure 15C:
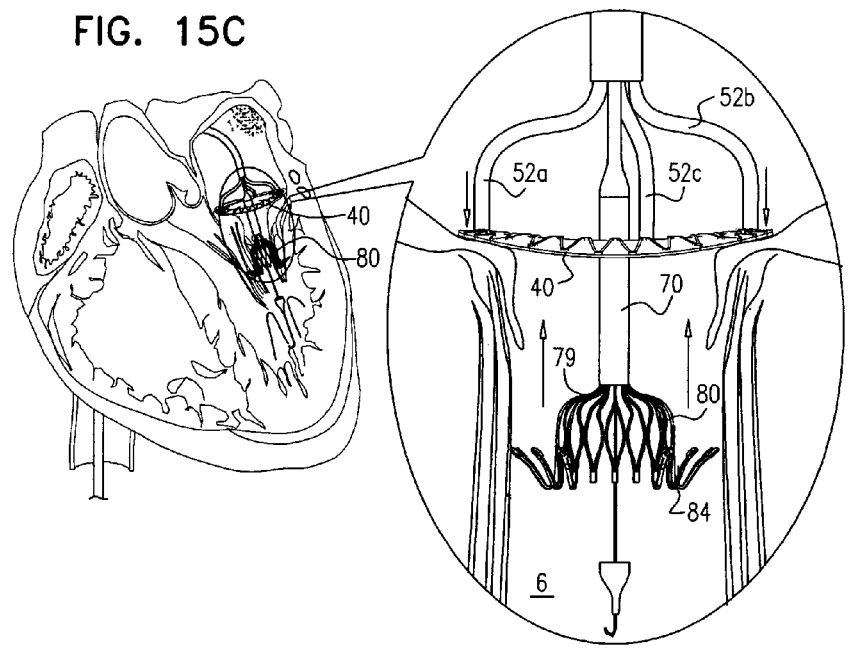

Subsequent to the placement of valve support 40 at the native valve, prosthetic valve 80 is coupled to valve support 40. For some applications, pushing elements 52a, 52b, and 52c continue to push the valve support against the native valve, during the coupling of the prosthetic valve to the valve support. FIG. 15C shows prosthetic valve having been partially deployed in the ventricle.

Figure 15D:
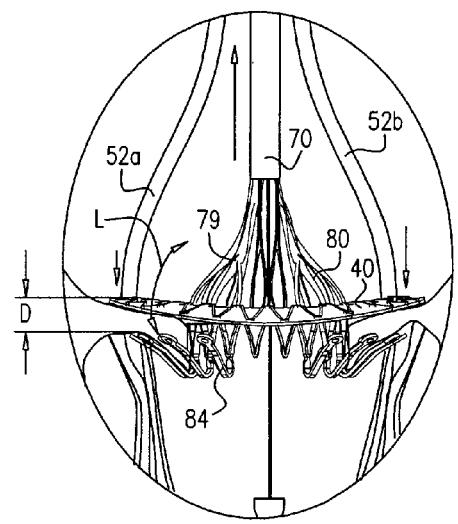

Following the partial deployment of valve 80 in ventricle 6, overtube 70 is pulled proximally to pull valve 80 proximally such that annular element 44 of valve support 40 surrounds a proximal portion of prosthetic valve 80, as shown in FIG. 15D. Valve 80 has a tendency to expand such that valve 80 is held in place with respect to valve support 40 responsively to radial forces acted upon valve support 40 by prosthetic valve 80. During the pulling back of overtube 70, pushing elements 52a, 52b, and 52c push valve support 40 against the valve, thereby providing a counter force against which overtube 70 is pulled back. For some applications, the pushing of the valve support against the commissures is such that it is not necessary to use anchors for anchoring the valve support to the native valve during the coupling of the prosthetic valve to the valve support. Alternatively, in addition to the pushing elements providing a counter force against which the prosthetic valve is pulled, anchors are used to anchor the valve support to the native valve during the coupling of the prosthetic valve to the valve support.

As described hereinabove, valve 80 comprises a plurality of distal protrusions 84. When valve 80 is pulled proximally, as described hereinabove, protrusions 84 ensnare and engage the native leaflets of the atrioventricular valve. By the ensnaring of the native leaflets, protrusions 84 sandwich the native valve between protrusions 84 and prosthetic valve support 40. Such ensnaring helps further anchor prosthetic valve 80 to the native atrioventricular valve.

It is noted with reference to FIG. 15D that, typically, annular element 44 of prosthetic valve support 40 defines an inner cross-sectional area thereof. As described hereinabove, prosthetic valve 80 includes expandable frame 79, and prosthetic leaflets 82. The expandable frame of the prosthetic valve is configured such that when the frame is in a non-constrained state thereof, the cross-sectional area of the frame, along at least a given portion L (shown in FIG. 15D) of the length of the frame, is greater than the inner cross-sectional area defined by the annular element of the prosthetic valve support. Typically, during a valve-deployment procedure, a location anywhere along portion L at which to couple the expandable valve to the prosthetic valve support is selected. In response thereto, the location along the portion of the expandable frame is aligned with the annular element of the prosthetic valve support. The expandable valve is then coupled to the prosthetic valve support at the location, responsively to radial forces acted upon the valve support by the expandable frame, by facilitating expansion of the expandable frame, when the location along the portion is aligned with the annular element of the prosthetic valve support.

As described hereinabove, for some applications, expandable frame 79 of prosthetic valve 80 has a frustoconical shape. For some applications, the prosthetic valve is coupled to valve support 40 responsively to radial forces acted upon the valve support by the expandable frame, when a given location along portion L is aligned with annular element 44 of the prosthetic valve support. For some applications, the portion immediately proximal to the given location along portion L has a greater cross-sectional area than the frame at the given location, due to the frustoconical shape of the expandable frame. Typically, the greater cross-sectional area of the portion immediately proximal to the given location along portion L relative to the cross-sectional area of the frame at the given location, reduces distal migration of the prosthetic valve toward the subject's left ventricle.

For some applications, the location along portion L at which to couple prosthetic valve 80 to valve support 40 is selected, based upon a distance D between protrusions 84 and annular element 44 that would result from coupling the prosthetic valve to the annular element at that location. For example, the location along portion L at which to couple prosthetic valve 80 to valve support 40 may be selected, such that distance D is such as to anchor the prosthetic valve to the patient's native valve by squeezing the patient's native valve leaflets between the protrusions and the annular element, and/or by ensnaring the patient's chordae tendinae between the protrusions and the annular element. Alternatively or additionally, the location along portion L at which to couple prosthetic valve 80 to valve support 40 may be selected, such that distance D is such that protrusions 84 (a) prevent proximal migration of the valve into the patient's atrium, while (b) allowing movement of the native leaflets with respect to the frame of the prosthetic valve. Typically, the location along portion L is selected such that distance D is such that the valve may be stopped from proximally migrating into the atrium, by the protrusions preventing the distal end of the valve from migrating further proximally than edges of native leaflets of the valve, while the protrusions allow movement of the native leaflets with respect to the frame of the prosthetic valve by not generally squeezing the native leaflets between the protrusions and the frame of the valve. For some applications, by allowing movement of the native leaflets with respect to the frame of the prosthetic valve sealing of the native leaflets against the outer surface of the frame of the prosthetic valve is facilitated, in accordance with the techniques described hereinabove with reference to FIG. 10.

Figure 15E:
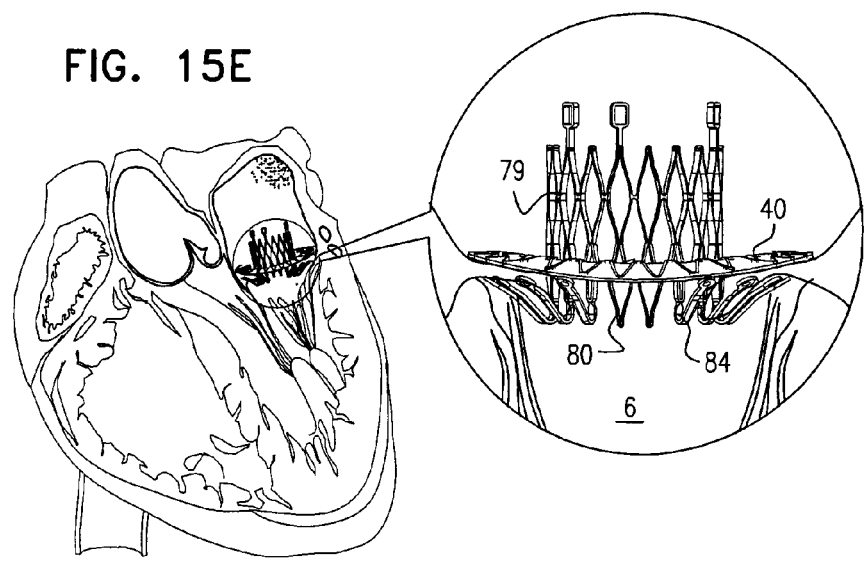

Subsequent to the placement of the prosthetic valve at the native valve, overtube 70, and pushing elements 52a, 52b, and 52c are removed from the patient's body, as shown in FIG. 15E, which shows the prosthetic valve in its deployed state.

Reference is now made to FIGS. 16A-G, which are schematic illustrations of respective steps of an alternative procedure for deploying prosthetic valve 80, in accordance with some applications of the present invention. As described hereinabove, with reference to FIGS. 7A-F, for some applications, a looped guide member 21 is looped through commissures 8 and 10 in a manner in which the guide member defines a looped portion between commissures 8 and 10. For some applications, the looped guide member has steering functionality. The steering functionality of the looped guide member is used to guide the guide member to the commissures, and/or to guide other portions of the apparatus to the native valve and/or to ventricle 6. The looped guide member is typically advanced toward ventricle 6 over guidewire 306, e.g., as described hereinabove with reference to FIG. 7A.

Figure 16A:
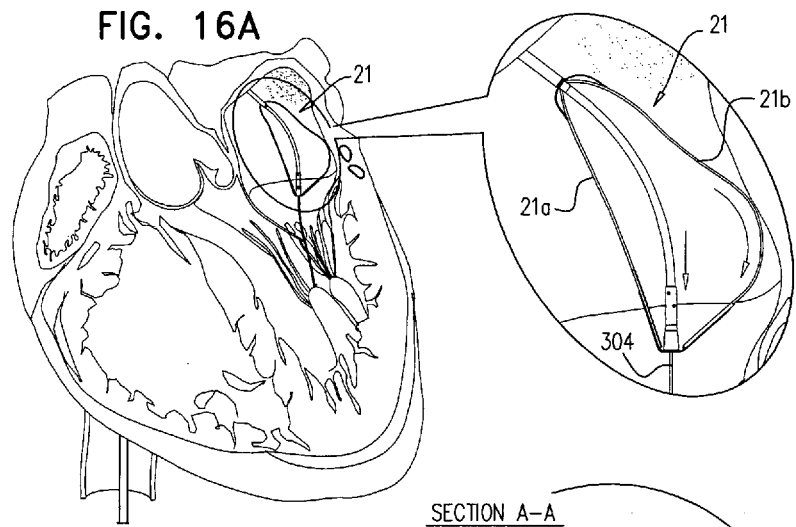

Typically, as shown in FIG. 16A, portions 21a and 21b of the looped guide member are independently manipulable. The portions of the looped guide member are manipulated (e.g., expanded and contracted) so as to guide the looped guide member to the subject's native valve, by pushing against inner surfaces of the subject's heart, as shown in FIG. 16A.

Figure 16B:
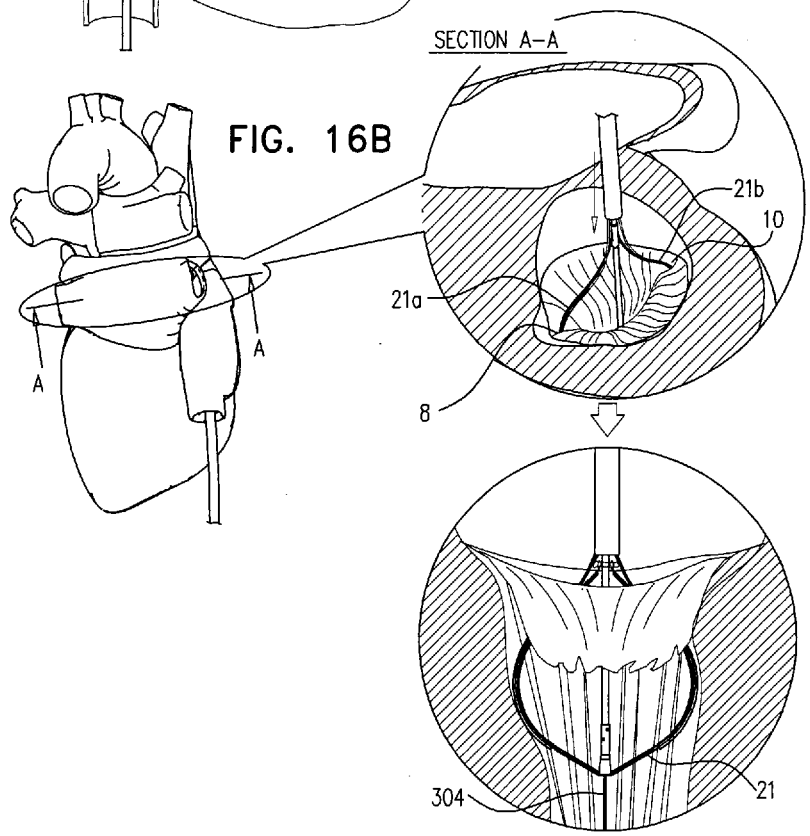

FIG. 16B shows the looped guide member looped through commissures 8 and 10 of the subject's native valve. When the looped guide member is disposed at the native valve, the guide member is used to guide and to anchor valve support 40, as described hereinbelow.

As shown in FIG. 16C, for some applications, looped guide member 21 is coupled to valve support 40 via coupling wires 500 and coupling mechanisms 502. For example, as shown, the coupling mechanism may include an anchor. A suture 504, or a different looped element, protrudes from the bottom surface of annular element 44 of valve support 40 and is anchored by the anchor. Thus, when looped guide member 21 is pushed distally into ventricle 6, the valve support is pulled against the annulus of the native valve by coupling wires 500 pulling on the valve support.

Typically, coupling mechanisms 502, which are used to couple looped guide member 21 to valve support 40 are detachable coupling mechanisms. For example, as shown, the coupling mechanism may include an anchor that defines an opening 506 through which suture 504 is inserted. The opening is closed by a closing member 508, such as a rod, or a wire. In order to detach the guide member from valve support, closing member 508 is opened (e.g., by being pulled proximally) such that suture 504 is released through opening 506.

Figure 16D:
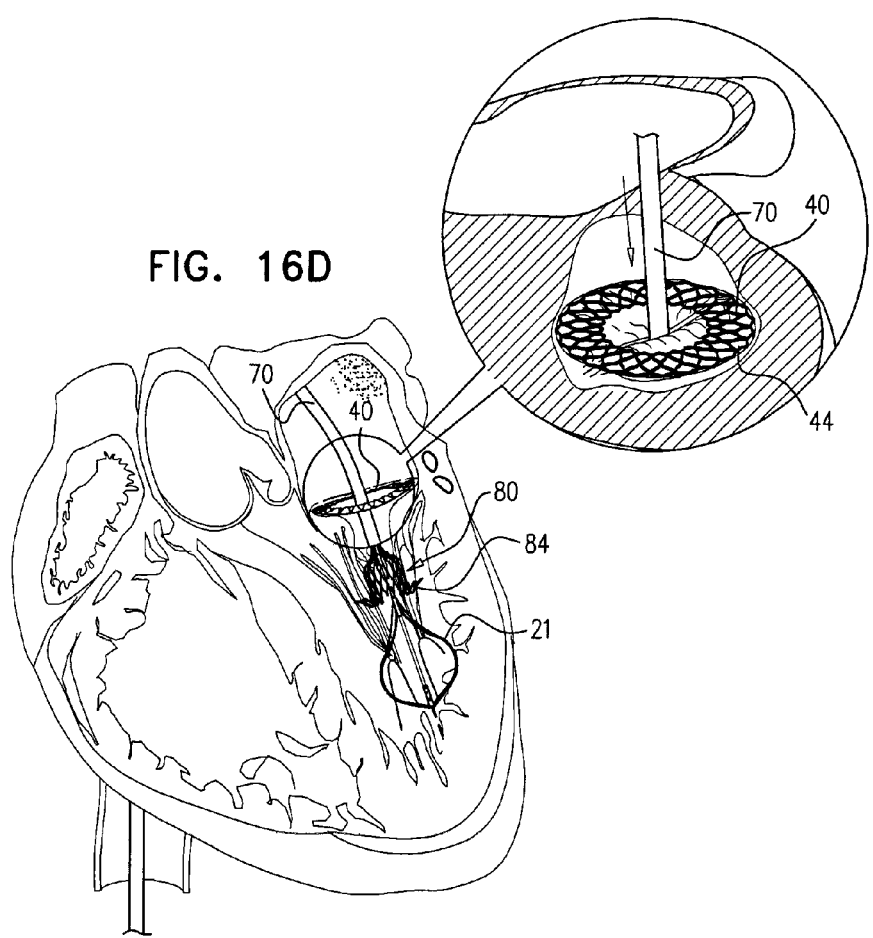
Figure 16E:
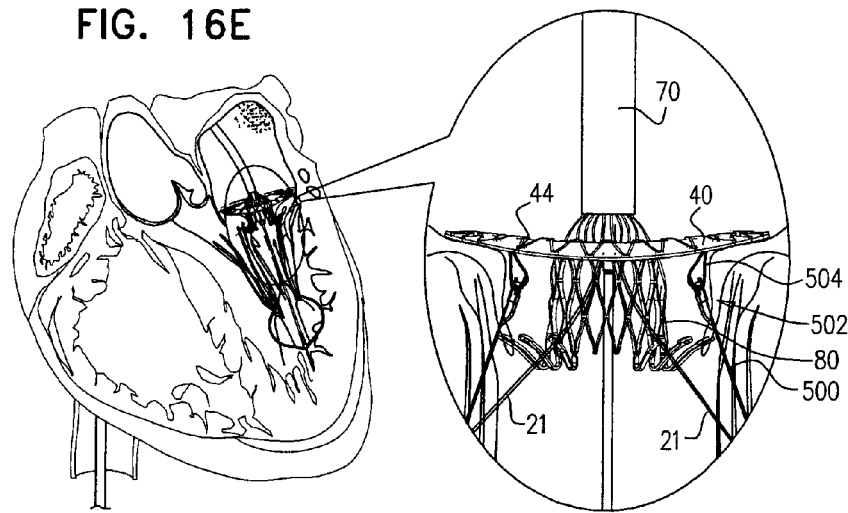
Figure 16F:
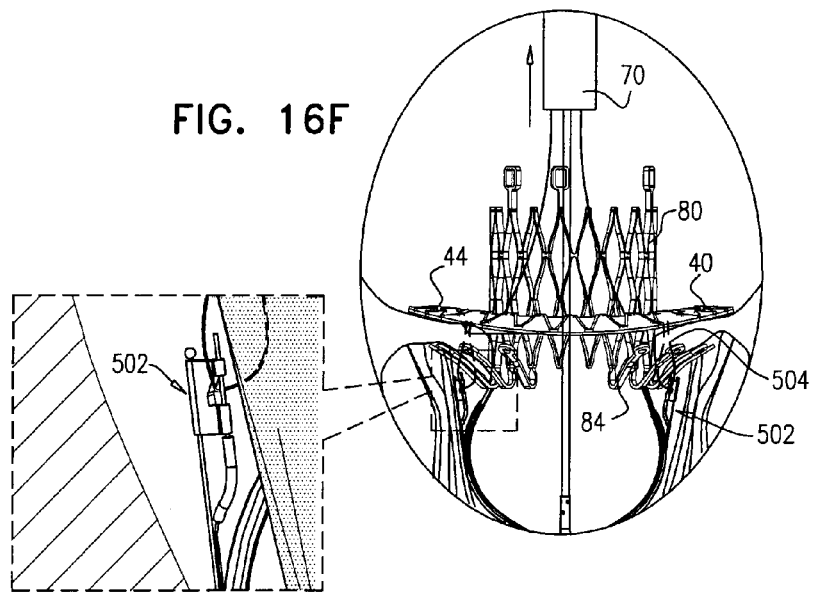

Subsequent to the placement of valve support 40 at the native valve, prosthetic atrioventricular valve 80 is placed in ventricle 6, by advancing overtube 70 into the ventricle, as shown in FIG. 16D. FIG. 16E shows prosthetic valve having been partially deployed in the ventricle. Following the partial deployment of valve 80 in ventricle 6, overtube 70 is pulled proximally to pull valve 80 proximally such that annular element 44 of valve support 40 surrounds a proximal portion of prosthetic valve 80, as shown in FIGS. 16E-F. Valve 80 has a tendency to expand such that valve 80 is held in place with respect to valve support 40 responsively to radial forces acted upon valve support 40 by prosthetic valve 80.

During the pulling back of overtube 70, looped guide member 21 is pushed distally, thereby pulling valve support 40 against the native annulus and providing a counter force against which overtube 70 is pulled back. For some applications, pulling of the valve support against the native annulus is such that it is not necessary to use anchors for anchoring the valve support to the native valve during the coupling of the prosthetic valve to the valve support. Alternatively, in addition to the pulling of the valve support against the native annulus providing a counter force against which the prosthetic valve is pulled, anchors are used to anchor the valve support to the native valve during the coupling of the prosthetic valve to the valve.

Figure 16G:
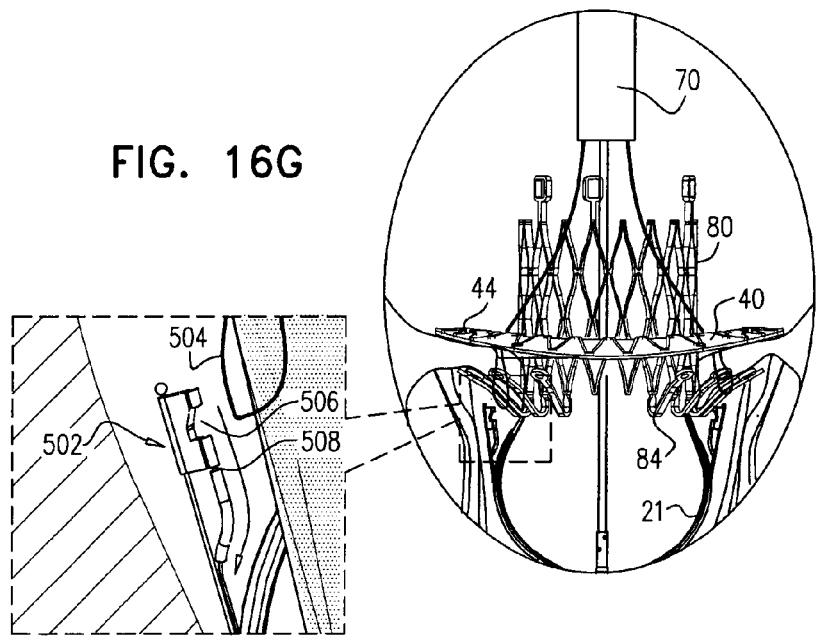
Figure 16H:
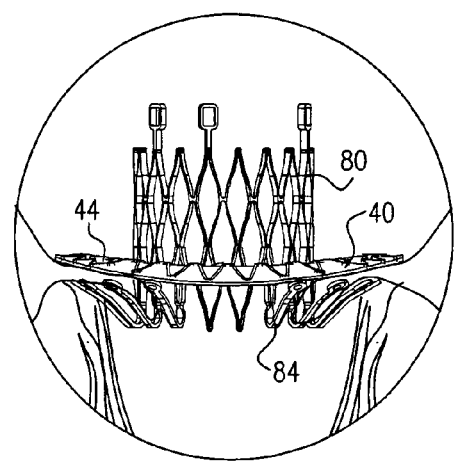

FIG. 16G shows prosthetic valve 80 and valve support 40 coupled to the native valve. At this stage, coupling mechanism 502 is typically detached from the valve support. For example, as shown, closing member 508 is pulled, such that opening 506 is opened, and suture 504 is released through the opening. Subsequently, looped guide member 21, and overtube 70 are removed from the subject's body, as shown in FIG. 16H, which shows the prosthetic valve in its deployed state.

As described with reference to FIGS. 16A-H, for some applications, prosthetic valve 80 is coupled to a native valve, by (a) placing valve support 40 on an atrial side of the native annulus, (b) placing the prosthetic valve inside the ventricle, and then, simultaneously, (c) pulling the prosthetic valve toward the atrium, and pulling the valve support toward the ventricle.

Figure 17A:
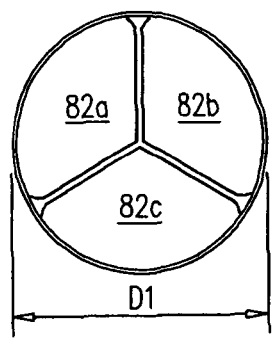
FIGS. 17A-C are schematic illustrations of leaflets of a prosthetic valve, in accordance with some applications of the present invention.
Figure 17B:
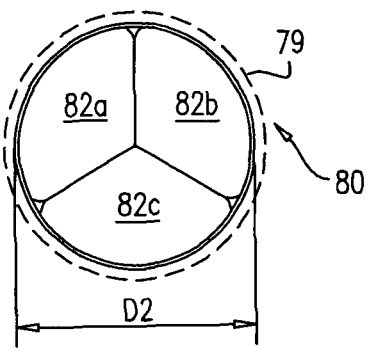
Figure 17C:
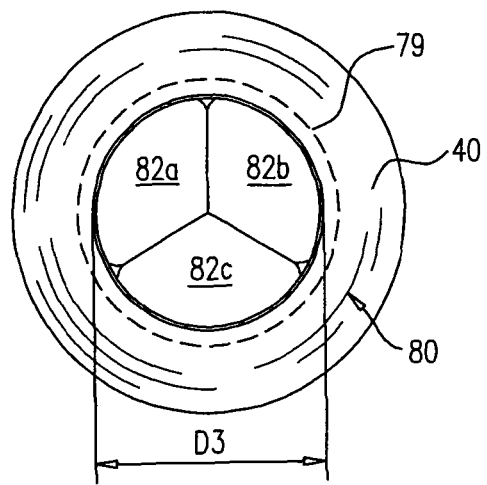

Reference is now made to FIGS. 17A-C, which are schematic illustrations of leaflets 82 of prosthetic valve 80, in accordance with some applications of the present invention. FIG. 17A shows the leaflets before the leaflets are sutured to expandable frame 79 of the valve. As shown, in this state, the leaflets have a diameter D1, and the leaflets are not fully closed. FIG. 17B shows the leaflets when the leaflets have been sutured to expandable frame 79 of the prosthetic valve. The expandable frame constrains the leaflets, such that the leaflets define a diameter D2, which is smaller than diameter D1, thereby closing the leaflets. FIG. 17C shows the leaflets subsequent to the deployment of valve 80 inside valve support 40, the valve support constraining the expansion of the prosthetic valve. Due to the valve support constraining the prosthetic valve, the valve leaflets are constrained so as define a diameter D3, which is smaller than diameter D2.

Typically, valve leaflets 82 are selected to be used in prosthetic valve 80, the leaflets being sized such that both at diameter D2 (when the leaflets are constrained by expandable frame 79 but are not constrained by valve support 40) and at diameter D3 (when the leaflets are constrained by both expandable frame 79 and valve support 40), the valve leaflets fully coapt.

Figure 18A:
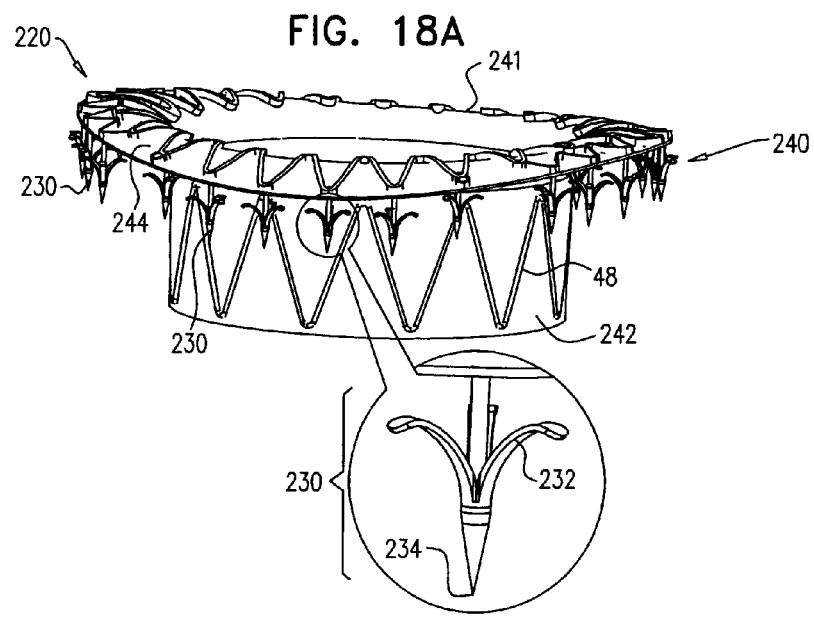
FIGS. 18A-B are schematic illustrations of a valve support coupled to a plurality of tissue anchors, in accordance with some applications of the present invention.
Figure 18B:
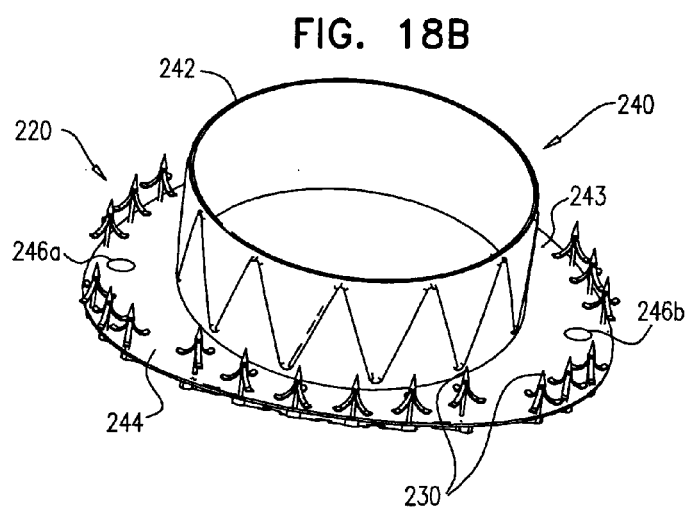

Reference is now made to FIGS. 18A-B which are schematic illustrations of a system 220 comprising a valve support 240 comprising an annular element 244 and a cylindrical element 242 and one or more (e.g., a plurality, as shown, of) tissue anchors 230, in accordance with some applications of the present invention. Annular element 244 has an upper surface 241 and a lower surface 243. Tissue anchors 230 are coupled to lower surface 234 of annular element. Tissue anchors 230 are shaped so as to define a pointed distal tip 234 and one or more (e.g., three, as shown) radially-expandable prongs 232. Prongs 232 comprise a flexible metal, e.g., nitinol or stainless steel, and have a tendency to expand radially. Anchors 230 facilitate coupling of valve support 240 to annulus 11 of native valve 5, such as the mitral valve or the tricuspid valve. Anchors 230 are typically distributed approximately evenly around lower surface 243 of annular element 244. For some applications, one or more anchors 230 are disposed at a location of annular element that is configured to be positioned adjacently to commissures 8 and 10 of valve 5.

Reference is now made to FIGS. 19A-D which are schematic illustrations of valve support 240 being implanted at valve 5 and the subsequent coupling of prosthetic valve 80 to valve support 240. Valve support 240 is advanced toward native valve 5 by pushing elements 52a and 52b, as described hereinabove with respect to valve support 40 with reference to FIGS. 2D-F. In response to the pushing force to valve support 240 by pushing elements 52a and 52b, anchors 230 are pushed into tissue of annulus 11 of valve 5. The pushing force by elements 52a and 52b is sufficient to implant each one of the plurality of anchors that are distributed around lower surface 243 of annular element 244.

FIG. 19A shows initial penetration of tissue of annulus 11 by pointed distal tip 234 of anchor 230. In FIG. 19B, the initial force of the tissue on prongs 232 pushes inwardly prongs 232. Finally, in FIG. 19C, prongs 232 expand within tissue of annulus 11 to assume a flower shape and a larger surface area to restrict proximal motion of anchor 230 and thereby anchor valve support 240 in tissue of annulus 11. As shown in FIGS. 19A-C, the cylindrical element of valve support 240 pushes aside native leaflets 12 and 14 of valve 5.

In FIG. 19D, prosthetic valve 80 is coupled to valve support 240, in a manner as described hereinabove.

It is noted that, in general, prosthetic valve 80 is self-expandable. When the prosthetic valve is deployed (i.e., when the valve self-expands) inside the subject's heart, the expansion of the valve is typically constrained by valve support 40. Further typically, the expansion of the valve is not constrained by the native annulus.

For some application, by constraining the expansion of the prosthetic valve with the valve support, the deployed cross-sectional area of the prosthetic valve may be fixed at a given area, by using a valve support that defines a hole having the given cross-sectional area. As described hereinabove with reference to FIG. 10, for some applications, the area defined by the native annulus is measured, and the cross-sectional area of the prosthetic valve that is to be deployed in the valve is selected based upon the measured area of the native annulus. Alternatively or additionally, valve support 40 is selected based upon the measured area of the native annulus.

For example, a valve support may be selected such that the valve support constrains the expansion of the prosthetic valve, when the cross-sectional area of the prosthetic valve is less than 90% (e.g., less than 80%, or less than 60%) of the area defined by the native annulus. As described hereinabove, for some applications, placing a prosthetic valve inside the native valve with the dimensions of the native valve annulus and the prosthetic valve being as described, facilitates sealing of the prosthetic valve with respect to the native valve, by the native valve leaflets closing around the outer surface of the prosthetic valve.

For some applications, the expansion of prosthetic valve 80 against valve support 40 couples the prosthetic valve to the valve support, and/or couples the valve and the valve support to the native mitral valve. Typically, the expansion of the prosthetic valve against the valve support couples the prosthetic valve to the valve support, and sandwiching of the native valve leaflets between protrusions from the distal end of the valve and the valve support couples the prosthetic valve and the valve support to the native valve.

Reference is now made to FIGS. 1A-D, 2A-K, 3A-D, 4A-C, 5A-D, 6A-B, 7A-F, 8A-C, 9A-H, 10, 11A-D, and 12A-C. It is to be noted that valve support 40 may be invertible as described hereinabove with respect to valve supports 140 and 300, with reference to FIGS. 8A-C, and 9A-H. It is to be further noted that valve supports 140 and 300 may be used in conjunction with one or more of the elements for facilitating sealing of the native valve with respect to a valve support or a valve that is described with reference to FIGS. 3A-D, 4A-C, 5A-D, and 6A-B. For example, valve supports 140 and 300 may be used with sealing balloon 90, commissural anchors 100a and 100b, grasping elements 106a and 106b, and/or sealing material 110. It is still further noted that valve supports 140 and 300 may be implanted using a guide member that defines a looped portion between commissures 8 and 10, as described with reference to FIGS. 7A-F. It is further noted that any of the applications described herein can be used in conjunction with valves having configurations as described with reference to FIGS. 10-12C.

The systems described herein are advanced toward valve 5 in a transcatheter procedure, as shown. It is to be noted, however, that the systems described herein may be advanced using any suitable procedure, e.g., minimally-invasively (e.g., via a transeptal, a transatrial, a transapical, and/or a transaortic approach), or using an open-heart procedure. It is to be further noted that valve supports and prosthetic valves herein may be used to replace native mitral valves or native tricuspid valves.

Reference is now made to FIGS. 20A-B, which are schematic illustrations of valve support 40 and prosthetic valve 80 coupled respectively to a tricuspid valve, and to an aortic valve, in accordance with some applications of the present invention. For some applications, valve support 40 and prosthetic valve 80 are deployed at a tricuspid valve and/or at an aortic valve using generally similar techniques to those described herein with reference to the deployment of the valve support and the prosthetic valve at the mitral valve, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The inention claimed is:

1. A method for use with a native valve of a heart of the subject, the native valve having an annulus and being disposed between an atrium of the heart and a ventricle of the heart, the method comprising:
through a sheath, transluminally advancing a prosthetic valve support, in a compressed state thereof, into the atrium;
placing the prosthetic valve support against an atrial surface of the annulus;
inhibiting upstream movement of the prosthetic valve support away from the annulus:
through the sheath, transluminally advancing an expandable prosthetic valve, comprising an expandable frame, to the heart;

deploying a downstream end of the prosthetic valve within the ventricle, the downstream end comprising a plurality of snares;

while upstream movement of the prosthetic valve support is inhibited, sandwiching tissue of the native valve between the snares and the prosthetic valve support by moving the prosthetic valve in an upstream direction, such that at least part of the prosthetic valve is disposed within the prosthetic valve support; and while the tissue is sandwiched and at least the part of the prosthetic valve is disposed within the prosthetic valve support, expanding the prosthetic valve such that the prosthetic valve becomes held in place with respect to the prosthetic valve support.

2. The method according to claim 1, further comprising anchoring an anchor to the native valve prior to advancement of the prosthetic valve support, and wherein inhibiting upstream movement of the prosthetic valve support away from the annulus comprises coupling the prosthetic valve support to the anchor.

3. The method according to claim 1, wherein inhibiting upstream movement of the prosthetic valve support away from the annulus comprises pushing the prosthetic valve support against the annulus using a pushing element.

4. The method according to claim 1, wherein:
the prosthetic valve comprises a frame that is self-expandable,
advancing the expandable prosthetic valve comprises advancing the expandable prosthetic valve while the expandable prosthetic valve is disposed in a compressed state within an overtube, and
expanding the prosthetic valve comprises facilitating self-expansion of the prosthetic valve by exposing the prosthetic valve from within the overtube.

5. The method according to claim 1, wherein advancing the prosthetic valve comprises advancing the prosthetic valve independently of advancing the prosthetic valve support.

6. The method according to claim 1, wherein advancing the prosthetic valve comprises advancing the prosthetic valve subsequently to advancing the prosthetic valve support.

7. The method according to claim 1, wherein the steps of advancing the prosthetic valve support, placing the prosthetic valve support, inhibiting upstream movement, advancing the prosthetic valve, deploying the downstream end of the prosthetic valve, sandwiching the tissue, and expanding the prosthetic valve, are performed without the use of cardiopulmonary bypass.

8. The method according to claim 1, wherein placing the prosthetic valve support against the atrial surface of the annulus comprises placing the prosthetic valve support against the atrial surface of the annulus while the native valve continues to function.

9. The method according to claim 1, wherein expanding the prosthetic valve comprises expanding the prosthetic valve until the expansion of the prosthetic valve is constrained by the prosthetic valve support.

\* \* \* \* \*